(12) United States Patent
Conner et al.

(10) Patent No.: US 7,078,503 B2
(45) Date of Patent: Jul. 18, 2006

(54) PLANT REGULATORY SEQUENCES FOR SELECTIVE CONTROL OF GENE EXPRESSION

(75) Inventors: Timothy W. Conner, Wildwood, MO (US); Patrice Dubois, Richmond Heights, MO (US); Marianne Malven, Ellisville, MO (US); James D. Masucci, Manchester, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 688 days.

(21) Appl. No.: 09/894,633

(22) Filed: Jun. 28, 2001

(65) Prior Publication Data

US 2002/0124285 A1    Sep. 5, 2002

Related U.S. Application Data

(60) Provisional application No. 60/214,357, filed on Jun. 28, 2000.

(51) Int. Cl.
*C07H 21/02* (2006.01)
*C12N 15/82* (2006.01)

(52) U.S. Cl. ............ 536/23.1; 800/278; 800/295

(58) Field of Classification Search ........... 536/24.1, 536/23.1, 24.3, 24.31; 435/6; 800/2
See application file for complete search history.

(56) References Cited
OTHER PUBLICATIONS

Zabaleta et al, "Promoters of nuclear encoded respiratory chain complex I genes from arabidopsis thaliana contain a region essential for anther/pollen specific expression", The Plant Journal, (1998) 15(1):49-59.*

Genbank Accession No. AP001526, May 30, 2000.*

Nilsson et al, "Expression of two heterologous promoters, Agrobacterium rhizogenes rolC and cauliflower mosaic virus 35S, in the stem of transgenichybrid aspen plants during the annual cycle of growth and dormancy", Plant Mol. Biol. (1996) 31:887-895.*

Hamilton et al., A monocot pollen-specific promoter contains separable pollen-specific and quantitative elements. Plant Mol. Biol. 38: 663-669 (1998).

Twell et al., Promoter analysis of genes that are coordinately expressed during pollen development reveals pollen-specific enhancer sequences and shared regulatory elements. Genes & Development 5: 496-507 (1991).

Tsuchiya et al., Molecular characterization of rice genes specifically expressed in the anther tapetum. Plant Mol. Biol. 26:1737-1746 (1994).

Custers et al., Analysis of micro-specific promoters in transgenic tobacco. Plant Mol. Biol. 35:689-699 (1997).

* cited by examiner

*Primary Examiner*—Jeffrey Fredman
(74) *Attorney, Agent, or Firm*—Forchisha M. Davis; Monsanto Company

(57) ABSTRACT

Promoters from male reproductive tissues are isolated from corn. These promoters can be used in plants to regulate transcription of target genes including genes for control of fertility, insect or pathogen tolerance, herbicide tolerance or any gene of interest.

12 Claims, 2 Drawing Sheets

PLANT REGULATORY SEQUENCES FOR SELECTIVE CONTROL OF GENE EXPRESSION

RELATED APPLICATION DATA

This application claims priority to U.S. Provisional Application 60/214,357, filed on Jun. 28, 2000.

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al., 1995, World Journal of Microbiology and Biotechnology 11: 449–460). Particularly desirable traits or qualities of interest for plant genetic engineering would include, but are not limited to, resistance to insects, fungal diseases, and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Because the promoter is a regulatory element that plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing that can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest for the newly inserted DNA to be transcribed and thereby, if desired, translated into a protein in the plant cell. These regulatory sequences include, but are not limited to, a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include, but are not limited to, inducible promoters that can be triggered by external stimuli such as chemical agents, developmental stimuli, or environmental stimuli. Thus, the different types of promoters desired can be obtained by isolating the regulatory regions of DNA sequences that are transcribed and expressed in a constitutive, tissue-enhanced, or inducible manner.

The technological advances of high-throughput sequencing and bioinformatics have provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced, and the expressed sequences can be catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue-enhanced sequence can then be used as a probe or primer to clone the corresponding full-length cDNA. A genomic library of the target plant can then be used to isolate the corresponding gene and the associated regulatory elements, including but not limited to promoter sequences.

Multiple genes that have a desired expression profile such as in male reproductive tissues can be isolated by selectively comparing cDNA libraries of target tissues of interest with non-target or background cDNA libraries to find the 5' regulatory regions associated with the expressed sequences in those target libraries. The promoter sequences can be isolated from the genomic DNA flanking the desired genes. The isolated promoter sequences can be used for selectively modulating expression of any operatively linked gene and provide additional regulatory element diversity in a plant expression vector in gene stacking approaches.

SUMMARY OF THE INVENTION

The present invention provides isolated plant promoter sequences that comprise nucleic acid regions located upstream of the 5' end of plant DNA structural coding sequences that are transcribed in male reproductive tissues. The plant promoter sequences are capable of modulating or initiating transcription of DNA sequences to which they are operably linked.

The present invention provides nucleic acid sequences comprising regulatory sequences as shown in SEQ ID NOS: 80–111 that are located upstream of the 5' end of plant DNA structural coding sequences and transcribed in male reproductive tissues.

In one aspect, the present invention provides nucleic acid sequences comprising a sequence selected from the group consisting of SEQ ID NOS: 80–111 or any fragments or regions of the sequence or cis elements of the sequence that are capable of regulating transcription of operably linked DNA sequences.

The present invention also provides nucleic acid sequences comprising a sequence selected from the group consisting of SEQ ID NOS: 80–111 that are promoters.

Another aspect of the present invention relates to the use of one or more cis elements, or fragments thereof of the disclosed 5' promoter sequences that can be combined to create novel promoters or used in a novel combination with another heterologous regulatory sequence to create a chimeric promoter capable of modulating transcription of an operably linked DNA sequence.

Hence, the present invention relates to the use of nucleic acid sequences disclosed in SEQ ID NOS: 80–111 or any fragment, region, or cis element of the disclosed sequences that are capable of regulating transcription of a DNA sequence when operably linked to the DNA sequence. Therefore, the invention not only encompasses the sequences as disclosed in SEQ ID NOS: 80–111, but also includes any truncated or deletion derivatives, or fragments or regions thereof that are capable of functioning independently as a promoter including cis elements that are capable of functioning as regulatory sequences in conjunction with one or more regulatory sequences when operably linked to a transcribable sequence.

The present invention thus encompasses a novel promoter or chimeric or hybrid promoter comprising a nucleic acid of SEQ ID NOS: 80–111. The chimeric or hybrid promoters can consist of any length fragments, regions, or cis elements of the disclosed sequences of SEQ ID NOS: 80–111 combined with any other transcriptionally active minimal or full-length promoter. For example, a promoter sequence selected from SEQ ID NOS: 80–111 may be combined with a CaMV 35S or other promoter to construct a novel chimeric promoter. A minimal promoter can also be used in combination with the nucleic acid sequences of the present invention. A novel promoter also comprises any promoter constructed by engineering the nucleic acid sequences disclosed in SEQ ID NOS: 80–111 or any fragment, region, or cis element of the disclosed sequences in any manner sufficient to transcribe an operably linked DNA sequence.

Another aspect of the present invention relates to the ability of the promoter sequences of SEQ ID NOS: 80–111, or fragments, regions, or cis elements thereof to regulate transcription of operably linked transcribable sequences in male reproductive tissues. Fragments, regions, or cis elements of SEQ ID NOS: 80–111 that are capable of regulating transcription of operably linked DNA sequences in certain tissues may be isolated from the disclosed nucleic acid sequences of SEQ ID NOS: 80–111 and used to engineer novel promoters.

The present invention also encompasses DNA constructs comprising the disclosed sequences as shown in SEQ ID NOS: 80–111 or any fragments, regions, or cis elements thereof, including novel promoters generated using the disclosed sequences or any fragment, region, or cis element of the disclosed sequences.

The present invention also includes any transgenic cells and plants containing the DNA disclosed in the sequences as shown in SEQ ID NOS: 80–111, or any fragments, regions, or cis elements thereof.

The present invention also provides a method of regulating transcription of a DNA sequence comprising operably linking the DNA sequence to any promoter comprising a nucleic acid comprising all or any fragment, region or cis element of a sequence selected from the group consisting of SEQ ID NOS: 80–111.

In another embodiment the present invention provides a method of regulating expression of DNA sequences in male reproductive tissues by operably linking a sequence selected from the group consisting of SEQ ID NOS: 80–111, or any fragment, region, or cis element of the disclosed sequences to any transcribable DNA sequence. The fragments, regions, or cis elements of the disclosed promoters as shown in SEQ ID NOS: 80–111 can be engineered and used independently in novel combinations including multimers, or truncated derivatives and the novel promoters can be operably linked with a transcribable DNA sequence. Alternatively the disclosed fragments, regions, or cis elements of the disclosed sequences can be used in combination with a heterologous promoter including a minimal promoter to create a novel chimeric or hybrid promoter and the novel chimeric promoter can be operably linked to a transcribable DNA sequence.

The present invention also provides a method of making a transgenic plant by introducing into a cell of a plant a DNA construct comprising: (i) a promoter comprising a nucleic acid comprising a sequence selected from the group consisting of SEQ ID NOS: 80–111, or fragment, region, or cis element thereof, and operably linked to the promoter, (ii) a transcribable DNA sequence and (iii) a 3' untranslated region.

The present invention also provides a method of isolating at least one 5' regulatory sequence of a desired expression profile from a target plant of interest by evaluating a collection of nucleic acid sequences of ESTs derived from one or more cDNA libraries prepared from a plant cell type of interest, comparing EST sequences from at least one target plant cDNA library and one or more non-target cDNA libraries of ESTs from a different plant cell type, subtracting common EST sequences found in both target and non-target libraries, designing gene-specific primers from the remaining ESTs after the subtraction that are representative of the targeted expressed sequences, and isolating the corresponding 5' flanking and regulatory sequences, that includes promoter sequences from a genomic library prepared from the target plant using the gene specific primers.

The foregoing and other aspects of the invention will become more apparent from the following detailed description and accompanying drawings.

BRIEF DESCRIPTION OF THE SEQUENCE LISTING

Figure 1:
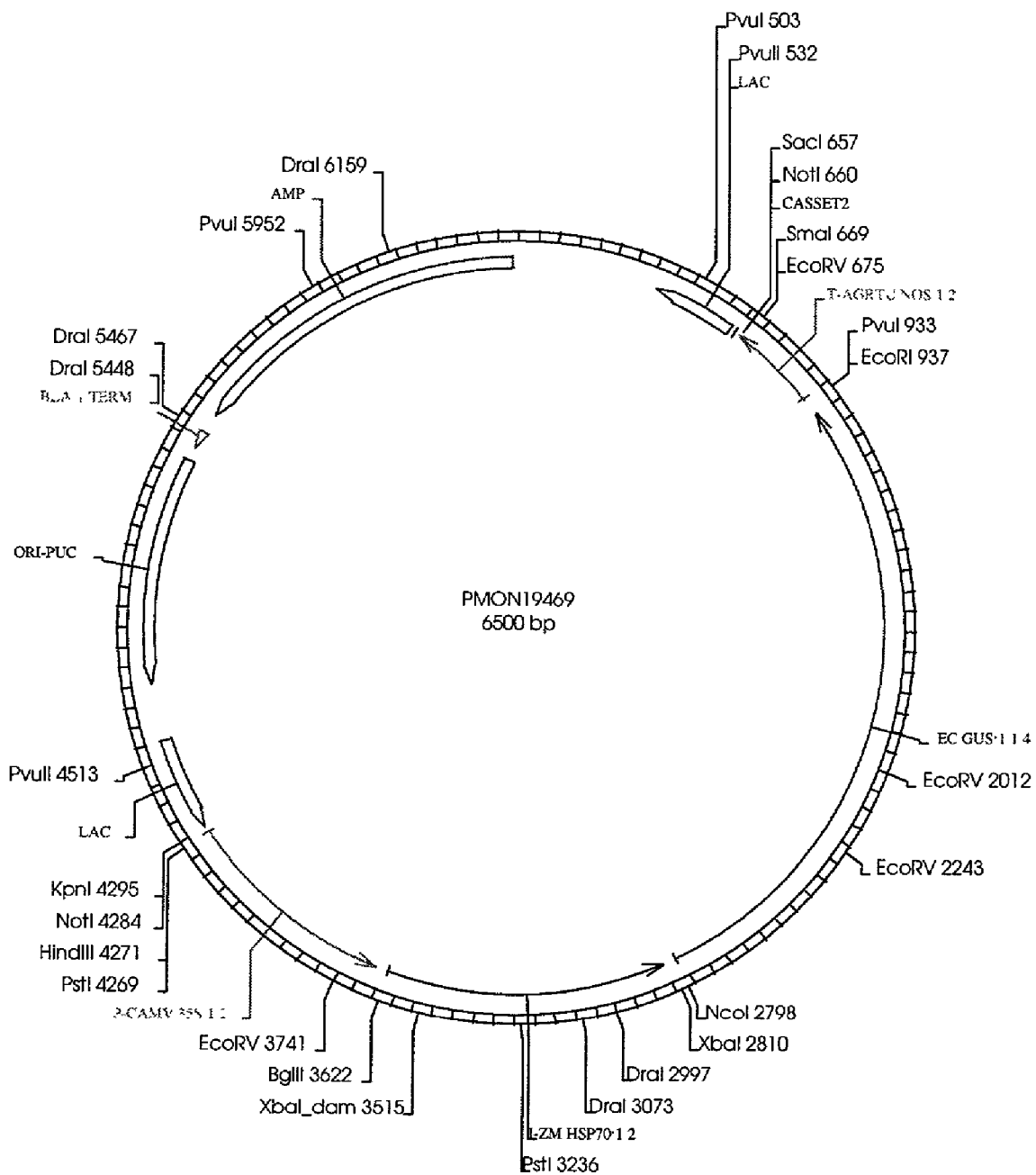
FIG. 1 is a plasmid map of pMON19469.

SEQ ID NOS: 1–3 are adaptor primer sequences.
SEQ ID NOS: 4–79 are fully synthesized primers derived from known *Zea mays* sequences.
SEQ ID NOS: 80–111 are promoter sequences isolated from *Zea mays*.

DETAILED DESCRIPTION OF THE INVENTION

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR § 1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence that originates from a foreign source or species or, if from the same source, is modified from its original form.

An "isolated" nucleic acid sequence is substantially separated or purified away from other nucleic acid sequences that the nucleic acid is normally associated with in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified", as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman (Adv. Appl. Math. 2: 482, 1981); by the homology alignment algorithm of Needleman and Wunsch (J. Mol. Biol. 48:443, 1970); by the search for similarity method of Pearson and Lipman (Proc. Natl. Acad. Sci. USA 85:2444, 1988); preferably by computerized implementations of these algorithms (GAP, BESTFIT, FASTA, and TFASTA) in the Wisconsin Genetics Software Package Release 7.0 (Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., *Molecular Cloning: A Laboratory Manual,* 2nd ed., vol. 1–3, ed. Sambrook et al., Cold Spring Harbor Laboratory Press, Cold Spring Harbor, N.Y., 1989; *Current Protocols in Molecular Biology*, ed. Ausubel et al., Greene Publishing and Wiley-Interscience, New York, 1992, with periodic updates, 1992; and *PCR Protocols: A Guide to Methods and Applications*, Academic Press: San Diego, Innis et al., 1990). Methods for chemical synthesis of nucleic acids are discussed, for example, in Beaucage and Carruthers (Tetra. Letts. 22: 1859–1862, 1981), and Matteucci et al. (J. Am. Chem. Soc. 103: 3185, 1981). Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc. (University of Wisconsin Biotechnology Center, Madison, Wis.).

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and by Innis et al. (*PCR Protocols: A Guide to Methods and Applications*, Academic Press, San Diego, 1990). In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing (A-G-T pairs with the complementary sequence A-C-T). Complementarity between two single-stranded molecules may be partial, if only some of the nucleic acids pair are complementary, or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"ESTs" or Expressed Sequence Tags are short sequences of randomly selected clones from a cDNA (or complementary DNA) library that are representative of the cDNA inserts of these randomly selected clones (McCombie et al., Nature Genetics, 1: 124, 1992; Kurata et al., Nature Genetics, 8: 365,1994; Okubo et al., Nature Genetics, 2: 173, 1992).

The term "electronic Northern" refers to a computer-based sequence analysis that allows sequences from multiple cDNA libraries to be compared electronically based on parameters the researcher identifies including abundance in EST populations in multiple cDNA libraries, or exclusively to EST sets from one or combinations of libraries.

"Subsetting" refers to a method of comparing nucleic acid sequences from different or multiple sources that can be used to assess the expression profile of the nucleic acid sequences that reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example, by chemical compounds (chemical inducers) or in response to environmental, hormonal, chemical, or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulating expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50: 349–383, 1981; Messing et al., In: Genetic Engineering of Plants, Kosuge et al., eds, pp. 211–227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds, pp. 211–227, 1983). In addition, virtually all promoters include additional upstream activating sequences or enhancers (Benoist and Chambon, Nature 290: 304–310, 1981; Gruss et al., Proc. Natl. Acad. Sci. USA 78: 943–947, 1981; and Khoury and Gruss, Cell 27: 313–314, 1983) extending from around −100 bp to −1,000 bp or more upstream of the transcription initiation site. Enhancers have also been found 3' to the transcriptional start site.

When fused to heterologous DNA sequences, such promoters typically cause the fused sequence to be transcribed in a manner that is similar to that of the gene sequence that the promoter is normally associated with. Promoter fragments that include regulatory sequences can be added (for example, fused to the 5' end of, or inserted within, an active promoter having its own partial or complete regulatory sequences (Fluhr et al., Science 232: 1106–1112, 1986; Ellis et al., EMBO J. 6: 11–16, 1987; Strittmatter and Chua, Proc. Nat. Acad. Sci. USA 84: 8986–8990, 1987; Poulsen and Chua, Mol. Gen. Genet. 214: 16–23, 1988; Comai et al., Plant Mol. Biol. 15: 373–381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232: 1106–1112, 1986; Strittmatter and Chua, Proc. Nat. Acad. Sci. USA 84: 8986–8990, 1987; Aryan et al., Mol. Gen. Genet. 225: 65–71, 1991).

Promoters are typically comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84: 8986–8990, 1987; Ellis et al., EMBO J. 6: 11–16, 1987; Benfey et al., EMBO J. 9: 1677–1684, 1990). Cis elements bind trans-acting protein factors that regulate transcription. Some cis elements bind more than one factor, and trans-acting transcription factors may interact with different affinities with more than one cis element (Johnson and McKnight, Ann. Rev. Biochem. 58: 799–839, 1989). Plant transcription factors, corresponding cis elements, and analysis of their interaction are discussed, for example, in Martin (Curr. Opinions Biotech. 7: 130–138, 1996), Murai (*Methods in Plant Biochemistry and Molecular Biology*, Dashek, ed., CRC Press, 1997, pp. 397–422), and Maliga et al. (*Methods in Plant Molecular Biology*, Cold Spring Harbor Press, 1995, pp. 233–300). The promoter sequences of the present invention can contain "cis elements" that can confer or modulate gene expression.

Cis elements can be identified by a number of techniques, including deletion analysis, i.e., deleting one or more nucleotides from the 5' end or internal to a promoter; DNA binding protein analysis using DNAse I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397–422; and *Methods in Plant Molecular Biology*, Maliga et al., eds, Cold Spring Harbor Press, 1995, pp. 233–300).

Cis elements can be obtained by chemical synthesis or by cloning from promoters that include such elements, and they can be synthesized with additional flanking sequences that contain useful restriction enzyme sites to facilitate subsequent manipulation. In one embodiment, the promoters are comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84: 8986–8990, 1987; Ellis et al., EMBO J. 6:11–16, 1987; Benfey et al., EMBO J. 9: 1677–1684, 1990). In a preferred embodiment, sequence regions comprising "cis elements" of the nucleic acid sequences of SEQ ID NOS: 80–111 are identified using computer programs designed specifically to identify cis elements, or domains or motifs within sequences.

The present invention includes cis elements of SEQ ID NOS: 80–111, or homologues of cis elements known to affect gene regulation that show homology with the nucleic acid sequences of the present invention. A number of such elements are known in the literature, such as elements that are regulated by numerous factors such as light, heat, or stress; elements that are regulated or induced by pathogens or chemicals, and the like. Such elements may either positively or negatively regulated gene expression, depending on the conditions. Examples of cis elements would include, but are not limited to, oxygen responsive elements (Cowen et al., J. Biol. Chem. 268(36): 26904, 1993), light regulatory elements (see for example, Bruce and Quail, Plant Cell 2(11): 1081, 1990; and Bruce et al., EMBO J. 10: 3015, 1991), a cis element responsive to methyl jasmonate treatment (Beaudoin and Rothstein, Plant Mol. Biol. 33: 835, 1997), salicylic acid responsive elements (Strange et al., Plant J. 11: 1315, 1997), heat shock response elements (Pelham et al., Trends Genet. 1: 31, 1985), elements responsive to wounding and abiotic stress (Loace et al., Proc. Natl. Acad. Sci. U. S. A. 89:9230, 1992; Mhiri et al., Plant Mol. Biol. 33: 257, 1997), low temperature elements (Baker et al., Plant Mol. Biol. 24: 701, 1994; Jiang et al., Plant Mol. Biol. 30: 679, 1996; Nordin et al., Plant Mol. Biol. 21: 641, 1993; Zhou et al., J. Biol. Chem. 267: 23515, 1992), and drought responsive elements, (Yamaguchi et al., Plant Cell 6: 251–264, 1994; Wang et al., Plant Mol. Biol. 28: 605, 1995; Bray, Trends in Plant Science 2: 48, 1997).

The present invention therefore encompasses fragments or cis elements of the disclosed nucleic acid molecules, and such nucleic acid fragments can include any region of the disclosed sequences. The promoter regions or partial promoter regions of the present invention as shown in SEQ ID NOS: 80–111 can contain one or more regulatory elements including but not limited to cis elements or domains that are capable of regulating expression of operably linked DNA sequences, preferably in male reproductive tissues.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11–16, 1987; Strittmatter and Chua, Proc. Nat. Acad. Sci. USA 84: 8986–8990, 1987; Poulsen and Chua, Mol. Gen. Genet. 214: 16–23, 1988; Comai et al., Plant. Mol. Biol. 15: 373–381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232: 1106–1112, 1986; Strittmatter and Chua, Proc. Nat. Acad. Sci. USA 84: 8986–8990, 1987; Aryan et al., Mol. Gen. Genet. 225: 65–71, 1991).

The design, construction, and use of chimeric or hybrid promoters comprising one or more of cis elements of SEQ ID NOS: 80–111 for modulating or regulating the expression of operably linked nucleic acid sequences is also encompassed by the present invention.

The promoter sequences, fragments, regions or cis elements thereof of SEQ ID NOS: 80–111 are capable of transcribing operably linked DNA sequences in male reproductive tissues and therefore can selectively regulate expression of genes in these tissues.

The promoter sequences of the present invention are useful for regulating gene expression in male reproductive tissues such as tassels, anthers, and pollen. For a number of agronomic traits, transcription of a gene or genes of interest is desirable in multiple tissues in order to confer the desired characteristic(s). The availability of suitable promoters that regulate transcription of operably linked genes in selected target tissues of interest is important because it may not be desirable to have expression of a gene in every tissue, but only in certain tissues. For example, if one desires to selectively express a target gene for controlling fertility in corn, it would be advantageous to have a promoter that confers enhanced expression in reproductive tissues. The promoter sequences of the present invention are capable of regulating operably linked DNA sequence particularly in male reproductive tissues and have utility for regulating transcription of any target gene including, but not limited to, genes for control of fertility, insect or pathogen tolerance, herbicide tolerance or any gene of interest. Consequently, it is important to have a wide variety of choices of 5' regulatory elements for any plant biotechnology strategy.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage or under particular environmental conditions. By identifying differentially expressed genes in plant tissues at different developmental stages or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis that compares the abundance of expressed genes in one or more libraries. The clones contained within a cDNA library are sequenced and the sequences compared with sequences from publicly available databases. Computer-based methods allow the researcher to provide queries that compare sequences from multiple libraries. The process enables quick identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis et al., Cell 7: 279, 1976; Higuchi et al., Proc. Natl. Acad. Sci. U.S.A. 73: 3146, 1976; Maniatis et al., Cell 8: 163, 1976; Land et al., Nucleic Acids Res. 9: 2251, 1981; Okayama et al., Mol. Cell. Biol. 2: 161, 1982; Gubler et al., Gene 25: 263, 1983).

Several methods can be employed to obtain full-length cDNA constructs. For example, terminal transferase can be used to add homopolymeric tails of dC residues to the free 3' hydroxyl groups (Land et al., Nucleic Acids Res. 9: 2251, 1981). This tail can then be hybridized by a poly dG oligo that can act as a primer for the synthesis of full-length second strand cDNA. Okayama and Berg reported a method for obtaining full-length cDNA constructs (Mol. Cell Biol. 2: 161, 1982). This method has been simplified by using synthetic primer adapters that have both homopolymeric tails for priming the synthesis of the first and second strands and restriction sites for cloning into plasmids (Coleclough et al., Gene 34: 305, 1985) and bacteriophage vectors (Krawinkel et al., Nucleic Acids Res. 14: 1913, 1986; Han et al., Nucleic Acids Res. 15: 6304, 1987).

These strategies can be coupled with additional strategies for isolating rare mRNA populations. For example, a typical mammalian cell contains between 10,000 and 30,000 different mRNA sequences (Davidson, Gene Activity in Early Development, 2nd ed., Academic Press, New York, 1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook et al.,1989).

One method to enrich preparations of mRNA for sequences of interest is to fractionate by size. One such method is to fractionate by electrophoresis through an agarose gel (Pennica et al., Nature 301: 214, 1983). Another method employs sucrose gradient centrifugation in the presence of an agent, such as methylmercuric hydroxide, that denatures secondary structure in RNA (Schweinfest et al., Proc. Natl. Acad. Sci. U.S.A. 79: 4997–5000, 1982).

A frequently adopted method is to construct equalized or normalized cDNA libraries (Ko, Nucleic Acids Res. 18: 5705, 1990; Patanjali et al., Proc. Natl. Acad. Sci. U.S.A. 88: 1943, 1991). Typically, the cDNA population is normalized by subtractive hybridization (Schmid et al., J. Neurochem. 48: 307, 1987; Fargnoli et al., Anal. Biochem. 187: 364, 1990; Travis et al., Proc. Natl. Acad. Sci. U.S.A. 85: 1696, 1988; Kato, Eur. J. Neurosci. 2: 704, 1990; Schweinfest et al., Genet. Anal. Tech. Appl. 7: 64, 1990). Subtraction represents another method for reducing the population of certain sequences in the cDNA library (Swaroop et al., Nucleic Acids Res. 19: 1954, 1991). Normalized libraries can be constructed using the Soares procedure (Soares et al., Proc. Natl. Acad. Sci. U.S.A. 91: 9228, 1994). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method (Sanger et al., Proc. Natl. Acad. Sci. U.S.A. 74: 5463, 1977) and the chemical degradation method (Maxam and Gilbert, Proc. Nat. Acad. Sci. U.S.A. 74: 560, 1977). Automation and advances in technology, such as the replacement of radioisotopes with fluorescence-based sequencing, have reduced the effort required to sequence DNA (Craxton, Methods, 2: 20, 1991; Ju et al., Proc. Natl. Acad. Sci. U.S.A. 92: 4347, 1995; Tabor and Richardson, Proc. Natl. Acad. Sci. U.S.A. 92: 6339, 1995). Automated sequencers are available from a number of manufacturers including Pharmacia Biotech, Inc., Piscataway, N.J. (Pharmacia ALF); LI-COR, Inc., Lincoln, Nebr. (LI-COR 4,000); and Millipore, Bedford, Mass. (Millipore BaseStation).

ESTs longer than 150 bp have been found to be useful for similarity searches and mapping (Adams et al., Science 252:1651, 1991). EST sequences normally range from 150–450 bases. This is the length of sequence information that is routinely and reliably generated using single run sequence data. Typically, only single run sequence data is obtained from the cDNA library (Adams et al., Science 252:1651, 1991). Automated single run sequencing typically results in an approximately 2–3% error or base ambiguity rate (Boguski et al., Nature Genetics, 4: 332, 1993).

EST databases have been constructed or partially constructed from, for example, *C. elegans* (McCombrie et al., Nature Genetics 1:124, 1992), human liver cell line HepG2 (Okubo et al., Nature Genetics 2:173, 1992), human brain RNA (Adams et al., Science 252:1651, 1991; Adams et al., Nature 355: 632, 1992), *Arabidopsis* (Newman et al., Plant Physiol. 106: 1241, 1994) and rice (Kurata et al., Nature Genetics 8: 365, 1994). The present invention uses ESTs from a number of cDNA libraries prepared from male reproductive tissues of corn as a tool for the identification of genes expressed in these target tissues, which then facilitates the isolation of 5' regulatory sequences such as promoters that regulate the genes.

Computer-based sequence analyses can be used to identify differentially expressed sequences including, but not limited to, those sequences expressed in one tissue compared with another tissue. For example, a different set of sequences can be found from cDNA isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library or a collection of cDNA libraries. For example, the identification of regulatory sequences that direct the expression of transcripts in male reproductive tissues is conducted by identifying ESTs found in tissues such as tassel and anther, and absent or in lower abundance in other cDNA libraries in the database. The identified EST leads are then evaluated for relative abundance within the library and the expression profile for a given EST is assessed. By abundance as used herein is meant the number of times a clone or cluster of clones appears in a library. The sequences that are enhanced or in high abundance in a specific tissue or organ that represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches.

In a preferred embodiment, genomic DNA ligated to an adaptor is subjected to a primary round of PCR amplification with a gene-specific primer and a primer that anneals to the adaptor sequence. The PCR product is next used as the template for a nested round of PCR amplification with a second gene-specific primer and second adaptor. The resulting fragments from the nested PCR reaction are then isolated, purified and subcloned into an appropriate vector. The fragments are sequenced, and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses, and subsequently the 5' regulatory regions are operably linked to other genes and regulatory sequences of interest in a suitable plant transformation vector and the transformed plants are analyzed for the expression of the gene(s) of interest, by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, elementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lily, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plant targets would include corn, cotton, rice, soybean, and wheat.

The nucleic acid molecules of the present invention are isolated from corn (*Zea mays*). The corn plant develops about 20–21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2, V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie et al., *How a Corn Plant Develops*, Iowa State University of Science and Technology Cooperative Extension Service, Ames, IA 48: 1–21, 1986).

Any type of plant tissue can be used as a target tissue for the identification of genes and associated regulatory sequences. For the present invention, corn male reproductive tissue is used. More preferably corn tassel tissues are the target tissues for identification of promoter sequences. Corn cDNA libraries can be constructed from several different plant developmental stages. More preferably corn plants at stages V6–V9 are used. Background or non-target libraries can include but are not limited to libraries such as leaf, root, embryo, callus, shoot, seedling, endosperm, culm, ear, and silks.

Any method that allows a differential comparison between different types or classes of sequences can be used to isolate genes or regulatory sequences of interest. For example, in one differential screening approach, a cDNA library from mRNA isolated from a particular tissue can be prepared in a bacteriophage host using a commercially available cloning kit. The plaques are spread onto plates containing lawns of a bacterial host such as *E. coli* to generate bacteriophage plaques. About $10^5$–$10^6$ plaques can be lifted onto DNA-binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage and prepared using a suitable vector such as a bacteriophage using a suitable cloning kit from any number of vendors (see for example Stratagene, La Jolla Calif. or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to multiple labeled cDNA probes prepared from RNA samples of different cell or tissue types, allowing direct comparative analysis of expression. This technology was first demonstrated by analyzing 48 *Arabidopsis* genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be done by determining the similarity of the test or query sequence with sequences in publicly available or proprietary databases ("similarity analysis") or by searching for certain motifs ("intrinsic sequence analysis") (e.g., cis elements) (Coulson, Trends in Biotechnology, 12: 76, 1994; Birren et al., Genome Analysis, 1: 543, 1997).

The nucleotide sequences provided in SEQ ID NOS: 80–111 or fragments thereof, or complements thereof, or a nucleotide sequence at least 90% identical, preferably 95% identical even more preferably 99% or 100% identical to the sequence provided in SEQ ID NOS: 80–111 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable media can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of skill in the art to access sequence information provided in a computer readable medium. Examples of public databases would include but are not limited to the DNA Database of Japan (DDBJ) (http://www.ddbj.nig.ac.jp/); Genbank (http://www.nebi.nlm.nih.gov/web/Genbank/Index.html); and the European Molecular Biology Laboratory Nucleic Acid Sequence Database (EMBL) (http://www.ebi.ac.uk/ebi_docs/embl_db.html) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12: 76–80, 1994; Birren et al., Genome Analysis, 1: 543, 1997).

Any program designed for motif searching also has utility in the present invention. Sequence analysis programs designed for motif searching can be used for identification of cis elements. Preferred computer programs would include but are not limited to MEME, SIGNAL SCAN, and GENESCAN. MEME is a program that identifies conserved motifs (either nucleic acid or peptide) in a group of unaligned sequences. MEME saves these motifs as a set of profiles. These profiles can be used to search a database of sequences. A MEME algorithm (Version 2.2) can be found in version 10.0 of the GCG package; MEME (Bailey and Elkan, Machine Learning, 21(1–2): 51–80,1995 and the location of the website is http://www.sdsc.edu/MEME/meme/website/COPYRIGHT.html. SIGNALSCAN is a program that identifies known motifs in the test sequences using information from other motif databases (Prestridge, CABIOS 7, 203–206, 1991). SIGNALSCAN version 4.0 information is available at the following website: http://biosci.cbs.umn.edu/software/sigscan.html. The ftp site for SIGNALSCAN is ftp://biosci.cbs.umn.edu/software/sigscan.html. Databases used with SIGNALSCAN include PLACE (http://www.dna.affrc.go.ip/htdocs/PLACE; Higo et al., Nucleic Acids Research 27(1): 297–300, 1999) and TRANSFAC (Heinemeye et al., Nucleic Acid Research 27(1): 318–322) that can be found at the following website: http://transfac.gbf.de/. GENESCAN is another suitable program for motif searching (Burge and Karlin, J. Mol. Biol. 268: 78–94, 1997), and information on Version 1.0 is available at the following website: http://gnomic.stanford.edu/GENESCANW.html. As used herein, "a target structural motif" or "target motif" refers any rationally selected sequence or combination of sequences in which the sequence(s) are chosen based on a three-dimensional configuration that is formed upon the folding of the target motif. There are a variety of target motifs known to those of skill in the art. Protein target motifs include, but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs that are implemented on the computer-based system to compare a target sequence or target structural motif with the sequence information stored within the data storage means. Search means are used to identify fragments or regions of the sequences of the present invention that match a particular target sequence or target motif. Multiple sequences can also be compared in order to identify common regions or motifs that may be responsible for specific functions. For example, cis elements or sequence domains that confer a specific expression profile can be identified when multiple promoter regions of similar classes of promoters are aligned and analyzed by certain software packages.

The present invention further provides systems, particularly computer-based systems, which contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any one of the available computer-based systems are suitable for use in the present invention.

SEQ ID NOS: 4–79 are primers designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51: 263, 1986; Erlich et al., European Patent Appln. EP50,424, EP84,796, EP258,017, EP 237,362; 201,184, U.S. Pat. Nos. 4,683,202, 4,582,788, and 4,683,194). A number of PCR amplification methods are known to those of skill in the art and are used to identify nucleic acid sequences adjacent to a known sequence. For example, inverse PCR (IPCR) methods to amplify unknown DNA sequences adjacent to a core region of known sequence have been described. Other methods are also available such as capture PCR (Lagerstrom et al., PCR Methods Applic. 1: 111, 1991), and walking PCR (Parker et al., Nucleic Acids Res 19: 3055, 1991). A number of manufacturers have also developed kits based on modifications of these methods for the purposes of identifying sequences of interest. Technical advances including improvements in primer and adaptor design, improvements in the polymerase enzyme, and thermocycler capabilities have facilitated quicker, more efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo Alto, Calif.). In brief, the purified genomic DNA is subjected to a restriction enzyme digest that produces genomic DNA fragments with ends that are ligated with GenomeWalker™ adaptors. GenomeWalker™ primers are used along with gene specific primers in two consecutive PCR reactions (primary and nested PCR reactions) to produce PCR products containing the 5' regulatory sequences that are subsequently cloned and sequenced.

In addition to their use in modulating gene expression, the promoter sequences of the present invention also have utility as probes or primers in nucleic acid hybridization experiments. The nucleic acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., at 9.52–9.55 and 9.47–9.52, 9.56–9.58, 1989; Kanehisa, Nucl. Acids Res. 12: 203–213, 1984; Wetmur and Davidson, J. Mol. Biol. 31: 349–370, 1968). Appropriate stringency conditions that promote DNA hybridization are, for example, 6.0× sodium chloride/sodium citrate (SSC) at about 45° C., followed by a wash of 2.0×SSC at 50° C., and they are known to those skilled in the art or can be found in laboratory manuals including but not limited to Current Protocols in Molecular Biology, John Wiley & Sons, N.Y., 1989, 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSS, 0.5% SDS, 5× Denhardt's, 100 µg/mL nonspecific DNA (e.g., sonicated salmon sperm DNA) with washing at 0.5×SSS, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well known to those of skill in the art. Thus depending on the application envisioned, one will desire to employ varying hybridization conditions to achieve varying degrees of selectivity of probe towards target sequence and the method of choice will depend on the desired results.

The nucleic acid sequences in SEQ ID NOS: 80–111, and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" if they can hybridize to one another with sufficient stability to permit them to remain annealed to one another under conventional "high stringency" conditions. Conventional stringency conditions are described by Sambrook et al. (*Molecular Cloning, A Laboratory Manual*, $2^{nd}$ Ed., Cold Spring Harbor Press, Cold Spring Harbor, N.Y., 1989), and by Haymes et al. (*Nucleic Acid Hybridization, A Practical Approach*, IRL Press, Washington, D.C., 1985).

In a preferred embodiment, the nucleic acid sequences SEQ ID NOS: 80–111 or a fragment, region, cis element, or oligomer of these sequences may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation that can be supplied by commercial vendors.

Of course, nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR™ (polymerase chain reaction) technology or by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein is a portion of the nucleic acid that is less than full-length. For example, for the present invention any length of nucleotide sequence that is less than the disclosed nucleotide sequences of SEQ ID NOS: 80–111 is considered to be a fragment. A fragment can also comprise at least a minimum length capable of hybridizing specifically with a native nucleic acid under stringent hybridization conditions as defined above. The length of such a minimal fragment is preferably at least 8 nucleotides, more preferably 15 nucleotides, even more preferably at least 20 nucleotides, and most preferably at least 30 nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described (see Sambrook et al., 1989; Ausubel et al., 1992, and Innis et al., 1990). PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOS: 80–111 may be modified or altered to enhance their control characteristics. One preferred method of alteration of a nucleic acid sequence is to use PCR to modify selected nucleotides or regions of sequences. These methods are known to those skilled in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOS: 80–111 include any length of said nucleotide sequences that are capable of regulating an operably linked DNA sequence. For example, the sequences as disclosed in SEQ ID NOS: 80–111 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues. Consequently, any sequence fragments, portions, or regions of the disclosed sequences of SEQ ID NOS: 80–111 can be used as regulatory sequences including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked for example, by placing such a fragment upstream of a minimal promoter. A "minimal promoter" or "basal promoter" refers to a piece of DNA fragment of a promoter that is capable of recruiting and binding the basal transcription machinery. A minimal promoter responds to transcriptional activator sequences. A minimal promoter may be combined with any fragment of a promoter of the present invention to form a chimeric or hybrid promoter so that the activity of the promoter fragment of the present invention may be tested. A "CaMV minimal promoter" is a fragment of the CaMV promoter that is isolated from the cauliflower mosaic virus (CaMV). A minimal CaMV 35S promoter is a good example that may be used in the present invention, which is capable of expressing in most plant tissues. One example of the basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOS: 80–111 or fragments, variants or derivatives thereof are incorporated into an expression vector cassette that includes the promoter regions of the present invention operably linked to a genetic component such as a selectable, screenable, or scorable marker gene. The disclosed nucleic acid sequences of the present invention are preferably operably linked to a genetic component such as a nucleic acid that confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In a preferred embodiment, one genetic component produces a product that serves as a selection device and functions in a regenerable plant tissue to produce a compound that would confer upon the plant tissue resistance to an otherwise toxic compound. Genes of interest for use as a selectable, screenable, or scorable marker would include but are not limited to GUS (coding sequence for beta-glucuronidase), GFP (coding sequence for green fluorescent protein), LUX (coding gene for luciferase), antibiotic resistance marker genes, or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin), methotrexate (and trimethoprim), chloramphenicol and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil (Cell Culture and Somatic Cell Genetics of Plants, Vols. I–III, Laboratory Procedures and Their Applications Academic Press, New York, 1984). Particularly preferred selectable marker genes for use in the present invention would include genes that confer resistance to compounds such as antibiotics like kanamycin and herbicides like glyphosate (Della-Cioppa et al., Bio/Technology 5(6), 1987; U.S. Pat. Nos. 5,463,175 and 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989. In a preferred embodiment, the host cell is a plant cell. A number of vectors suitable for stable transfection of plant cells or for the establishment of transgenic plants have been described in, e.g., Pouwels et al. (Cloning Vectors: A Laboratory Manual, 1985, supp. 1987); Weissbach and Weissbach (Methods for Plant Molecular Biology, Academic Press, 1989); Gelvin et al. (Plant Molecular Biology Manual, Kluwer Academic Publishers, 1990); and Croy (Plant Molecular Biology LabFax, BIOS Scientific Publishers, 1993). Plant expression vectors can include, for example, one or more cloned plant genes under the transcriptional control of 5' and 3' regulatory sequences. They can also include a selectable marker as described to select for host cells containing the expression vector. Such plant expression vectors also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and a polyadenylation signal. Other sequences of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NOS: 80–111, an operably linked transcribable sequence, and a transcription termination sequence. Other regulatory sequences envisioned as genetic components in an expression vector include, but is not limited to, non-translated leader sequence that can be coupled with the promoter. Plant expression vectors also can comprise additional sequences including but not limited to restriction enzyme sites that are useful for cloning purposes.

A number of promoters have utility for plant gene expression for any gene of interest including but not limited to selectable markers, scorable markers, genes for pest tolerance, disease tolerance, nutritional enhancements and any other gene that confers a desirable trait or characteristic. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988); the octopine synthase promoter (Fromm et al., Plant Cell 1:977, 1989); and the figwort mosaic virus (FMV) promoter as described in U.S. Pat. No. 5,378,619.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunl, Siebertz et al., Plant Cell 1:961, 1989); or (5) chemicals such as methyl jasmonate, salicylic acid, or safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989).

The promoters of the present invention are plant promoters that are capable of transcribing operably linked DNA sequences in male reproductive tissues and can be operably linked to any gene of interest in an expression vector.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84: 744, 1987; An et al., Plant Cell 1: 115, 1989), e.g., a 3' terminator region to increase mRNA stability of the mRNA, such as the PI-II terminator region of potato or the octopine or nopaline synthase 3' terminator regions. Five-end non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865). These additional upstream and downstream regulatory sequences may be derived from a source that is native or heterologous with respect to the other elements present on the expression vector.

The promoter sequences of the present invention are used to control gene expression in plant cells. The disclosed promoter sequences are genetic components that are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as a B.t., pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, fertilizer, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9: 207,1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene that produces a protein or mRNA that expresses a phenotype or morphology change of interest is useful for the practice of the present invention.

In addition to regulatory elements or sequences located upstream (5') or within a DNA sequence, there are downstream (3') sequences that affect gene expression and thus the term regulatory sequence as used herein refers to any nucleotide sequence located upstream, within, or downstream to a DNA sequence that controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences that activate, enhance or define the strength and/or specificity of the promoter (Atchison, Ann. Rev. Cell Biol. 4:127, 1988). T-DNA genes, for example, contain "TATA" boxes defining the site of transcription initiation and other upstream elements located upstream of the transcription initiation site modulate transcription levels (Gelvin, In: Transgenic Plants, Kung and Us, eds, San Diego: Academic Press, pp. 49–87, 1988). Chimeric promoter combined a trimer of the octopine synthase (ocs) activator to the mannopine synthase (mas) activator plus promoter and reported an increase in expression of a reporter gene (Min Ni et al., The Plant Journal 7:

661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. Nos. 5,110,732 and 5,097,025). Those of skill in the art are familiar with the standard resource materials that describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Maliga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

The promoter sequences of the present invention may be incorporated into an expression vector using screenable or scorable markers as described and tested in transient analyses that provide an indication of gene expression in stable plant systems. Methods for testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12: 612. 1993, electroporation of leaf protoplasts of wheat (Sethi et al., J. Crop Sci. 52: 152, 1983; electroporation of protoplast prepared from corn tissue (Sheen, The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene or a GFP gene. The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the 5' regulatory sequences of the present invention are directly incorporated into suitable plant transformation expression vectors comprising the 5' regulatory sequences operatively linked to a transcribable DNA sequence interest, transformed into plants and the stably transformed plants and progeny thereof analyzed for the desired expression profile conferred by the 5' regulatory sequences.

Those of skill in the art are aware of the vectors suitable for plant transformation. Suitable vectors would include but are not limited to disarmed Ti-plasmids for *Agrobacterium*-mediated methods. These vectors can contain a resistance marker, 1–2 T-DNA borders, and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains C58, LBA4404, EHA101 and EHA105. Particularly preferred strains are *Agrobacterium tumefaciens* strains. Other DNA delivery systems for plant transformation are also known to those of skill in the art and include, but are not limited to, particle bombardment of selected plant tissues.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. Nos. 5,004,863, 5,159,135 and 5,518,908, WO 97/43430), soybean (U.S. Pat. Nos. 5,569,834 and 5,416, 011; McCabe et al., Bio/Technology, 6:923, 1988; Christou et al., Plant Physiol., 87: 671, 1988); Brassica (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes et al., Science, 240: 204, 1988; Gordon-Kamm et al., Plant Cell, 2: 603, 1990; Fromm et al., Bio/Technology, 8: 833, 1990; Koziel et al., Bio/Technology, 11: 194, 1993); oats (*Avena sativa*; Somers et al., Bio/Technology, 10: 1589, 1992); orchardgrass (*Dactylis glomerata*; Horn et al., Plant Cell Rep., 7: 469, 1988); rice (*Oryza sativa*, including indica and japonica varieties, Toriyama et al., Biotechnology, 6: 10, 1988; Zhang et al., Plant Cell Rep., 7: 379, 1988; Luo and Wu, Plant Mol. Biol. Rep., 6: 165, 1988; Zhang and Wu, Theor. Appl. Genet. 76: 835, 1988; Christou et al., Bio/Technology, 9: 957, 1991); sorghum (*Sorghum bicolor*; Casas et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks et al., Plant Physiol., 102: 1077, 1993; Becker et al., Plant, J. 5: 299, 1994), and alfalfa (Masoud and Wu, Transgen. Res. 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

All publications and patents mentioned in this specification are herein incorporated by reference by their whole entireties as if each individual publication or patent is specially and individually stated to be incorporated by reference by its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Plant Material, DNA Isolation and Library Construction

The target cDNA libraries included six tassel libraries. The background cDNA libraries included cDNA libraries prepared from leaf, root, embryo, callus, shoot, seedling, endosperm, culm, ear and silks.

Plant Growth Conditions

Seeds are planted at a depth of about 3 cm in soil into 2"–3" pots containing Metro 200 growing medium and transplanted into larger 10" pots containing the same soil after 2–3 weeks. Plants are fertilized as needed. A total of about 900 mg Fe is added to each pot. Corn plants are grown in the greenhouse in 15 hr day/9 hr night cycles. The daytime temperature is 26.7° C. and the night temperature is 21.1° C. 1000 W sodium vapor lamps are provided for lighting.

Tissue Isolation

The corn immature tassel cDNA library (SATMON001) is generated using maize (B73, Illinois Foundation Seeds, Champaign, Ill. U.S.A). The corn plant is at the V6 plant developmental stage. The tassel is an immature tassel 2–3 cm in length. The immature tassel is frozen in liquid nitrogen and the harvested tissue is stored at −80° C. until the RNA is prepared.

The corn immature tassel cDNA library (SATMON021) is generated using maize (DK604, Dekalb Genetics, Dekalb Ill. U.S.A.). The corn plant is at the V8 plant developmental stage. The tassels, which are about 15–20 cm in length, are collected and frozen in liquid nitrogen. The harvested tissue is stored at −80° C. until the RNA is prepared.

The corn immature tassel cDNA library (SATMON024) containing tassel with glume, anthers, and pollen is generated using maize (DK604, Dekalb Genetics, Dekalb, Ill. U.S.A.). The corn plant is at the V9 plant developmental stage. The tassel is at the rapidly developing stage, and a tassel about 37 cm along with the glume, anthers, and pollen are collected and frozen in liquid nitrogen. The harvested tissue is stored at −80° C. until the RNA is prepared.

The corn pollen library (Lib148Mon) is generated using maize. The corn plant is shedding pollen. Pollen is collected by shaking the tassel in a paper bag. The pollen is collected and frozen in liquid nitrogen. The harvested tissue is stored at −80° C. until the RNA is prepared.

The corn immature anther library (LIB3066MON) is generated using maize. The anthers are dissected away from the other tissues of the florets using forceps. The anthers are collected and frozen in liquid nitrogen. The harvested tissue is stored at −80° C. until the RNA is prepared.

The corn germinating pollen on silk library (LIB3068MON) is generated using maize. After pollinating the silks, the pollen and silk tissue is harvested and frozen in liquid nitrogen. The harvested tissue is stored at −80° C. until the RNA is prepared.

The RNA is purified using Trizol reagent available from Life Technologies (Gaithersburg, Md.) essentially as recommended by the manufacturer. Poly A+RNA (mRNA) is purified using magnetic oligo dT beads essentially as recommended by the manufacturer (Dynabeads, Dynal Corporation, Lake Success, N.Y.). Two modifications to the Trizol protocol include centrifuging the ground tissue samples at 12,000×g for 10 minutes at 4° C. after the addition of Trizol to remove insoluble material, and precipitating the RNA with 0.25 mL isopropanol and 0.25 mL 0.8M NaCl per 1.0 mL Trizol used. All the samples are precipitated with 0.1 volume of 3M NaOAc and 3.0 volumes of ethanol. RNAs are resuspended in distilled water at a concentration of 2 µg/µL. The RNAs are treated for 10 minutes at room temperature with RNase free DNase (BMB, Indianapolis, Ind.) and samples are extracted with phenol/chloroform and isopropanol precipitated as described, and resuspended in distilled water at a concentration of 1 µg/µL.

Construction of cDNA libraries is well known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.).

After cDNA synthesis, the samples are diluted with one volume of water, and one microliter is used for each tissue-specificity PCR assay. Corn cDNAs are synthesized for tissue specificity testing methods well known in the art include leaf, root, rachus, early anther, kernals from 6 cm ear, kernals from 4 cm ears, silk, glumme/lemmalpalea, mature anther and pollen, meristem, microspores, culm, tassel, ear, and husk.

Example 2

Promoter Lead Identification

The database of EST sequences derived from the cDNA libraries prepared from various corn tissues is used to identify the genes with the correct expression profile from which promoter candidates can be isolated for expression of operably linked DNA sequences in male reproductive tissues. The sequences are also used as query sequences against GenBank databases that contain previously identified and annotated sequences and searched for regions of homology using BLAST programs. The selection of expressed sequence tags (ESTs) for subsequent promoter isolation is reflective of the presence of one or more sequences among the representative ESTs from a random sampling of an individual cDNA library or collection of cDNA libraries. To identify regulatory sequences that regulate the expression of transcripts in the target tissues of interest from EST sequences in the database, a subsetting function is done, requesting ESTs found in target libraries such as the three tassel libraries and EST clones in all other libraries are subtracted. The background or non-target libraries included the following: SATMON013 (corn meristem), SATMON020 (corn callus), SATMON022 (corn immature ear), SATMON023 (corn ear, growing silks), SATMON025 (corn regenerating callus), SATMON004 (corn leaf), SATMON009 (corn leaf, V8 stage), SATMON011 (corn leaf, undeveloped), SATMON016 (corn sheath), SATMON026 (corn leaf), SATMON027 (corn leaf, water stressed 6 days), SATMON031 (corn leaf V4 stage), SATMON01 (corn leaf normalize), SATMON003 (corn root), SATMON007 (corn primary root), SATMON010 (corn root V8 stage), SATMON028 (corn root, water stressed 6 days), SATMON030 (corn root V4 stage), SATMOM05 (corn root, normalize), SATMON014 (corn endosperm, 14 days after pollination), SATMON017 (corn embryo, 21 days after pollination), SATMON033 (corn embryo, 13 days after pollination), SATMON036 (corn endosperm 22 days after pollination), SATMONN04 (corn embryo, 21-DAP, normalized), SATMONN06 (corn embryo, 21-DAP, normalized), SATMON008 (corn primary shoot), SATMON012 (corn seedling, 2 days post-germination), SATMON019 (corn culm), SATMON029 (corn seedling, etiolated 4 days), and SATMON034 (corn seedling, cold stressed). The cDNA clones identified from the subsetting are candidates for tissue-enhanced/specific genes and are further pursued. Rt-PCR reactions are performed for each of the leads to determine if a male-specific/enhanced pattern of expression is observed. The EST sequences that are detectable predominantly in male tissues are used to isolate the tissue enhanced/specific promoters.

Table 1 provides background clone ID (EST) information and GenBank identifier (gi) information for the ESTs used for subsequent isolation of the promoter sequences of SEQ ID NOS: 80–111. The promoter leads are obtained from the SATMON024, LIB148MON, and LIB3066MON librar sources as described above. Sequence annotation is listed for the clone IDs based on a GenBank BLAST search with a p-value cut-off of $10^{-8}$. The information is subject to change as new sequences are submitted to the sequence databases.

TABLE 1

| Promoter Summary | | |
|---|---|---|
| SEQ ID NO | Clone ID | GenBank Identifier (gi) |
| 80 | 700352709 | none |
| 81 | 700354820 | g1914844 |
| 82 | 700356542 | g3297808 |
| 83 | 700382670 | none |
| 84 | 700383111 | g3646451 |
| 85 | L1481529 | none |
| 86 | L1482113-1 | g255568 |
| 87 | L1482113-2 | |
| 88 | L1482113-3 | |
| 87 | L1482830 | g2281085 |
| 90 | L1482865 | none |
| 91 | L1483194 | g308905 |
| 92 | L1483239 | none |
| 93 | L1484055 | none |
| 94 | L1484762 | g288611 |
| 95 | L1485873 | g19902 |
| 96 | L30663465 | none |
| 97 | L30664420 | g2695928 |
| 98 | L30665422 | g288611 |
| 99 | L1486301 | g2651297 |
| 100 | 700353208 | none |
| 101 | L30683230 | g1402878 |
| 102 | L1482016 | g405534 |
| 103 | L1482835 | g1333847 |
| 104 | 700352780 | g1890351 |
| 105 | 700382279 | g2098713 |
| 106 | 700356814 | g293901 |
| 107 | 700018036 | g22644 |
| 108 | L1482865 | none |
| 109 | L1484055 | none |
| 110 | L1485873 | g19902 |
| 111 | L30663465 | none |

Example 3

Genomic Library Construction, PCR Amplification and Promoter Isolation

A number of methods are known to those skilled in the art for genomic library preparation. For genomic libraries of the present invention, corn DNA (Maize hybrid Fr27 X FrMo17) is isolated by a CsCl purification protocol according to Ausubel et al. (1992) or by a CTAB purification method (Rogers and Bendich, Plant Mol. Biol., 5:69, 1988). Reagents are available commercially (see, for example Sigma Chemical Co., St. Louis, Mo.). The libraries are prepared according to manufacturer instructions (GENOME WALKER, a trademark of CLONTECH Laboratories, Inc, Palo Alto, Calif.). In separate reactions, genomic DNA is subjected to restriction enzyme digestion overnight at 37° C. with the following blunt-end endonuleases: EcoRV, ScaI, DraL PvuII, or StuI (CLONTECH Laboratories, Inc., Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors Taq polymerase used is Amplitaq Gold™ or Expand HiFidelity (Boehringer Mannheim) available through Perkin-Elmer Biosystems (Branchbury, N.J.). A number of temperature cycling instruments and reagent kits are commercially available for performing PCR experiments and include those available from PE Biosystems (Foster City, Calif.), Stratagene (La Jolla, Calif.), and MJ Research Inc. (Watertown, Mass.). Following the primary PCR reaction, an aliquot is taken (10–15 µL) for agarose gel analysis. Isolation of each unknown sequence required amplification from 5 sub-genomic libraries and a negative control (without DNA).

The PCR components and conditions generally used are outlined below:

Primary PCR

| Component | Amount/Volume required |
|---|---|
| Sub-library aliquot | 1 µL |
| Gene-specific primer 1 | 1 µL (100 pmol) |
| GenomeWalker ™ Adaptor primer 1 (AP1) | 1 µL |
| dNTP mix (10 mM of each dNTP) | 1 µL |
| DMSO | 2.5 µL (or 2–5% final concentration) |
| 10X PCR buffer (containing MgCl$_2$) | 5 µL (final concentration of 1X) |
| Amplitaq Gold ™ or Expand HiFidelity | 0.5 µL |
| Distilled Water | For final reaction volume of 50 µL |
| Reaction Conditions for Primary PCR: | |
| | |
| A. 1 minutes at 95° C | |
| B. 94° C. for 2 seconds, 70° C. for 3 minutes; repeat 94° C./70° C. cycling for total of 7 times | |
| C. 94° C. for 2 seconds, 65° C. for 3 minutes; repeat 94° C./65° C. cycling for total of 36 times | |
| D. 65° C. for 4 minutes as a final extension | |
| E. 10° C for an extended incubation | |
| NESTED PCR (secondary PCR reaction) | |
| | |
| 1:50 dilution of the primary PCR reaction | 1 µL |
| Gene-specific primer 2 | 1 µL (100 pmol) |
| GenomeWalker ™ Adaptor primer 2 or 3 (AP2 or AP3)) | 1 µL |
| dNTP mix (10 mM of each dNTP) | 1 µL |
| DMSO | 2.5 µL |
| 10X PCR buffer (containing MgCl$_2$) | 5 µL (final concentration of 1X) |
| Amplitaq Gold ™ | 0.5 µL |
| Distilled water | to final reaction volume of 50 µL |
| Reaction Conditions for Nested PCR: | |
| | |
| A. 1 minutes at 95° C. | |
| B. 94° C. for 2 seconds, 70° C. for 3 minutes; repeat 94° C./70° C. cycling for total of 5 times | |
| C. 94° C. for 2 seconds, 65° C. for 3 minutes; repeat 94° C./65° C. cycling for total of 24 times | |
| D. 65° C. for 4 minutes as a final extension | |
| E. 10° C. for an extended incubation | | and ligation of the resulting DNA fragments to adaptors are done according to manufacturer protocol. The GenomeWalker™ sublibraries are aliquoted and stored at −20° C.

Genomic DNA ligated to the GenomeWalker™ adaptor (above) is subjected to a primary round of PCR amplification with gene-specific primer 1 (GSP1) and a primer that anneals to the Adaptor sequence, adaptor primer 1 (AP1) (SEQ ID NO: 1). A diluted (1:50) aliquot of the primary PCR reaction is used as the input DNA for a nested round of PCR amplification with gene-specific primer 2 (GSP2) and adaptor primer 2 (AP2) (SEQ ID NO: 2), or adaptor primer 3 (AP3) (SEQ ID NO: 3). The annealing temperatures of the GenomeWalker™ primary primer (AP1) and nested primer (AP2) are 59° C. and 71° C., respectively. Generally, gene specific primers are designed to have the following characteristics: 26–30 nucleotides in length, GC content of 40–60% with resulting temperatures for most of the gene specific primers in the high 60° C. range or about 70° C. The For RT-PCR the corn inbred line H99 is used and the generic PCR reaction conditions are outlined below:
1µL cDNA
5 µL 10×BMB PCR reaction buffer (supplied with taq DNA polymerase)
1 µL 10 mM dNTPs
1 µL 10 uM primer 1
1 µL 10 uM primer 2
0.5 µL taq DNA polymerase (BMB, Indianapolis, Ind.)
40.5 µL H$_2$O
1 µL DMSO (optional)

3a. 700352709 Clone ID Analysis and Promoter Isolation

For the isolation of the clone ID 700352709 promoter, gene specific primer SEQ ID NO: 4 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 μL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 μL of a 1:5 dilution of the primary reaction is used with gene specific primer SEQ ID NO: 5 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis. A band of approximately 590 bp is cut out, purified using the Qiaquick gel extraction kit (Qiagen, Valencia, Calif. cat # 28704) and eluted with 30 μL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter sequence for clone ID 700352709 is SEQ ID NO: 80.

3b. 700353208 Clone ID Analysis and Promoter Isolation

For the isolation of the clone ID 700353208 promoter, gene specific primer SEQ ID NO: 6 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 μL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler using the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 μL of the primary reaction is used with gene specific primer SEQ ID NO: 7 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler using the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and the promoter-containing fragment of approximately 2,000 bp is cut out, purified using the Qiaquick gel extraction kit (Qiagen, Valencia, Calif. cat # 28704) and eluted with 30 μL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter sequence for clone ID 700353208 is SEQ ID NO: 100.

To obtain a promoter fragment upstream of the translational start codon, 1 μL of the isolated DNA is amplified under standard GenomeWalker™ PCR conditions using Expand Hi Fidelity DNA Polymerase (BMB, Indianapolis, INd.) with the supplied buffer #2 in combination with primers SEQ ID NO: 75 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter sequence for clone ID 700353208 is SEQ ID NO: 100.

3c. 700354820 Clone ID Analysis and Promoter Isolation

For the isolation of the clone ID 700354820 promoter, gene specific primer SEQ ID NO: 8 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 μL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 72 C 3 min, and 35 cycles 94 C 4 seconds, 68 C 3 minutes. For the nested, secondary PCR reaction, 1 μL of a 1:2 dilution of the primary reaction is used with gene specific primer SEQ ID NO: 9 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 4 seconds, 72 C 3 minutes, and 25 cycles of 94 C 4 seconds and 67 C 3 minutes.

Twenty five microliter of the secondary PCR reaction is analyzed by agarose gel electrophoresis and two promoter-containing fragments of approximately 500 bp and 700 bp are cut out, purified using the Qiaquick gel extraction kit (Qiagen, Valencia, Calif. cat # 28704) and eluted with 30 μL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter sequence is SEQ ID NO: 81.

3d. 700356542 Clone ID Analysis and Promoter Isolation

For the isolation of the clone ID 700356542 promoter, gene specific primer SEQ ID NO: 10 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 μL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 72 C 3 min, and 35 cycles 94 C 4 seconds, 68 C 3 minutes. For the nested, secondary PCR reaction, 1 µL of a 1:2 dilution of the primary reaction is used with gene specific primer SEQ ID NO: 11 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 4 seconds, 72 C 3 minutes, and 25 cycles of 94 C 4 seconds and 67 C 3 minutes.

Twenty five microliter of the secondary PCR reaction is analyzed by agarose gel electrophoresis and four promoter-containing fragments of approximately 670 bp, 1,000 bp, and 1,500 bp, are cut out, purified using the Qiaquick gel extraction kit (Qiagen, Valencia, Calif. cat # 28704) and eluted with 30 µL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

To obtain a promoter fragment upstream of the translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 76 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter fragment for clone ID 700356542 is SEQ ID NO: 82.

3e. 700382670 Clone ID Analysis and Promoter Isolation

For the isolation of the clone ID 700382670 promoter, gene specific primer SEQ ID NO: 12 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 13 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and the promoter-containing fragment of approximately 900 bp is cut out, purified using the Qiaquick gel extraction kit (Qiagen, Valencia, Calif. cat # 28704) and eluted with 30 µL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center To obtain a promoter fragment upstream of the translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 14 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID 700382670 is SEQ ID NO: 83.

3f. 700383111 KIAA0398 Clone ID Analysis and Promoter Isolation

For the isolation of the clone ID 700383111 promoter, gene specific primer SEQ ID NO: 15 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 16 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in seconds, 72 C 3 minutes, and 20 cycles of 94 C 5 seconds and 67 C 3 minutes.

Twenty five microliter of the secondary PCR reaction is analyzed by agarose gel electrophoresis and the promoter-containing fragment of approximately 1,000 is cut out, purified using the Qiaquick gel extraction kit (Qiagen, Valencia, Calif. cat # 28704) and eluted with 30 µL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center To obtain a promoter fragment upstream of the translational start codon, 1 µL of the isolated DNA is amplified under standard GenomeWalker™ PCR conditions using Expand Hi Fidelity DNA Polymerase (BMB, Indianapolis, IN) with the supplied buffer #2 in combination with primers SEQ ID NO: 17 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID 700383111 is SEQ ID NO: 84.

3g. L1481529 Clone ID Analysis and Promoter Isolation

For the isolation of the clone ID L1481529 promoter, gene specific primer SEQ ID NO: 18 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 μL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 μL of a 1:5 dilution of the primary reaction is used with gene specific primer SEQ ID NO: 19 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and the promoter-containing fragment of approximately 855 bp is cut out, purified using the Qiaquick gel extraction kit (Qiagen, Valencia, Calif. cat # 28704) and eluted with 30 μL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center The promoter for clone ID L1481529 is SEQ ID NO: 85.

3h. L1482113 Clone ID Analysis and Promoter Isolation

For the isolation of the clone ID L1482113 promoter, gene specific primer SEQ ID NO: 20 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 μL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 5 cycles of 94 C 4 seconds, 72 C 3 min, and 35 cycles 94 C 4 seconds, 68 C 3 minutes. For the nested, secondary PCR reaction, 1 μL of the primary reaction is used with gene specific primer SEQ ID NO: 21 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and three promoter-containing fragments of approximately 690 bp, 620 bp, and 900 bp, respectively, are cut out, purified using the Qiaquick gel extraction kit (Qiagen, Valencia, Calif. cat # 28704) and eluted with 30 μL 10 mM Tris pH. 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. Sequence comparisons indicated that the promoter fragments are very similar, but not identical, thus, representing 3 different promoters. Based on blast analysis, predictions of the translation initiation start codon (ATG) are made.

To obtain a promoter fragment upstream of the translational start codon, 1 μL of the isolated DNA is amplified under standard GenomeWalker™ PCR conditions using Expand Hi Fidelity DNA Polymerase (BMB, Indianapolis, Ind.) with the supplied buffer #2. The smaller fragments were used in combination with primer SEQ ID NO: 78 and SEQ ID NO: 3 (AP3). The largest fragment is used in combination with primer SEQ ID NO: 79 (. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.The promoter fragments obtained using SEQ ID NO:78 are SEQ ID NOS: 86 and 87. The promoter fragment obtained using SEQ ID NO:79 is SEQ ID NO: 88.

3i. L1482830 Clone ID Analysis and Promoter Isolation

For the isolation of the clone ID L1482830 promoter, gene specific primer SEQ ID NO: 22 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 μL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 72 C 3 min, and 35 cycles 94 C 4 seconds, 68 C 3 minutes. For the nested, secondary PCR reaction, 1 μL of a 1:2 dilution of the primary reaction is used with gene specific primer SEQ ID NO: 23 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 4 seconds, 72 C 3 minutes, and 20 cycles of 94 C 4 seconds and 67 C 3 minutes.

Twenty five microliter of the secondary PCR reaction is analyzed by agarose gel electrophoresis and two promoter-containing fragments of approximately 500 bp and 600 bp, respectively, are cut out, purified using the Qiaquick gel extraction kit (Qiagen, Valencia, Calif. cat # 28704) and eluted with 30 μL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome SequencingCenter.

To obtain a promoter fragment upstream of the translational start codon, 1 μL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 77 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter for clone ID L1482830 is SEQ ID NO: 89.

3j. L1482865 Clone ID Analysis and Promoter Isolation

For the isolation of the clone ID L1482865 promoter, gene specific primer SEQ ID NO: 24 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 72 C 3 min, and 35 cycles 94 C 4 seconds, 68 C 3 minutes. For the nested, secondary PCR reaction, 1 µL of a 1:2 dilution of the primary reaction is used with gene specific primer SEQ ID NO: 25 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 4 seconds, 72 C 3 minutes, and 20 cycles of 94 C 4 seconds and 67 C 3 minutes.

Twenty five microliter of the secondary PCR reaction is analyzed by agarose gel electrophoresis and three promoter-containing fragments of approximately 800 bp, 1,000 bp and 1700 are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The larger promoter for clone ID L1482865 is SEQ ID NO: 90. The smaller promoter is SEQ ID NO: 108.

3k. L1483194 Clone ID Analysis and Promoter Isolation

For the isolation of the clone ID L1483194 promoter, gene specific primer SEQ ID NO: 26 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 5 cycles of 94 C 4 seconds, 72 C 3 min, and 35 cycles 94 C 4 seconds, 68 C 3 minutes. For the nested, secondary PCR reaction, 1 µL of the primary reaction is used with gene specific primer SEQ ID NO: 27 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and one promoter-containing fragments of approximately 850 bp is cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, CA, Cat. #12125) and sequenced by the Genome Sequencing Center The promoter for clone ID L1483194 is SEQ ID NO: 91.

3l. L1483239 Clone ID Analysis and Promoter Isolation

For the isolation of the clone ID L1483239 promoter, two sets of PCR reactions are performed using different genes specific primers. In the first reaction set, gene specific primer SEQ ID NO: 28 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 29 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and three promoter-containing fragment of approximately 700 bp, 700 bp, and 800 bp are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 30 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID L1483239 is SEQ ID NO: 92.

3m. L1484055 Clone ID Analysis and Promoter Isolation

For the isolation of the clone ID L1484055 promoter, gene specific primer SEQ ID NO: 31 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 µL of a 1:5 dilution of the primary reaction is used with gene specific primer SEQ ID NO: 32 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and two promoter-containing fragments of approximately 618 bp and 2500 bp are cut out, purified using the Qiaquick gel extraction kit (Qiagen, Valencia, Calif. cat #28704) and eluted with 30 µL 10 mM Tris pH 8.5. Five microliter of the purified band is ligated to 50 ng of pGEM-T-Easy vector (Promoga, Madison, Wis. Cat. # A1360). DNA from individual clones is isolated using the Qiagen Plasmid Mini kit (Qiagen, Valencia, Calif., Cat. #12125) and sequenced by the Genome Sequencing Center. The larger promoter sequence for clone ID L1484055 is SEQ ID NO: 93. The smaller promoter sequence is SEQ ID NO: 109.

3n. Clone ID Analysis and Promoter Isolation L1484762

For the isolation of the clone ID L1484762 promoter, two sets of PCR reactions are performed using different genes specific primers. In the first reaction set, gene specific primer SEQ ID NO: 33 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 34 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and four promoter-containing fragment of approximately 1000 bp, 1600 bp, and 1500 bp respectively, are cut out, purified using the Qiaquick gel extraction kit (Qiagen, Valencia, Calif. cat # 28704) and eluted with 30 µL 10 mM Tris pH. 8.5. 5 µL of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 35 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID L1484762 is SEQ ID NO: 94.

3o. L1485873 Clone ID Analysis and Promoter Isolation

For the isolation of the clone ID L1485873 promoter, gene specific primer SEQ ID NO: 36 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 5 cycles of 94 C 4 seconds, 72 C 3 min, and 35 cycles 94 C 4 seconds, 68 C 3 minutes. For the nested, secondary PCR reaction, 1 µL of the primary reaction is used with gene specific primer SEQ ID NO: 37 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and two promoter-containing fragments of approximately 660 bp and 960 are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The larger promoter fro clone ID L1485873 is SEQ ID NO: 95. The smaller promoter sequence is SEQ ID NO: 110.

3p. L1486301 Clone ID Analysis and Promoter Isolation

For the isolation of the clone ID L1486301 promoter, gene specific primer SEQ ID NO: 38 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler using the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 39 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler using the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and two promoter-containing fragments of approximately 800 bp and 1,700 bp are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 40 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID L1486301 is SEQ ID NO: 99.

3q. L30663465 Clone ID Analysis and Promoter Isolation

For the isolation of the clone ID L30663465 promoter, gene specific primer SEQ ID NO: 41 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 µL of a 1:5 dilution of the primary reaction is used with gene specific primer SEQ ID NO: 42 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and four promoter-containing fragments of approximately 3,000 bp, 1,000 bp, 945 bp, and 3,000 bp, are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The largest promoter from clone ID 30663465 is SEQ ID NO: 96. The ~1000 bp promoter sequence is SEQ ID NO: 111.

3r. L30664420 Clone ID Analysis and Promoter Isolation

For the isolation of the clone ID L30664420 promoter, gene specific primer SEQ ID NO: 43 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 µL of a 1:5 dilution of the primary reaction is used with gene specific primer SEQ ID NO: 44 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and the promoter-containing fragment of approximately 2,000 bp is cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter for clone ID L30664420 is SEQ ID NO: 97.

3s. L30665422 Clone ID Analysis and Promoter Isolation

For the isolation of the clone ID L30665422 promoter, gene specific primer SEQ ID NO: 45 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 2 µL of a 1:2 dilution of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler with a ramp time of 1 C/sec: 94 C 1 minute, 5 cycles of 94 C 4 seconds, 72 C 3 min, and 35 cycles 94 C 4 seconds, 68 C 3 minutes. For the nested, secondary PCR reaction, 1 µL of the primary reaction is used with gene specific primer SEQ ID NO: 46 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliter of the secondary PCR reaction is analyzed by agarose gel electrophoresis and four promoter-containing fragment of approximately 350 bp, 450 bp, 1000 bp, and 1700 are cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

Translation of the 3' promoter fragment sequences showed an open reading frame that showed similarity to the polygalacturonase family. From this data, a prediction is made as to the translation initiation codon. To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 47 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID L30665422 is SEQ ID NO: 98.

3t. L30683230 Clone ID Analysis and Promoter Isolation

For the isolation of the clone ID L30683230 promoter, gene specific primer SEQ ID NO: 48 is used in combination with adapter primer SEQ ID NO: 1 in a standard Genome Walker PCR reaction (see SOP) with the following conditions: Expand Hi Fidelity DNA Polymerase (BMB Indianapolis, Ind. Cat. #1759078) is used in conjunction with the supplied buffer #2, 1 µL of Genome Walker libraries made according to the manufacturer's protocol (Clontech, Palo Alto, Calif. cat # K1807-1) and made with maize genomic DNA (see SOP). The following cycling parameters are used in an MJR Tetrad thermocycler using the default ramp time: 94 C 1 minute, 7 cycles of 94 C 4 seconds, 70 C 3 min, and 33 cycles 94 C 4 seconds, 68 C 3 minutes. For the nested, secondary PCR reaction, 1 µL of the primary reaction is used with gene specific primer SEQ ID NO: 49 and adapter primer SEQ ID NO: 3 in a standard Genome Walker PCR reaction (see SOP) using Expand Hi Fidelity DNA Polymerase (BMB Indianapolis, Ind. Cat. #1759078) with the supplied buffer #2. The reactions are carried out under the following cycling conditions in an MJR Tetrad thermocycler using the default ramp time: 94 C 1 minute, 5 cycles of 94 C 5 seconds, 72 C 3 minutes, and 20 cycles of 94 C 5 seconds and 67 C 3 minutes.

Twenty five microliter of the secondary PCR reaction is analyzed by agarose gel electrophoresis and the promoter-containing fragment of approximately 600 bp is cut out, purified using the Qiaquick gel extraction kit (Qiagen, Valencia, Calif. cat # 28704) and eluted with 30 µL 10 mM Tris pH 8.5. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center.

To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO: 50 and SEQ ID NO: 3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The promoter of clone ID L30683230 is SEQ ID NO: 101.

3u. 700382279 Clone ID Analysis and Promoter Isolation

To determine the distribution of the clone ID 700382279 transcripts in corn, RT-PCR is performed using primers SEQ ID NO: 51 and SEQ ID NO: 52 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID 700382279 promoter, gene specific primer SEQ ID NO: 53 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 µL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 µL of a 1:50 dilution in water of the primary reaction is used in conjunction with primer SEQ ID NO: 54 and adapter primer SEQ ID NO: 2 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragments of approximately 1600 bp is cut out, purified using the Qiaquick gel extraction kit (Qiagen, Valencia, Calif. cat # 28704) and eluted with approximately 40 μL of double distillate water. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter of clone ID 700382279 is SEQ ID NO: 105.

3v. L1482835 Clone ID Analysis and Promoter Isolation

To determine the distribution of the clone ID L1482835 transcripts in corn, RT-PCR is performed using primers SEQ ID NO: 55 and SEQ ID NO: 56 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID L1482835 promoter, gene specific primer SEQ ID NO: 57 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 μL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 μL of a 1:50 dilution in water of the primary reaction is used in conjunction with primer SEQ ID NO: 58 and adapter primer SEQ ID NO: 3 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragments of approximately 1300 bp is cut out, purified using the Qiaquick gel extraction kit (Qiagen, Valencia, Calif. cat # 28704) and eluted with approximately 40 μL of double distillate water. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center The promoter for clone ID L1482835 is SEQ ID NO: 103.

3w. L1482016 Clone ID Analysis and Promoter Isolation

To determine the distribution of the clone ID L1482016 transcripts in corn, RT-PCR is performed using primers SEQ ID NO: 59 and SEQ ID NO: 60 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID L1482016 promoter, gene specific primer SEQ ID NO: 61 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 μL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 μL of a 1:50 dilution in water of the primary reaction is used in conjunction with primer SEQ ID NO: 62 and adapter primer SEQ ID NO: 3 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragments of approximately 400 bp called is cut out, purified using the Qiaquick gel extraction kit (Qiagen, Valencia, Calif. cat # 28704) and eluted with approximately 40 μL of double distillate water. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center The promoter to clone ID L1482016 is SEQ ID NO: 102.

3x. 700356814 Clone ID Analysis and Promoter Isolation

To determine the distribution of the clone ID 700356814 transcripts in corn, RT-PCR is performed using primers SEQ ID NO: 63 and SEQ ID NO: 64 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID 700356814 promoter, gene specific primer SEQ ID NO: 65 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 µL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 µL of a 1:50 dilution in water of the primary reaction is used in conjunction with primer SEQ ID NO: 66 and adapter primer SEQ ID NO: 3 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragment of approximately 1100 bp is cut out, purified using the Qiaquick gel extraction kit (Qiagen, Valencia, Calif. cat 700356814-1# 28704) and eluted with approximately 40 µL of double distillate water. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter for clone ID 700356814 is SEQ ID NO: 106.

3y. 700018036 Clone ID Analysis and Promoter Isolation

To determine the distribution of the clone ID 700018036 transcripts in corn, RT-PCR is performed using primers SEQ ID NO: 67 and SEQ ID NO: 68 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID 700018036 promoter, gene specific primer SEQ ID NO: 69 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 µL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 µL of a 1:50 dilution in water of the primary reaction is used in conjunction with primer SEQ ID NO: 70 and adapter primer SEQ ID NO: 3 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragments of approximately 2500 bp called is cut out, purified using the Qiaquick gel extraction kit (Qiagen, Valencia, Calif. cat # 28704) and eluted with approximately 40 µL of double distillate water. Five microliter of the purified band is ligated to 50 ng of pGEM-T-Easy vector (Promoga, Madison, Wis., Cat. # A1360). DNA from individual clones is isolated using the Qiagen Plasmid Mini kit (Qiagen, Valencia, Calif., Cat. #12125) and sequenced by the Genome Sequencing Center. The promoter to clone ID 700018036 is SEQ ID NO: 107.

3z. 700352780 Clone ID Analysis and Promoter Isolation

To determine the distribution of the clone ID 700352780 transcripts in corn, RT-PCR is performed using primers SEQ ID NO: 71 and SEQ ID NO: 72 following the RT-PCR protocol using cDNA derived from glume/lemma/palea, husk, culm, immature ears, leaf, microspores, anther, pollen, tassel, root, and silk. Taq DNA polymerase from BMB (Indianapolis, Ind. catalog #1435094) is used in combination with the supplied reaction buffer. Cycling parameters, using an MJR DNA engine programmed in the calculated mode, are as follows: 95 C for 1 minute, then 35 cycles of 95 C 15 seconds, 50 C for 30 seconds, 72 C for 30 seconds. Completed by 10 minutes at 72 C for final extension. Agarose gel electrophoresis confirmed a male specificity and/or male enhancement of the target clone.

For the isolation of the clone ID 700352780 promoter, gene specific primer SEQ ID NO: 73 is used in combination with adapter primer SEQ ID NO: 1 in a standard Genome Walker PCR reaction (see Standard Operation Procedure) with the following conditions: AccuTaq-LA DNA polymerase (Sigma, St.-Louis, Cat. # D-5553) is used in conjunction with the supplied buffer and 2% DMSO, 1 μL of Genome Walker libraries made according to the manufacturer's protocol (Clontech, Palo Alto, Calif. cat # K1807-1) and made with maize genomic DNA (see S.O.P.). The following cycling parameters are used in an MJR thermocycler using the default ramp time: 94 C 4 minute, 7 cycles of 94 C 2 seconds, 70 C 3 min, and 36 cycles 94 C 2 seconds, 67 C 3 minutes and then 67 C for 4 minutes.

For the nested, secondary PCR reaction, 1 μL of a 1:50 dilution in water of the primary reaction is used in conjunction with primer SEQ ID NO: 74 and adapter primer SEQ ID NO: 3 in a standard Genome Walker PCR reaction (see S.O.P.) using: AccuTaq-LA DNA polymerase (Sigma, St.-Louis, Cat. # D-5553) with the supplied buffer and 2% DMSO. The reactions are carried out under the following cycling conditions in an MJR thermocycler using the default ramp time: 94 C 1 minute, 5 cycles of 94 C 2 seconds, 72 C 3 minutes, and 25 cycles of 94 C 2 seconds and 65 C 3 minutes, followed by an additional extension at 65 C for 4 minutes.

Twenty five microliter of the secondary PCR reaction is analyzed by agarose gel electrophoresis and one promoter-containing fragments of approximately 2000 bp, is cut out, purified using the Qiaquick gel extraction kit (Qiagen, Valencia, Calif. cat # 28704) and eluted with approximately 40 μL of double distillate water. Five microliter of the purified band is ligated to 50 ng of pGEM-T-Easy vector (Promoga, Madison, Wis., Cat. # A1 360). DNA from individual clones is isolated using the Qiagen Plasmid Mini kit (Qiagen, Valencia, Calif., Cat. #12125) and sequenced by the Genome Sequencing Center. The promoter fragment for clone ID 700352780 is SEQ ID NO: 104.

Example 4

Promoter Isolation and Cloning

The DNA fragments resulting from the nested PCR amplification described above are isolated and gel purified. A 25 μL aliquot of the secondary PCR is run on an agarose gel. The DNA fragment of the secondary PCR product is purified from the agarose gel using the Qiagen Kit following the conditions suggested by the manufacturer. The purified DNA is ligated to pGEM-T Easy vector (pGEM-T Easy Vector System I, Promega Corp., Madison, Wis.) following the conditions recommended by the manufacturer. An aliquot of the ligation reaction is transformed into a suitable *E. coli* host such as DH10B and the cells plated on selection medium (for DH10B, 100 g/mL carbenicillin). Bacterial transformants are selected, grown in liquid culture, and the plasmid DNA isolated using a commercially available kit such as the Qiaprep Spin Miniprep Kit (Qiagen Corp., Valencia, Calif.). Purified plasmid containing the predicted insert size based on restriction enzyme analysis are sequenced using the dye terminator method in both directions using the M13 forward and reverse primers (Promega, Madison, Wis. Cat #'s Q5391 and Q5401, respectively). Restriction enzymes are available from a number of manufacturers (see, for example, Boehringer Mannheim (Indianapolis, Ind.). The 5' flanking regions containing the promoter sequences are determined and shown in SEQ ID NOS: 80–111. Engineering restriction sites for cloning into suitable vectors is done using standard molecular biology techniques known to those skilled in the art.

Example 5

Transient Analysis of Promoter Activity in Protoplasts and Microspores

For transient expression, promoter fragments are cloned into expression vectors such as pMON19469 shown in FIG. 1. Plasmid pMON19469 is an expression vector consisting of the following genetic components: P-e35S is the promoter for the 35S RNA from CaMV containing a duplication of the −90 to −300 region; HSP70 intron is the intervening sequence of the maize heat shock protein as described in U.S. Pat. Nos. 5,593,874 and 5,859,347; GUS: 1 is the coding region for beta-glucuronidase; nos 3' is the termination signal from the nopaline synthase gene; ori-M13 and ori-pUC are origins of replication; AMP is the coding region for ampicillin selection. If a translational start codon of a target promoter is identified, the fragment is cloned into pMON19469 in place of the P-e35S genetic element. If an AUG is not identified, the promoter fragment is cloned into an expression vector modified to enable translational fusions with a reporter gene such as β-glucuronidase (GUS) (Jefferson et al., EMBO J. 6: 3901, 1987) or green fluorescent protein (GFP) as described in Pang et al. (Plant Physiol. 112: 893, 1996).

The expression constructs are tested in a transient plant assay. A number of assays are available and known to those skilled in the art. Analysis of reporter genes in a protoplast system can be used to assess the activity of a regulatory element, such as a promoter operably linked to the reporter gene. A leaf protoplast isolation and electroporation protocol is followed essentially as described by Sheen (The Plant Cell 3: 225–245, 1991) with the following modifications: the seed used is FR27RHM X FRMo17RHM from Illinois Foundation Seeds. The seed is surface sterilized for 2 minutes in 95% ethanol, rinsed twice with sterile water, 30 minutes in 50% bleach (Clorox) plus 2 drops of Tween-20, three rinses in sterile water followed by a 5-minute soak in benlate/captan solution to prevent fungal growth. The seeds are germinated in phytotrays containing 100 ml ½ MS media (2.2 g/L MS salts, 0.25% gelrite), 7 seeds per phytotray. The seeds are grown 5 days at 26° C. in 16/8 hour day/night photoperiod and 7 days in the dark at 28° C. The second leaf from each plant is sliced longitudinally using Feather No. 11 surgical blades. Digestion time is two hours and 10 minutes in the light at 26° C. After digestion, the plates are swirled two times at 80–100 rpm for 20 seconds each and the protoplast/enzyme solution is pipetted through a 190 μm tissue collector. Protoplasts are counted using a hemacytometer counting only protoplasts that are intact and circular. Ten to fifty micrograms of DNA containing the vector of interest is added per cuvette. Final protoplast densities at electroporation range from $3 \times 10^6$/mL to $4.5 \times 10^6$/mL. Electroporations are performed in the light using Bio-Rad Gene pulser cuvettes (Bio-Rad Hercules, Calif.) with a 0.4 cm gap and a maximum volume of 0.8 mL at 125 μFarads capacitance and 260 volts. The protoplasts are incubated on ice after resuspension in electroporation buffer and are kept on ice in cuvettes until 10 minutes after electroporation. The protoplasts are kept at room temperature for ten minutes before adding 7 mL of protoplast growth medium. The protoplast culture medium has been described (Fromm et al., Methods in Enzymology 153: 351–366, 1987). Culture plates are layered with the growth medium and 1.5% SeaPlaque agarose (FMC BioProducts, Rockland, Me.) to prevent protoplast loss. Samples are cultured in the light at 26° C., 16/8 day/night cycle, until harvested for the assay (typically 18–22 hours after electroporation). Samples are pipetted from the petri plates to 15 mL centrifuge tubes and harvested by centrifugation at 800–1000 rpm. The supernatant is removed and samples are assayed immediately for the gene of interest. Samples can also be frozen for later analysis.

For analysis of promoter activity in a wheat protoplast system, the method for isolation and preparation of wheat protoplasts is performed as described by Zhou et al. (Plant Cell Reports 12: 612, 1993). The electroporation buffer used has been described (Li et al., 1995). The culture medium used is MS1 MSM (4.4 g Gibco MS salts/L, 1.25 ml Thiamine HCL (0.4 mg/mL), 1 mL 2,4-D (1 mg/mL), 20 g/L sucrose, 0.15 mL asparagine (15 mg/mL), 0.75 g $MgCl_2$. 109 g/L 0.6M mannitol, pH5.5. Mustang protoplasts are used for protoplast isolation about four days after subculture. Briefly, 8 g of wheat cell suspension is poured into a culture tube, the cells are allowed to settle. The medium is removed and remaining cells are resuspended with 40 mL enzyme solution, transferred to a petri plate, wrapped in foil, and incubated at 26° C. for 2 hours on a rotator at 40 rpm. The suspension is centrifuged at 200 g for 8 min., washed twice with centrifugation between each wash, resuspended in 10 mL wash solution and stored on ice. The number of protoplasts is determined and the volume adjusted to a final concentration of $4 \times 10^6$ protoplasts/ml. About 0.75 mL of protoplasts is added to each electroporation cuvette and up to about 50 µg plasmid DNA of the vector in 50 µL solution is added to the protoplasts. The electroporation conditions are 960µ Farads and 160 volts using a Bio-Rad Gene Pulser (Bio-Rad Laboratories, Hercules, Calif.). The samples remain on ice for 10 minutes prior to and during electroporation. After electroporation, the samples are left on ice for about 10 minutes and removed and allowed to warm to room temperature for 10 minutes. The electroporated cells are pipetted into MS1 WSM medium and incubated in the dark for 18–22 hours at 24° C. The cells are harvested by centrifugation at 200–250 g for 8 minutes and frozen on dry ice for subsequent analysis of expression of the gene of interest.

In another transient assay system, barley microspores are used. For this assay shoots are collected and spikes are removed from the sheath and placed in 15×100 mm plates. Fifteen microliter of 0.3 M ice-cold mannitol is added into each plate containing 10 spikes. The plates are sealed with parafilm and kept at 4° C. for 3–4 days. Pre-treated spikes are cut about 1–2 cm into a chilled blender cup (about 10 two-rowed spikes needed/plate). The spikes are covered with enough cold mannitol to create slurry and blended at low speed in a Waring blender for 6–10 seconds. The slurry is filtered through cheesecloth or a nylon membrane and the filtrate is filtered through a 100 µm mesh nylon membrane into a 50 mL centrifuge tube. The mixture is spun for 5 minutes at 900 rpm and the liquid is decanted and microspore pellet resuspended in 2 mL liquid FHG medium. The microspores are filtered through three layers of Whatman #2 filter paper into a filtering flask under vacuum. About 2 mL microspores are dropped on each filter set and the uppermost filter paper is transferred to solid medium (FHG+0.25 M mannitol+0.25 M sorbitol on a 15×100 mm plate). The plates are sealed with parafilm and incubated in the dark at 25° C. for 3–4 hours prior to particle bombardment. A number of methods of particle bombardment can be used (see, for example, Klein et al., Bio/Technology 6: 559, 1988; Christou, Particle Bombardment for Genetic Engineering of Plants, Academic Press, 1996). After bombardment, the plates are sealed and kept at 25° C. for 20–24 hours. 0.3 M mannitol solution is used to wash microspores from the filter paper and the microspores are collected by centrifugation and analyzed for expression of the gene of interest. The FHG medium recipe is as follows: Macroelements (mg/L) include, 1900 mg KNO, 165 mg $NH_4NO_3$, 170 mg $KH_2PO_4$, 370 mg $MgSO_4$ 7 $H_2O$, 440 mg $CaCl_2$ $2H_2O$; Microelements (mg/L) include 40 mg FeNa.EDTA, 22.3 mg $MnSO_4.5H_2O$, 6.2 mg $H_3BO_3$, 8.6 mg $ZnSO_4$, 0.025 $CuSO_4.5H_2O$, 0.25 mg $NaM004.2H_2O$.

Example 6

Transient Analysis of Promoter Activity in Wheat Reproductive Tissues

For analysis of promoter activity in wheat reproductive tissues such as wheat anthers and ovaries, constructs containing the potential promoter, the HSP70 intron and the GUS gene are bombarded into wheat anthers and ovaries from wheat spikes in which the boot is just beginning to open. One spike of anthers and ovaries is dissected per plate (1 liter plate media: 4.4 g MS salt, 40 g maltose, 40 g raffinose, 22.78 g mannitol, 1.95 g MES, 4 g phytagel at pH 5.8). 2.5 µg of each DNA sample (1 µg/µL) to be tested is precipitated with 12.5 µL tungsten, 5.0 µL 0.1M spermidine and 12.5 µL 1.0M calcium chloride for 40 minutes at room temperature. For gunpowder bombardments, 12.5 µL of the supernatant is removed and remainder of sample is sonicated before each shot. 2.5 µL of the DNA precipitant is bombarded per shot. For the helium gun bombardments, the precipitated DNA is spun down, washed with 70% EtOH, washed with 100% EtOH and resuspended in 40 µL 100% EtOH. Five microliter of the DNA is bombarded per plate. For either gun, each plate is shot twice, and two plates are assayed per DNA sample. After bombardment, the plates are incubated overnight at 24° C. in the dark. The next day the anther and ovaries are transferred to a GUS staining solution. To increase the penetration of the staining solution, the samples are put in a vacuum chamber for 10 minutes. Anthers and ovaries are incubated in the staining solution at 37° C. for 16–24 hours. The staining solution is replaced with 70% EtOH, and the tissues are stored at 4° C. Staining is strictly qualitative, either there is expression or not. The staining indicates nothing of the tissue specificity of the potential promoters in stable plates, because the wheat ovary is a very promiscuous tissue that allows any active promoter to be expressed in this transient system.

Example 7

Promoter Activity from Transient Assay Analysis

In general, transcriptional regulatory elements necessary for promoter activity are located within a few hundred bases of the transcriptional start site. In many plant promoters, regulatory elements sufficient for driving heterologous gene expression in a spatial and temporal pattern that mimics the expression of the endogenous gene are located within 1000 base pairs 5' of the transcriptional start site (i.e., AP3, pi, lat52, lat59). There are some genes, however, where transcriptional regulatory elements can be located kilobases away, 5' or 3' to the transcriptional start site.

The transient assay is a system well suited to determining if sufficient regulatory elements are present for transcription initiation. As described in Examples 5 and 6, a DNA fragment is operationally linked to a reporter gene of interest and that construct is "placed" (through particle bombardments, electroporation, etc) into cells, protoplasts or tissues. Expression of the reporter gene in the recipient cells indicates that enough regulatory sequences reside in the DNA fragment to initiate transcription. Thereby, the DNA fragment can be considered a promoter. The transient assay does not provide any data regarding the pattern of gene expression the promoter fragment would provide in vivo. A prediction of the promoter's activity can be made based on the pattern of the endogenous gene's activity, but the accuracy of this prediction is dependent on whether the promoter fragment contains all the necessary regulatory elements responsible for the proper expression of the endogenous gene.

A negative result in a transient assay does not necessarily indicate that a tested DNA fragment has no promoter activity. In addition to experimental error, some of the conditions that could result in a negative result are: 1. a translational start codon is located within the DNA fragment thereby blocking expression of the reporter gene; 2. the DNA fragment contains a transcriptional start site and a splice donor site, but lacks a splice acceptor site. Therefore, the reporter gene is not expressed because the message is not properly spliced; 3. transcription factors specific to the function of the promoter region may not be present in the tissues used for the transient assay; or 4. the level of transcription is below the limits of detection of the assay.

To test the DNA fragments contained in Example 3 for promoter activity, SEQ ID NOS: 80–85, 88–98, 100–103, 105, and 108–111 are assayed by particle bombardment of wheat reproductive tissue (see Example 9). As described in Examples 5, the experimental cassette used to test each putative promoter fragment contains the fragment operationally linked to the hsp70 intron and the GUS gene. The data is summarized in Table 2. The experiment for each construct is carried out at least 2 times. A construct containing the rice actin promoter promoter operationally linked to the hsp70 intron and GUS gene is used as a positive control and a no-DNA bombardment is used as a negative control.

7a. 700352709

SEQ ID NO: 80 is operably linked to the hsp70 intron and the GUS gene to generate the construct pMON48161. This construct is tested in the wheat reproductive tissue transient assay. GUS activity is detected at a level of expression much lower than seen with the rice actin promoter but greater than that seen with the no DNA bombardments indicating that SEQ ID NO: 80 has promoter activity.

7b. 700353208

SEQ ID NO: 100 is operably linked to the hsp70 intron and the GUS gene to generate the construct pMON53321. This construct is tested for promoter activity using the wheat reproductive tissue transient assay. GUS activity is not detected which could be due to any of the reasons described above.

7c. 700354820

SEQ ID NO: 81 is operably linked to the hsp70 intron and the GUS gene to generate the construct pMON48151. This construct is tested for promoter activity using the wheat reproductive tissue transient assay. GUS activity is detected at a level slightly below that seen with the rice actin promoter positive control indicating that SEQ ID NO: 81 has promoter activity.

7d. 700356542

SEQ ID NO: 82 is operably linked to the hsp70 intron and the GUS gene to generate the construct pMON48143. This construct is tested for promoter activity using the wheat reproductive tissue transient assay. GUS activity is not detected which could be due to any of the reasons described above.

7e. 700382670

SEQ ID NO: 83 is operably linked to the hsp70 intron and the GUS gene to generate the construct pMON53330. This construct is tested for promoter activity using the wheat reproductive tissue transient assay. GUS activity is not detected which could be due to any of the reasons described above.

7f. 700383111

SEQ ID NO: 84 is operably linked to the hsp70 intron and the GUS gene to generate the construct pMON53314. This construct is tested for promoter activity using the wheat reproductive tissue transient assay. GUS activity is not detected which could be due to any of the reasons described above.

7g. L1481529

SEQ ID NO: 85 is operably linked to the hsp70 intron and the GUS gene to generate the construct pMON48160. This construct is tested for promoter activity using the wheat reproductive tissue transient assay. GUS activity is detected at a level slightly below that seen with the 35S positive control indicating that SEQ ID NO: 85 has promoter activity.

7h. L1482113

SEQ ID NO: 88 is operably linked to the hsp70 intron and the GUS gene to generate the construct pMON48148. This construct is tested in the wheat reproductive tissue transient assay. GUS activity is detected at a level of expression much lower than seen with the rice actin promoter but greater than that seen with the no DNA bombardments indicating that SEQ ID NO: 88 has promoter activity.

7i. L1482830

SEQ ID NO: 89 is operably linked to the hsp70 intron and the GUS gene to generate the construct pMON48145. This construct is tested in the wheat reproductive tissue transient assay. GUS activity is detected at a level of expression much lower than seen with the rice actin promoter but greater than that seen with the no DNA bombardments indicating that SEQ ID NO: 89 has promoter activity.

7j. L1482865

SEQ ID NO: 108 is a smaller version of the putative promoter SEQ ID NO: 90. SEQ ID NO: 108 is operably linked to the hsp70 intron and the GUS gene to generate the construct pMON48146. SEQ ID NO: 90 is operably linked to the hsp70 intron and the GUS gene to generate the constructs pMON48150. Both the constructs are tested in the wheat reproductive tissue transient assay. GUS activity is not detected which could be due to any of the reasons described above.

7k. L1483194

SEQ ID NO: 91 is operably linked to the hsp70 intron and the GUS gene to generate the construct pMON48147. This construct is tested for promoter activity using the wheat reproductive tissue transient assay. GUS activity is not detected which could be due to any of the reasons described above.

7l. L1483239

SEQ ID NO: 92 is operably linked to the hsp70 intron and the GUS gene to generate the construct pMON53304. This construct is tested for promoter activity using the wheat reproductive tissue transient assay. GUS activity is not detected which could be due to any of the reasons described above.

7m. L1484055

SEQ ID NO: 109 is a smaller version of the putative promoter SEQ ID NO: 93. SEQ ID 109 is operably linked to the hsp70 intron and the GUS gene to generate the construct pMON48156. SEQ ID NO: 93 is operably linked to the hsp70 intron and the GUS gene to generate the constructs pMON48155. Both the constructs are tested in the wheat reproductive tissue transient assay. GUS activity is detected at a level slightly below that seen with the the rice actin promoter positive control indicating that SEQ ID NOS: 93 and 109 have promoter activity.

7n. L1484762

SEQ ID NO: 94 is operably linked to the hsp70 intron and the GUS gene to generate the construct pMON53302. This construct is tested in the wheat reproductive tissue transient assay. GUS activity is detected at a level of expression much lower than seen with the rice actin promoter but greater than that seen with the no DNA bombardments indicating that SEQ ID NO: 94 has promoter activity.

7o. L1485873

SEQ ID NO: 110 is a smaller version of the putative promoter SEQ ID NO: 95. SEQ ID NO: 110 is operably linked to the hsp70 intron and the GUS gene to generate the construct pMON48152. SEQ ID NO: 95 is operably linked to the hsp70 intron and the GUS gene to generate the constructs pMON48153. Both the constructs are tested in the wheat reproductive tissue transient assay. GUS activity is detected at a level slightly below that seen with the the rice actin promoter positive control indicating that SEQ ID NOS: 95 and 110 have promoter activity.

7p. L30663465

SEQ ID NO: 111 is a smaller version of the putative promoter SEQ ID NO: 96. SEQ ID NO: 111 is operably linked to the hsp70 intron and the GUS gene to generate the construct pMON48158. SEQ ID NO: 96 is operably linked to the hsp70 intron and the GUS gene to generate the constructs pMON48159. Both the constructs are tested in the wheat reproductive tissue transient assay. GUS activity is not detected which could be due to any of the reasons described above.

7q. L30664420

SEQ ID NO: 97 is operably linked to the hsp70 intron and the GUS gene to generate the construct pMON48157. This construct is tested in the wheat reproductive tissue transient assay. GUS activity is detected at a level of expression much lower than seen with the rice actin promoter but greater than that seen with the no DNA bombardments indicating that SEQ ID NO: 97 has promoter activity.

7r. L1482016

SEQ ID NO: 102 is operably linked to the hsp70 intron and the GUS gene to generate the construct pMON49340. This construct is tested in the wheat reproductive tissue transient assay. GUS activity is detected at a level of expression much lower than seen with the rice actin promoter but greater than that seen with the no DNA bombardments indicating that SEQ ID NO: 102 has promoter activity.

7s. L30665422

SEQ ID NO: 98 is operably linked to the hsp70 intron and the GUS gene to generate the construct pMON48149. This construct is tested in the wheat reproductive tissue transient assay. GUS activity is detected at a level of expression much lower than seen with the rice actin promoter but greater than that seen with the no DNA bombardments indicating that SEQ ID NO: 98 has promoter activity.

7t. L30683230

SEQ ID NO: 101 is operably linked to the hsp70 intron and the GUS gene to generate the construct pMON53316. This construct is tested in the wheat reproductive tissue transient assay. GUS activity is detected at a level of expression much lower than seen with the rice actin promoter but greater than that seen with the no DNA bombardments indicating that SEQ ID NO: 101 has promoter activity.

7u. 700382279

SEQ ID NO: 105 is operably linked to the hsp70 intron and the GUS gene to generate the construct pMON49342. This construct is tested for promoter activity using the wheat reproductive tissue transient assay. GUS activity is not detected which could be due to any of the reasons described above.

7v. L1482835

SEQ ID NO: 103 is operably linked to the hsp70 intron and the GUS gene to generate the construct pMON49341. This construct is tested in the wheat reproductive tissue transient assay. GUS activity is detected at a level of expression much lower than seen with the rice actin promoter but greater than that seen with the no DNA bombardments indicating that SEQ ID NO: 101 has promoter activity.

Table 2. Summary of transient assay data testing for promoter activity of the DNA fragments containing SEQ ID NOS: 80–85, 88–98, 100–103, 105 and 108–111. In the first column are the Clone IDs of the EST sequences used to isolate the promoter fragments (see Example 3). In the second column are the SEQ ID numbers of the fragments tested in the transient assay. The construct names are listed in the third column. Each construct contains a fragment operably linked to the hsp70 intron and GUS gene. The Fourth column indicates the organism in which the assay is conducted. The fifth column is the level of GUS activity detected based on a qualitative evaluation of the number and intensity of positively staining cells in the assay. Low indicates much lower than 35S, medium indicates slightly lower than 35S, and high indicates greater than or equal to 35S.

and regeneration systems and methods are available and well known to those skilled in the art. The stably transformed plants and progeny are subsequently analyzed for expression of the gene in tissues of interest by any number of molecular, immunodiagnostic, biochemical, and/or field evaluation methods known to those skilled in the art.

The transient assay test described in Example 7 gives qualitative data regarding the promoter activity of the DNA fragments tested. The transient assay does not indicate whether the isolated promoters will act as predicted in vivo. To determine the promoter activity in male reproductive tissues, the promoter fragments are cloned upstream of a gene of interest (either GUS or the MS2 coat protein), placed in a plant transformation vector and transformed into plants

| Clone id | SEQ ID | pMON number | Organism | Level of activity |
|---|---|---|---|---|
| 700352709 | 80 | pMON48161 | wheat reproductive tissue | low |
| 700353208 | 100 | pMON53321 | wheat reproductive tissue | not detected |
| 700354820 | 81 | pMON48151 | wheat reproductive tissue | medium |
| 700356542 | 82 | pMON48143 | wheat reproductive tissue | not detected |
| 700382670 | 83 | pMON53300 | wheat reproductive tissue | not detected |
| 700383111 | 84 | pMON53314 | wheat reproductive tissue | not detected |
| L1481529 | 85 | pMON48160 | wheat reproductive tissue | medium |
| L1482113 | 88 | pMON48148 | wheat reproductive tissue | low |
| L1482830 | 89 | pMON48145 | wheat reproductive tissue | low |
| L1482865 | 90 | pMON48150 | wheat reproductive tissue | not detected |
| L1482865 | 108 | pMON48146 | wheat reproductive tissue | not detected |
| L1483194 | 91 | pMON48147 | wheat reproductive tissue | not detected |
| L1483239 | 92 | pMON53304 | wheat reproductive tissue | not detected |
| L1484055 | 93 | pMON48155 | wheat reproductive tissue | medium |
| L1484055 | 109 | pMON48156 | wheat reproductive tissue | medium |
| L1484762 | 94 | pMON53302 | wheat reproductive tissue | low |
| L1485873 | 110 | pMON48152 | wheat reproductive tissue | medium |
| L1485873 | 95 | pMON48153 | wheat reproductive tissue | medium |
| L30663465 | 111 | pMON48158 | wheat reproductive tissue | not detected |
| L30663465 | 96 | pMON48159 | wheat reproductive tissue | not detected |
| L30664420 | 97 | pMON48157 | wheat reproductive tissue | low |
| L1482016 | 102 | pMON49340 | wheat reproductive tissue | low |
| L30665422 | 98 | pMON48149 | wheat reproductive tissue | low |
| L30683230 | 101 | pMON53316 | wheat reproductive tissue | low |
| 700382279 | 105 | pMON49342 | wheat reproductive tissue | not detected |
| L1482835 | 103 | pMON49341 | wheat reproductive tissue | not detected |

Example 8

Promoter Activity Analysis in Stably Transformed Plants

Figure 2:
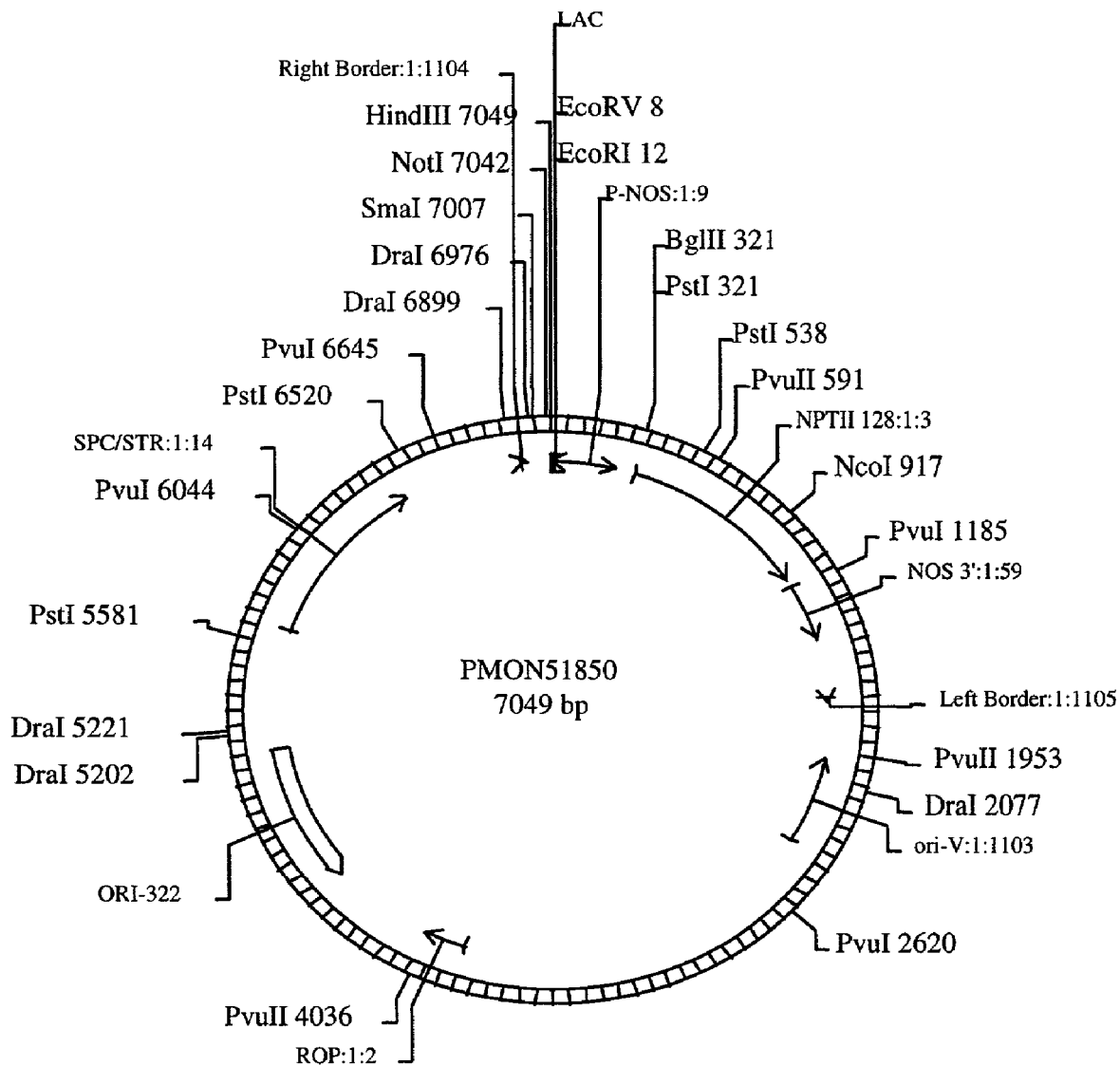
FIG. 2 is a plasmid map of pMON51850.

For stable plant transformation the 5' regulatory sequences are cloned into a plant transformation vector such as shown in FIG. 2. Plasmid pMON51850 is a double border (right and left T-DNA borders) plant transformation vector and contains the following genetic components: NOS 3' is the termination signal from the nopaline synthase gene; ori-322 and ori-V are origins of replication; kan is the coding region for kanomycin selection.

The promoter is operably linked to any gene of interest such as a glyphosate tolerance gene along with other regulatory sequences including, but not limited to, non-translated leaders and terminators as described above, and transformed into a target crop of interest via an appropriate delivery system such as Agrobacterium-mediated transformation (see, for example, U.S. Pat. Nos. 5,569,834, 5,416,011, 5,631,152, 5,159,135 and 5,004,863) or particle bombardment methods (see, for example, PCT Patent publications WO 92/15675 and WO 97/48814, European Patent Application EP586,355, and U.S. Pat. Nos. 5,120,657, 5,503,998, 5,830,728 and 5,015,580). A large number of transformation (as described in Example 6). Tissue from R0 plants are harvested and assayed for the gene of interest.

Detection of GUS activity in male reproductive tissues is referenced in Example 5. For the detection of the MS2 coat protein, anther extracts are analyzed by immunodetection on Western blots or ELISA analysis. For Western blots, the T7 tag monoclonal and horseradish peroxidase conjugated antibody (Novagen) is used to detect MS2 protein expression in anther tissues. Total protein is extracted (extraction buffer: 1×PBS and 0.01% Tween-20) from anther, 10 μg of total protein sample is separated on a 10–20% polyacrylamide gradient gel (BioRAD) and transferred onto ECL nitrocellulose membrane (Amersham). A 1:5000 dilution of primary antisera is used to detect ACOX protein using the ECL detection system (Amersham). A 15 Kd protein is detected.

For ELISA quantification of MS2 coat protein levels in anthers, crude anther extracts containing 1 μg total protein is added a 96-well Nunc-Immuno MaxiSorb plate coated with 100 μL of purified polyclonal anti-MS2 coat protein IgG antibody (0.1 ng/μl) in coating buffer (15 mM $Na_2CO_3$, 35 mM $NaHCO_3$, pH 9.6). The plate is sealed and incubated at 37° C. for one hour. The plate is then rinsed three times with ishing buffer (1×PBS, 0.05%, and Tween 20, pH7.4). Fifty microliter of the anther extract containing 1 μg of total protein is added to a well, followed by addition of 50 μL of a 1:10,000 dilution of anti-T7 tag monoclonal and HSP conjugated antibody (Novagen). The loaded plate is incubated at 37° C. for one hour then rinsed three times with ishing buffer. To develop the plate, 100 μL of substrate (a 1:1 mixture of $H_2O_2$ and TMB (3,3'-5,5'-tetra methyl benzidine), Kirgeggard and Perry, #50-76-03, Gaithersburg, Md.) is added to each well and the plate is incubated at room temperature for 3–5 min. One hundred microliter of stop solution (3M $H_3PO_4$) is added to terminate the reaction. The plate is read on a Spectra Max 340 (Molecular Devices, Sunnyvail, Calif. 94089) at 450 nm.

Plasmids can be transformed into two types of angiosperms: monocots or dicots. The promoter fragments are derived from *Zea mays* (corn), a monocot plant. Therefore, activity in a dicot plant would indicate a broad spectrum of plants in which the promoter is active. The dicot plant *Arabidopsis thaliana* offers several advantages as a model system to study promoter systems: ease of transformation, quick life cycle, and multiple stages of floral development on each plant. Promoters that are active in *Arabidopsis* anthers are likely to be active in many monocot and dicot species. To test this, some promoters that are active in *Arabidopsis* are also tested in monocot plants. As shown below and summarized in Table 3, all promoter fragments tested that are active in *Arabidopsis* are also active in monocots. Therefore, if the corn promoter fragment is active in *Arabidopsis*, it is likely to be active in monocots as well.

Table 3. Summary of promoter activity in stably transformed plants. In the first column are the Clone IDs of the EST sequences used to isolate the promoter fragments (see Example 3). The second column shows the SEQ ID numbers of the fragments tested in the transient assay. The third column lists the introns used in the constructs. No introns are used in constructs for dicot transformation. The fourth column lists the pMON number of each vector constructed. The fifth column lists the reporter genes used in the constructs. In the sixth column are the organisms transformed. The seventh column shows the type of assay used to detect the reporter gene. The eighth column shows the number of plants assayed. The ninth column shows the number of plants showing male expression and the last column lists any other tissues in which the reporter protein is detected.

8a. 700352709

To test for anther activity in wheat, SEQ ID NO: 80 is placed upstream of the hsp70 intron/MS2 coat protein gene cassette and put into a plant transformation vector resulting in the construct pMON52109. This construct is used to transform wheat. Anthers from 5 independent R0 wheat plants are assayed by Western blot for MS2 coat protein. MS2 coat protein is not detected which could be due to any of the reasons described above.

8b. 700354820

To test for anther activity in wheat, SEQ ID NO: 81 is placed upstream of the hsp70 intron/MS2 coat protein gene cassette and put into a plant transformation vector resulting in the construct pMON52008. This construct is used to transform wheat. Anthers from 5 independent R0 wheat plants are assayed by ELISA for MS2 coat protein. MS2 coat protein is detected in three lines. No activity is detected in leaf or glumes from these lines. These data indicate that SEQ ID NO: 81 acts as an anther enhanced promoter in monocots.

8c. L1481529

To test for anther activity in dicot plants SEQ ID NO: 85 is placed upstream of the GUS gene and put into a plant transformation vector resulting in the construct pMON48198. This construct is used to transform *Arabidopsis thaliana*. All five independent events show expression in the male reproductive tissues. No GUS expression is detected in other floral tissues. To test for anther activity in monocot plants, SEQ ID NO: 85 is placed upstream of the hsp70 intron/MS2 coat protein gene cassette and put into a plant transformation vector resulting in the construct pMON452108. This construct is used to transform wheat. Anthers from one R0 wheat plant are assayed by ELISA for MS2 coat protein. These data indicate that SEQ ID NO: 85 can act as an anther-enhanced promoter in dicots. Because it is monocot-derived promoter, it is likely to be active in monocot anthers as well. Not enough wheat lines are tested to make any conclusions at this time.

| Clone id | SEQ ID | Intron | pMON number | Exp. gene | Organism | Assay | # plants assayed | Male positive | Other |
|---|---|---|---|---|---|---|---|---|---|
| 700352709 | 80 | hsp70 | pMON52109 | MS2 CP | wheat | Western | 5 | 0 | |
| 700354820 | 81 | hsp70 | pMON52008 | MS2 CP | wheat | ELISA | 5 | 3 | not leaf not glume |
| L1481529 | 85 | | pMON48198 | Gus | Arabidopsis | X-gluc | 5 | 5 | pollen not female |
| L1481529 | 85 | hsp70 | pMON52108 | MS2 CP | wheat | ELISA | 1 | 0 | no leaf no female no glume |
| L1482113 | 88 | | pMON54700 | Gus | Arabidopsis | X-gluc | 7 | 7 | pollen not female |
| L1482830 | 89 | hsp70 | pMON42945 | MS2 CP | rice | Western | 16 | 0 | |
| L1482830 | 89 | hsp70 | pMON42945 | MS2 CP | wheat | ELISA | 2 | 1 | no leaf no female no glume |
| L1484055 | 93 | | pMON48197 | Gus | Arabidopsis | X-gluc | 10 | 8 | distal tip of sepal in pollen |
| L1484762 | 94 | hsp70 | pMON52023 | MS2 CP | wheat | ELISA | 2 | 1 | neg. line in leaf. pos line 1/2 trials |
| L30664420 | 97 | | pMON48189 | Gus | Arabidopsis | X-gluc | 5 | 0 | |
| L30664420 | 97 | hsp70 | pMON52107 | MS2 CP | wheat | Western | 5 | 0 | 3/5 vasculature |
| L1482016 | 102 | | pMON48199 | Gus | Arabidopsis | X-gluc | 1 | 0 | |
| L1482016 | 102 | hsp70 | pMON42946 | MS2 CP | wheat | Western | 10 | 0 | |
| L1482016 | 102 | hsp70 | pMON42946 | MS2 CP | wheat | ELISA | 3 | 1 | female not leaf not glume |
| L1482835 | 103 | | pMON54701 | Gus | Arabidopsis | X-gluc | 10 | 0 | |
| L30683230 | 101 | | pMON48195 | Gus | Arabidopsis | X-gluc | 5 | 0 | |
| L30683230 | 101 | hsp70 | pMON42948 | MS2 CP | wheat | Western | 9 | 0 | |
| L30683230 | 101 | hsp70 | pMON42948 | MS2 CP | wheat | ELISA | 5 | 2 | 1 + line 1 +/− line no glume no female |

8d. L1482113

To test for anther activity in dicot plants SEQ ID NO: 88 is placed upstream of the GUS gene and put into a plant transformation vector resulting in the construct pMON54700. This construct is used to transform *Arabidopsis thaliana*. All seven independent events show expression in the male reproductive tissues. GUS expression is not detected in other floral organs. These data indicate that SEQ ID NO: 88 can act as an anther-enhanced promoter in dicots. Because it is monocot-derived promoter, it is likely to be active in monocot anthers as well.

8e. L1482830

To test for anther activity in monocot plants, SEQ ID NO: 89 is placed upstream of the hsp70 intron/MS2 coat protein gene cassette and put into a plant transformation vector resulting in the constructs pMON42945. pMON42945 is used to transform *Oryza sativum* (rice) and *Triticum aesitivum* (wheat). Anthers from 16 independent R0 rice plants are assayed by Western blot for MS2 coat protein. No MS2 coat protein is detected in any of the lines. Anthers from 2 independent R0 wheat plants are assayed by ELISA for MS2 coat protein. One of the two plants is positive for MS2 coat protein. No MS2 coat protein is detected in leaf, the female reproductive organs, or the glumes. These data indicate that SEQ ID NO: 89 can act as an anther-enhanced promoter in wheat. Because ELISA assays are more sensitive the Westerns, it is likely that expression in rice is below the limit of detection.

8f. L1484055

To test for anther activity in dicot plants SEQ ID NO: 93 is placed upstream of the GUS gene and put into a plant transformation vector resulting in the construct pMON48197. This construct is used to transform *Arabidopsis thaliana*. Eight of ten independent events show expression in the male reproductive tissues. GUS expression is detected in the distal tips of the sepals, but not detected in other floral organs. These data indicate that SEQ ID NO: 93 can act as an anther-enhanced promoter in dicots. Because it is monocot-derived promoter, it is likely to be active in monocot anthers as well.

8g. L1484762

To test for anther activity in monocot plants, SEQ ID NO: 94 is placed upstream of the hsp70 intron/MS2 coat protein gene cassette and put into a plant transformation vector resulting in the constructs pMON52023. PMON52023 is used to transform *Triticum aesitivum* (wheat). Anthers from two independent R0 wheat plants are assayed by ELISA for MS2 coat protein. One of the two plants is positive for MS2 coat protein. MS2 coat protein is detected in leaf, but not in the female reproductive organs, or the glumes. These data indicate that SEQ ID NO: 94 can act as an anther-enhanced promoter in monocot plants.

8h. L30664420

To test for anther activity in dicot plants SEQ ID NO: 97 is placed upstream of the GUS gene and put into a plant transformation vector resulting in the construct pMON48189. This construct is used to transform *Arabidopsis thaliana*. Gus expression is not detected in five independent events. To test for anther activity in monocots, SEQ ID NO: 97 is placed upstream of the hsp70 intron/MS2 coat protein gene cassette and put into a plant transformation vector resulting in the construct pMON52107. This construct is used to transform wheat. Anthers from five independent R0 wheat plants are assayed by western blot for MS2 coat protein. MS2 coat protein is not detected which could be due to any of the reasons described above.

8i. L1482016

To test for anther activity in dicot plants SEQ ID NO: 102 is placed upstream of the GUS gene and put into a plant transformation vector resulting in the construct pMON48199. This construct is used to transform *Arabidopsis thaliana*. Gus expression is not detected in one event. However, one event is not sufficient to draw any conclusions at this time. To test for anther activity in monocots, SEQ ID NO: 102 is placed upstream of the hsp70 intron/MS2 coat protein gene cassette and put into a plant transformation vector resulting in the construct pMON42946. This construct is used to transform wheat. Anthers from 10 independent R0 wheat plants are assayed by Western blot for MS2 coat protein. MS2 coat protein is not detected which could be due to any of the reasons described above. Anthers from three independent R0 wheat plants are assayed by ELISA for MS2 coat protein. One of the three plants is positive for MS2 coat protein. MS2 coat protein is detected in female reproductive organs, but not in the leaf, or the glumes. These data indicate that SEQ ID NO: 102 can act as an anther-enhanced promoter in monocot plants.

8j. L1482835

To test for anther activity in dicot plants SEQ ID NO: 103 is placed upstream of the GUS gene and put into a plant transformation vector resulting in the construct pMON54701. This construct is used to transform *Arabidopsis thaliana*. Gus expression is not detected in ten independent events that could be due to any of the reasons described above.

8k. L30683230

To test for anther activity in dicot plants SEQ ID NO: 101 is placed upstream of the GUS gene and put into a plant transformation vector resulting in the construct pMON48195. This construct is used to transform *Arabidopsis thaliana*. Gus expression is not detected in five events. To test for anther activity in monocots, SEQ ID NO: 101 is placed upstream of the hsp70 intron/MS2 coat protein gene cassette and put into a plant transformation vector resulting in the construct pMON42948. This construct is used to transform wheat. Anthers from 9 independent R0 wheat plants are assayed by Western blot for MS2 coat protein. MS2 coat protein is not detected which could be due to any of the reasons described above. Anthers from five independent R0 wheat plants are assayed by ELISA for MS2 coat protein. Two of five plants are positive for MS2 coat protein. MS2 coat protein is detected in female reproductive organs, but not in the leaf, or the glumes. These data indicate that SEQ ID NO: 101 can act as an anther-enhanced promoter in monocot plants.

Example 9

Identification of Cis Elements and Engineering Novel Promoters

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. Nos. 5,223,419, 4,990,607, and 5,097,025.

An alternative approach is to look for similar sequences between promoters with similar expression profiles. Promoters with overlapping patterns of activity can have common regulatory mechanisms. Several computer programs can be used to identify conserved, sequence motifs between promoters, including, but not limited to, MEME, SIGNAL SCAN, or GENE SCAN. These motifs can represent binding sites for transcription factors which act to regulate the promoters. Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by adding to an active promoter and testing for a reduction in promoter activity. Some cis acting regulatory elements may require other elements to function. Therefore, multiple elements can be tested in various combinations by any number of methods known to those skilled in the art.

Once functional promoter elements have been identified, promoter elements can be modified at the nucleotide level to affect protein binding. The modifications can cause either higher or lower affinity binding that would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element.

The technical methods needed for constructing expression vectors containing the novel engineered 5' regulatory elements are known to those of skill in the art. The engineered promoters are tested in expression vectors and tested transiently by operably linking the novel promoters to a suitable reporter gene such as GUS and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

What is claimed is:

1. An isolated nucleic acid comprising a sequence of SEQ ID NO: 81 said isolated nucleic acid being capable of regulating transcription of an operably linked DNA sequence.

2. The isolated nucleic acid of claim 1 wherein the isolated nucleic acid is a promoter.

3. The isolated nucleic acid of claim 2 wherein the promoter is a hybrid promoter.

4. The isolated nucleic acid of claim 1 wherein said isolated nucleic acid confers enhanced expression of operably linked genes in male reproductive tissues.

5. The isolated nucleic acid of claim 4 further comprising a minimal promoter.

6. The isolated nucleic acid of claim 5 wherein the minimal promoter is selected from the group consisting of a minimal CAMV and a rice actin promoter.

7. The isolated nucleic acid of claim 6 wherein the minimal promoter is a minimal CAMV 35S promoter.

8. The promoter of claim 1 wherein said promoter confers enhanced expression of operably linked genes in male reproductive tissues.

9. The promoter of claim 8 wherein said male reproductive tissues comprise anthers.

10. A cell comprising a recombinant DNA construct comprising an isolated nucleic acid sequence of SEQ ID NO: 81, and operably linked to said nucleic acid sequence, a transcribable DNA sequence and a 3' non-translated region.

11. A transgenic plant comprising a DNA construct comprising an isolated nucleic acid sequence of SEQ ID NO: 81 and operably linked to said nucleic acid sequence, a transcribable DNA sequence and a 3' non-translated region.

12. A method of making a transgenic plant comprising introducing into a cell of a plant a recombinant DNA construct comprising:
   (i) A promoter comprising a nucleic acid sequence of SEQ ID NOS: 81 and, operably linked to the promoter;
   (ii) A transcribable DNA sequence; and
   (iii) A 3' non-translated region.

* * * * *

SEQUENCE LISTING

```
<160> NUMBER OF SEQ ID NOS: 111

<210> SEQ ID NO 1
<211> LENGTH: 22
<212> TYPE: DNA
<213> ORGANISM: artificial sequence
<220> FEATURE:
<221> NAME/KEY: misc_feature
<222> LOCATION: (1)..(22)
<223> OTHER INFORMATION: synthetic primer sequence

<400> SEQUENCE: 1
gtaatacgac tcactatagg gc                                              22

<210> SEQ ID NO 2
<211> LENGTH: 19
<212> TYPE: DNA
<213> ORGANISM: artificial sequence
<220> FEATURE:
<221> NAME/KEY: misc_feature
<222> LOCATION: (1)..(19)
<223> OTHER INFORMATION: synthetic primer sequence

<400> SEQUENCE: 2
actatagggc acgcgtggt                                                  19
```

```
<210> SEQ ID NO 3
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic primer sequence

<400> SEQUENCE: 3
agggcaagct tggtcgacgg cccgggctg gt                                    32

<210> SEQ ID NO 4
<211> LENGTH: 28
<212> TYPE: DNA
<213> ORGANISM: artificial sequence
<220> FEATURE:
<221> NAME/KEY: misc_feature
<222> LOCATION: (1)..(28)
<223> OTHER INFORMATION: synthetic primer sequence

<400> SEQUENCE: 4
ggtggatgcg gcttcgggtg cttcagcg                                        28

<210> SEQ ID NO 5
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 5
ggatccagat ctggcagact cagtgccttg gcagcactg                            39

<210> SEQ ID NO 6
<211> LENGTH: 26
<212> TYPE: DNA
<213> ORGANISM: artificial sequence
<220> FEATURE:
<221> NAME/KEY: misc_feature
<222> LOCATION: (1)..(26)
<223> OTHER INFORMATION: synthetic primer sequence

<400> SEQUENCE: 6
gaaaggtggc aaggaggaga accacc                                          26

<210> SEQ ID NO 7
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 7
ggatccagat ctcttgtttt gggccatcag tagtgcttc                            39

<210> SEQ ID NO 8
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence
```

```
<400> SEQUENCE: 8
actcgtcgcg gccgttggcg gcagccg                                    27

<210> SEQ ID NO 9
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 9
ggatccagat ctcccacgcc ccggccggca cgttgacac                       39

<210> SEQ ID NO 10
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 10
gcggtcatgc ctcccttgag catgctc                                    27

<210> SEQ ID NO 11
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 11
ctgggcaacg atggcaccag cgatgac                                    27

<210> SEQ ID NO 12
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 12
cgtcgtcgta ccagcgcagc gtcgtca                                    27

<210> SEQ ID NO 13
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 13
ggatccagat ctcatcttgg gtatggtggc ggcgacggc                       39

<210> SEQ ID NO 14
<211> LENGTH: 33
<212> TYPE: DNA
<213> ORGANISM: artificial sequence
```

```
<220> FEATURE:
<221> NAME/KEY: misc_feature
<222> LOCATION: (1)..(33)
<223> OTHER INFORMATION: synthetic primer sequence

<400> SEQUENCE: 14
ggatccagat ctctgcacca ggggcttggt gcg                                    33

<210> SEQ ID NO 15
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 15
cagtacaaat aagccgtgca gggaaac                                           27

<210> SEQ ID NO 16
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 16
ggatccagat cttccttctt tgttgatctg tgtcaccat                              39

<210> SEQ ID NO 17
<211> LENGTH: 34
<212> TYPE: DNA
<213> ORGANISM: artificial sequence
<220> FEATURE:
<221> NAME/KEY: misc_feature
<222> LOCATION: (1)..(34)
<223> OTHER INFORMATION: synthetic primer sequence

<400> SEQUENCE: 17
ggatccagat ctctgaaagt cagaaagtgt aagg                                   34

<210> SEQ ID NO 18
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 18
tgacgacgag gacggcgaag aggatcc                                           27

<210> SEQ ID NO 19
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 19
ggatccagat ctgcggtggt ggtggtacgt cggcggcgg                              39
```

```
<210> SEQ ID NO 20
<211> LENGTH: 28
<212> TYPE: DNA
<213> ORGANISM: artificial sequence
<220> FEATURE:
<221> NAME/KEY: misc_feature
<222> LOCATION: (1)..(28)
<223> OTHER INFORMATION: synthetic primer sequence

<400> SEQUENCE: 20
tgagcaggac gccggcgcgg tccctgtc                                        28

<210> SEQ ID NO 21
<211> LENGTH: 24
<212> TYPE: DNA
<213> ORGANISM: artificial sequence
<220> FEATURE:
<221> NAME/KEY: misc_feature
<222> LOCATION: (1)..(24)
<223> OTHER INFORMATION: synthetic primer sequence

<400> SEQUENCE: 21
tggagcggtc gagcttgccg atgc                                            24

<210> SEQ ID NO 22
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 22
acctttgtgc cattccattt cgcgatg                                         27

<210> SEQ ID NO 23
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 23
acacccggtg taacgtcaca gcctcgc                                         27

<210> SEQ ID NO 24
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 24
gggtagacgt tgacaccacg caggagc                                         27

<210> SEQ ID NO 25
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence
```

-continued

```
<400> SEQUENCE: 25
ggatccagat ctaattcctc ggctatcgtc gtgagccag                                39

<210> SEQ ID NO 26
<211> LENGTH: 30
<212> TYPE: DNA
<213> ORGANISM: artificial sequence
<220> FEATURE:
<221> NAME/KEY: misc_feature
<222> LOCATION: (1)..(30)
<223> OTHER INFORMATION: synthetic primer sequence

<400> SEQUENCE: 26
tagcccgcca cccgccgctg ccgcttcatc                                          30

<210> SEQ ID NO 27
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 27
ggatccagat ctgggtcgcc aaaacaaccc gtgcgcacc                                39

<210> SEQ ID NO 28
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 28
gagcaggagc aggacgaggc acgcgac                                             27

<210> SEQ ID NO 29
<211> LENGTH: 37
<212> TYPE: DNA
<213> ORGANISM: artificial sequence
<220> FEATURE:
<221> NAME/KEY: misc_feature
<222> LOCATION: (1)..(37)
<223> OTHER INFORMATION: synthetic primer sequence

<400> SEQUENCE: 29
ggatccagat ctcggacgag gaggaggccg gcgccat                                  37

<210> SEQ ID NO 30
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic primer sequence

<400> SEQUENCE: 30
ggatccagat cttgcattgc atttgcatct cg                                       32

<210> SEQ ID NO 31
<211> LENGTH: 26
<212> TYPE: DNA
<213> ORGANISM: artificial sequence
```

```
<220> FEATURE:
<221> NAME/KEY: misc_feature
<222> LOCATION: (1)..(26)
<223> OTHER INFORMATION: synthetic primer sequence

<400> SEQUENCE: 31
cgcagaggac cttcttcatc tccatg                                          26

<210> SEQ ID NO 32
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 32
ggatccagat ctgcgggtgg atcacttcgt cgctcctgg                            39

<210> SEQ ID NO 33
<211> LENGTH: 26
<212> TYPE: DNA
<213> ORGANISM: artificial sequence
<220> FEATURE:
<221> NAME/KEY: misc_feature
<222> LOCATION: (1)..(26)
<223> OTHER INFORMATION: synthetic primer sequence

<400> SEQUENCE: 33
ctttgtgcag tccgtcttgc cgtcgc                                          26

<210> SEQ ID NO 34
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 34
ggatccagat ctgccgtcgc tggtcgcgcc gagtttgga                            39

<210> SEQ ID NO 35
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic primer sequence

<400> SEQUENCE: 35
ggatccagat ctctccttcc tgtggccgcc gg                                   32

<210> SEQ ID NO 36
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 36
gagcgccagc accagtagcg cggcggc                                         27
```

<210> SEQ ID NO 37
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 37
ggatccagat ctgaggccct cgcctatgcg cgccctgcg                39

<210> SEQ ID NO 38
<211> LENGTH: 30
<212> TYPE: DNA
<213> ORGANISM: artificial sequence
<220> FEATURE:
<221> NAME/KEY: misc_feature
<222> LOCATION: (1)..(30)
<223> OTHER INFORMATION: synthetic primer sequence

<400> SEQUENCE: 38
ccttgtagcc gcacgcgccg ccgtccgtgg                         30

<210> SEQ ID NO 39
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 39
ggatccagat cttgtcagtt aacccgtcgc gcccgccgt               39

<210> SEQ ID NO 40
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic primer sequence

<400> SEQUENCE: 40
ggatccagat cttattgtcc acgaacgacc ag                      32

<210> SEQ ID NO 41
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 41
cgtgtgcggg atcagttgcg cttgcgc                            27

<210> SEQ ID NO 42
<211> LENGTH: 36
<212> TYPE: DNA
<213> ORGANISM: artificial sequence
<220> FEATURE:
<221> NAME/KEY: misc_feature
<222> LOCATION: (1)..(36)
<223> OTHER INFORMATION: synthetic primer sequence

```
<400> SEQUENCE: 42
ggatccagat ctatgctgaa gctgctgaga gtgcgg                              36

<210> SEQ ID NO 43
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 43
cagcacgcga gaaggatcag cgcgaac                                        27

<210> SEQ ID NO 44
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: synthetic primer sequence

<400> SEQUENCE: 44
ggatccagat ctccctccct ctatatcgtc tcgtgtgctg                          40

<210> SEQ ID NO 45
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 45
ggcgcataca accattaggg tgaacag                                        27

<210> SEQ ID NO 46
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 46
ctgagagtgt tgtttgtgga agcagcc                                        27

<210> SEQ ID NO 47
<211> LENGTH: 35
<212> TYPE: DNA
<213> ORGANISM: artificial sequence
<220> FEATURE:
<221> NAME/KEY: misc_feature
<222> LOCATION: (1)..(35)
<223> OTHER INFORMATION: synthetic primer sequence

<400> SEQUENCE: 47
ggatccagat ctgctagttc tctcctcgcc tttgg                               35

<210> SEQ ID NO 48
<211> LENGTH: 26
<212> TYPE: DNA
<213> ORGANISM: artificial sequence
```

```
<220> FEATURE:
<221> NAME/KEY: misc_feature
<222> LOCATION: (1)..(26)
<223> OTHER INFORMATION: synthetic primer sequence

<400> SEQUENCE: 48
ccaacagcgc ctccttcaga ggctcg                                          26

<210> SEQ ID NO 49
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 49
ggatccagat ctttcgctgt ggccgctcgt cccgcggta                            39

<210> SEQ ID NO 50
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic primer sequence

<400> SEQUENCE: 50
ggatccagat ctgctaactc tggtgtgaaa cc                                   32

<210> SEQ ID NO 51
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 51
gcggccaccg aggccaagcg                                                 20

<210> SEQ ID NO 52
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 52
ccgtcctggg cgaccaccgt                                                 20

<210> SEQ ID NO 53
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 53
gggcaccccg ctgcgcccgt tcttgga                                         27
```

```
<210> SEQ ID NO 54
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 54
taccctgtgg tcgccggaca tggtgtt                               27

<210> SEQ ID NO 55
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 55
ctgcacgcct ggcctgggct                                       20

<210> SEQ ID NO 56
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 56
tcggcgttgt gtcgttgggc                                       20

<210> SEQ ID NO 57
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 57
gcagaggccg gccggcggcg acgcggt                               27

<210> SEQ ID NO 58
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: synthetic primer sequence

<400> SEQUENCE: 58
ggatcctaga tctgcgacgc ggtggaggac gtacggtggt                 40

<210> SEQ ID NO 59
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence
```

<400> SEQUENCE: 59
cgagcgacga cgagatgatc                                                   20

<210> SEQ ID NO 60
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 60
ccgttcacca cgtcgatcag                                                   20

<210> SEQ ID NO 61
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 61
gcggctcctt attacggccg ccatcga                                           27

<210> SEQ ID NO 62
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: synthetic primer sequence

<400> SEQUENCE: 62
ggatcctaga tctcgacacc gtgtgtgtgt ggactccggt                             40

<210> SEQ ID NO 63
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 63
gtacggtcag cccaacggtg                                                   20

<210> SEQ ID NO 64
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 64
gggctttgcc agggagccga                                                   20

<210> SEQ ID NO 65
<211> LENGTH: 27
<212> TYPE: DNA
<213> ORGANISM: artificial sequence

```
<220> FEATURE:
<221> NAME/KEY: misc_feature
<222> LOCATION: (1)..(27)
<223> OTHER INFORMATION: synthetic primer sequence

<400> SEQUENCE: 65
ttgccgtcct tgaagatggg gacgttg                                27

<210> SEQ ID NO 66
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 66
ctggtagggt ggcaggttca cgttctt                                27

<210> SEQ ID NO 67
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 67
gaccccagcg cggactgctg                                        20

<210> SEQ ID NO 68
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 68
ggagctcgac tgctctcact                                        20

<210> SEQ ID NO 69
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 69
tgcgcggggg gcggtggctg cttctag                                27

<210> SEQ ID NO 70
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 70
tgttgccttc gtctttgtgg gggctgg                                27
```

```
<210> SEQ ID NO 71
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 71
ggcgagtgcg tgcgttcgtg                                              20

<210> SEQ ID NO 72
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: synthetic primer sequence

<400> SEQUENCE: 72
gaagtgggtc ttgcagtaca                                              20

<210> SEQ ID NO 73
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence

<400> SEQUENCE: 73
gtcctgcgtg ccggtgaaag acatggt                                      27

<210> SEQ ID NO 74
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: synthetic primer sequence

<400> SEQUENCE: 74
ggatcctaga tctccggacg cctgtctgtg gctgcacgaa                        40

<210> SEQ ID NO 75
<211> LENGTH: 30
<212> TYPE: DNA
<213> ORGANISM: artificial sequence
<220> FEATURE:
<221> NAME/KEY: misc_feature
<222> LOCATION: (1)..(30)
<223> OTHER INFORMATION: synthetic primer sequence

<400> SEQUENCE: 75
ggatccagat ctagtagtgc ttctatttag                                   30

<210> SEQ ID NO 76
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic primer sequence
```

```
<400> SEQUENCE: 76
agatctctgg gcaacgatgg caccagc                                        27

<210> SEQ ID NO 77
<211> LENGTH: 28
<212> TYPE: DNA
<213> ORGANISM: artificial sequence
<220> FEATURE:
<221> NAME/KEY: misc_feature
<222> LOCATION: (1)..(28)
<223> OTHER INFORMATION: synthetic primer sequence

<400> SEQUENCE: 77
agatcttggt tctctgcaga aacgaccg                                       28

<210> SEQ ID NO 78
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: synthetic primer sequence

<400> SEQUENCE: 78
ggatccagat ctatttcctg tcccccctgt gaatgtcgg                           39

<210> SEQ ID NO 79
<211> LENGTH: 35
<212> TYPE: DNA
<213> ORGANISM: artificial sequence
<220> FEATURE:
<221> NAME/KEY: misc_feature
<222> LOCATION: (1)..(35)
<223> OTHER INFORMATION: synthetic primer sequence

<400> SEQUENCE: 79
ggatccagat ctgctagttc tctcctcgcc tttgg                               35

<210> SEQ ID NO 80
<211> LENGTH: 547
<212> TYPE: DNA
<213> ORGANISM: Zea mays

<400> SEQUENCE: 80
aaactaattt acacctcaat caaatttaac atgtggattg tgatgaatac tatagtacca    60
aacaaagcat tagggtttct attcgtgtat acccctaatt agttggtatg ctgccttcta    120
gtaaggggta aaaagggat tcaaaaaata cagaagcaaa acaataatt tattctcatt      180 ttcactcccg caatatacca ttcccgaatg aaagaaaaaa caaattcctt tcttttttat    240
ccctactaac ggccgaccat cggatttggt ctccacctca agtctctgcg agagttcctg    300
ccatcctctc aaacttacgg acacaacacc tataaaaatt cttcaccgtc gcccttcgca    360
actcacccca caaagcaata acccggccct ctcctttcgt caccatcaca tccagccagc    420
caacaaaaat gtcgcgcgtc acagctgcgg tgctctttta catcctcgcc gttgctgccc    480
tcagcgcggc cgaggccccg gcagagtcac cgaaggaagg cagtgctgcc aaggcactga    540
gtctgcc                                                              547

<210> SEQ ID NO 81
<211> LENGTH: 666
<212> TYPE: DNA
<213> ORGANISM: Zea mays
```

```
<400> SEQUENCE: 81
ctgcggctgc tatcaccact caccaactcc aattaaagat ctcgctacgc tagctttgca      60
cttcctctct ctctctctac tggccggccc tgtcagtggc agcgcccggt ttgctgctag     120
ctgagctgcg ggcgtcgctc ttagatatag cccaaaactc actccaccac cactcgttcc     180
atggaaccct agaccaaaag tacttcacgc tctcgcctct cgctctcgcc ctctccctct     240
ccctctccgc agcaaaagag atcccggccg agaagggcgc gcgctagctg cccggctagc     300
tgctggcgcc cgcgcgcccg cgcatatatc tgtgtcatcg ccatcaccca caccatggcc     360
cggccggcca acaccgccgt attagctctg tctgtcgctc gtccacctgc gaccgactga     420
gcgatccatc tccaccgagc tctccgcgct aagcgctgtc cttgccgccg tcctcccctc     480
cgtcctctac gcatccattt ccgtgtgctg ctcgtgtgtg tctgcgcggg cgctcctgct     540
cctgctcctg ctccctccgg ccccctcctcc cccgccgcc cgcgcgacct gcacctgcac     600
agatcgggcg gccgggccga ccgaccgatc gatcgattat cgtgtcaacg gccggcgggg     660
cgtggg                                                                666

<210> SEQ ID NO 82
<211> LENGTH: 1495
<212> TYPE: DNA
<213> ORGANISM: Zea mays

<400> SEQUENCE: 82
aaaatttact atgtaatttc atgtaaaaat ggtttctaat ttgatcgagt atatatatga      60
aaattttaga tgacttatag aaaaattcta gatccgccat ggctgcaga gtgtagagga     120 tgtgcatgca cagatgcact tcattgttgt tatatataca acaagttttc atgcaataca     180
agcctataaa taaatgtcct gactaagctt tcgtccacag aatttaccac ttcttccgct     240
gagtactacc gattcaacag aacagataga ccactcgtta acactgtaca cttctaccta     300
tatattcgct tctctcctct tgcaaatcat attgtcaata gtaacagtga aagaacaca     360 caaaatgagg gttcttgtag agaagctgtt agtctctgtg tttttagcag cattctattc     420
aggttggttg agagtcagtt gtctgcgtga attatttccc aacagattgg tttccaatcc     480
actctttgtt tctggtgtac attattctta cgtggagcaa cttttctgatc tctttctttg     540 tctcaatttc gtgtagggtg catggtcgtg tctctagaat atgatcacac ggcaagcatc     600
gaggcaagtg ttgtccacgt taattttcta agctcgcgtg ctaaaacatt gtttattgca     660
agagttaaat gaaaatccgt taatctctgt gcatcatata acggagcgaa aaacattaaa     720
acgtatattt tcaagtaaaa ccatgtacag ttttttcttt cagtagtacg ataacctctt     780
gtcaggaatt tacagatgag aaaattcatc gatgtaatct ttcaagttca taaaatgctc     840
tcaacaatcc agctgcaaat cctgcaatcc tttgaatttg tttcgatacg aaacaatcca     900
tccgtattaa tccgtaggtc atttcgtttg gagtagaata gtttgaagtg ctgcaacttt     960
ttgctcgaat gacgtcgata caaatatacg tggtaccgta cgttcttata tgtttgtgaa    1020
ataaataatc cgcagtgcct tggcgaccca atgaaaccct tgtacaaggg cggcattgtc    1080
cagaacagcg agttcaacag cggactgatg ggctggtcga cacaccggaa cgtcaaggcc    1140
ggcgtgagca gatcgccgtc cggcaacaag tttgcagtgg tgcatgggc gggaagctac    1200 gtgagcagca gcggcaagct cctaccgtcc cacagcgtgt accagagaat ccagatgcag    1260
agcgacaggc actactcgct atcaggtacg tacgtgatct gagaggagga gacagatcga    1320
tgagaccaca tcgatcgtat cccttttgac agtgtagcat tcccttcatg catggtttct    1380
```

```
ggtttgtgta gcatggctgc aggtgtcgaa cggcacgtcg gcacatgtga gggcggtgat   1440
caagtccccc aacggcgaac gcgtcatcgc tggtgccatc gttgcccaga gatct        1495
```

<210> SEQ ID NO 83
<211> LENGTH: 824
<212> TYPE: DNA
<213> ORGANISM: Zea mays

<400> SEQUENCE: 83

```
ctgccgctgg cgggcggcgg cggcggcgcc ctgaagccgg acttctatag ccagtcgtgc    60
ccgcgcgcgg agcggatcat tgcggaggtg atgcagacga gcagatggc gaacccgacg    120 acggccgcgg gcctgctccg cgtcttcttc cacgactgct tcgtcagcgg gtgcgacgcg   180
tcggtgctga tcgcgtccac ccagttccag aagtcggagc acgacgcgga gatcaaccac   240
tccctccccg gggacgcctt cgacgccgtg gtgcgcgcca agctggccct ggagctggag   300
tgccccgggg tggtgtcctg cgccgacatc ctcgcactgg cgtcgggcgt gctgattacc   360
atgaccggcg ggccccggta cccggttccg ctggggcgca gggactcgct gtcgtcgtcg   420 cccacgcgc ccgacgtgga gctgccgcac gccaacttca ccgtggaccg cctcatccag    480
atgttcggcg ccaagggggtt cacggtgcag gagctggtgg cgctgtccgg cgcccacacg   540
ctgggcttct cccactgcaa ggagttcgcc gaccgcctct acaacttccg caaccagggc    600
gggaagccgg agcagttcga ccccagcatg aacccgtcct acgccagggg gctgcaggac   660
gtgtgcaggg actacctcaa ggaccccacc atcgccgcgt tcaacgacat catgacgccc   720
ggcaagttcg acaacatgta cttcgtcaac ctcgagcgcg gcctcggcct gctcagcacc   780
gacgaggagc tgtggacgga cccacgcacc agccctggt gcag                      824
```

<210> SEQ ID NO 84
<211> LENGTH: 886
<212> TYPE: DNA
<213> ORGANISM: Zea mays

<400> SEQUENCE: 84

```
ctgccgcggt cggatttggt ggctaactag ggtttggtgc ttgagtggca ggcggagggt    60
atggcccgca gcagggttac tcggaagagc ggagcagcgc gcggcgggtg ccgaccact    120 acagcgcgcg gtccaaccag acactcgagg aacgcgagaa cagccccatc atccacctca   180
agaagctcaa caactgggtg gtctcaatt cagtttactg ccctatcgaa ccgtccctgg    240
attcttgata aaaatggggg acccgtgtgt tttgatacat cctgtgagta actgcactga   300
cggagtaact gttcaatttg tgtgtttgga cagatcaaga gtgtattggt ccagttgtat   360
gcacgcccgg gtgactgcgt tctcgatctt gcttgcggga aggttagtgg catgttgccg   420
ttgccctgca tagtagaaag caatggttcc tgagcttgat ggtagcatta accattaagg   480
tgtgcttatt tgtttgtaat tcagggaggt gatttgataa agtgggataa agccaaggtt    540
ggctactatg taggggttga tattgctgaa ggctcggtta gtatcctgtc acataagaca   600
tttattctat gtgtacattt gtacaatgtg caccagaagt tgttatgtat tagcttttag    660
cttcaccatt ttttaattct tataattgat gccttatgaa ttctcagtat gaactaatca   720
attgaacgct ttatgttgta atgatatctg atgtgaaata actttgtgt ttctgcatca    780 cttttgagca caggcatata aatatattaa gaccttacac tttctgactt tcagataaaa   840
gattgcatga ctcgctacaa tggtgacaca gatcaacaaa gaagga                   886
```

<210> SEQ ID NO 85
<211> LENGTH: 812
<212> TYPE: DNA
<213> ORGANISM: Zea mays

<400> SEQUENCE: 85

| aacaatcaga | acaccagcac | caaatcggcc | caagattcac | cagcaaaaat | tctttatatt | 60 |
| aacgatatgt | gcaataagtt | ttttttgtca | gtttgtgcag | tgccaattac | catcaacgcc | 120 |
| tatgtaagct | actagctcgg | taacgagcac | gtgccgtaac | aagccgagct | agcttaatat | 180 |
| gtcgtaatgt | ctcattatac | tcatcgttta | gttagtgttt | taaggtgtct | aaattcacaa | 240 |
| catatgtatt | tagacctaag | ttacgtccag | atttagagga | ttttttttgt | atctagtagg | 300 |
| aagccaaaac | gactaatata | atagaataga | tggagtatta | gttttctaaa | caattttgta | 360 |
| ctaagaatcg | aaaactgtat | ctcggttggg | cctgggccgg | acctggttag | cctgtgtaaa | 420 |
| ggctcccaat | cgatcgcgca | gcccggccgg | cattggcgca | ttgcacgctt | ggctggatct | 480 |
| ccggccagcc | attttcgttg | tgaaccacta | gtttcatccg | tcaatttcat | ccgtcccaat | 540 |
| taacagctac | tcctaaatta | atggcattct | atacatggtt | agctagcccc | tgatttcact | 600 |
| cgtgtcctca | cgtacccatc | cttcccgtgg | ctataaagcc | ctccctcctc | gccgcctcca | 660 |
| aagcagcaga | aagcaatcga | gaggagaacc | agcagcctcc | aataagagcc | agccagagaa | 720 |
| actaataaaa | ctctcgccgc | cgccatccga | gcgaacaagc | caaccgaccc | cgtccccaag | 780 |
| gcaatccgcc | gccgacgtac | caccaccacc | gc | | | 812 |

<210> SEQ ID NO 86
<211> LENGTH: 655
<212> TYPE: DNA
<213> ORGANISM: Zea mays

<400> SEQUENCE: 86

| aaattaagag | tactttgtat | atctgttcag | attataatgc | aaacaaacac | ctactataca | 60 |
| tagcagcata | gaagtcgtca | agttttgtgg | accgctgaga | aacccaacca | aactcgacgg | 120 |
| attttcacca | catttcacct | tgccaatgcc | atttgccatg | gcacaagacc | aggtcaaaac | 180 |
| ggsccgctct | atttttttgaa | tggtcaaaat | ggcgttcttc | tccgttgcac | actatctcta | 240 |
| cgggcaacca | gacaaatctt | cggtctccca | tgttatttaa | ggtcaccata | ggccctgctg | 300 |
| cgaaaccagg | atagtttgtt | tggctaccct | cgtcgtcgtc | tcactcaccc | cgccttcacg | 360 |
| cctccctcac | caaataaggt | cccgcccttt | ttccgacatt | cacaggggggg | acaggaaatc | 420 |
| accggccatg | gcctcgattc | cgggcgacga | ccttcgccgt | catcttatcc | gtcctcttct | 480 |
| gtgccgcggc | tggcaccgcc | gtcgacaacg | acctccccga | ctacgtcatc | cagggccgcg | 540 |
| tctattgcga | cacctgccgc | gccgggttcg | tgaccaacgt | caccgagtac | atcgcgggcg | 600 |
| ccaaggtgag | gctggagtgc | aggcacttcg | gcatcggcaa | gctcgaccgc | tccaa | 655 |

<210> SEQ ID NO 87
<211> LENGTH: 586
<212> TYPE: DNA
<213> ORGANISM: Zea mays

<400> SEQUENCE: 87

| aaattaagag | tattttgtta | gattatataa | tctgttcaga | ttataatgca | aacaaacacc | 60 |
| tactatacat | agcagcatag | aagtggtcaa | gttttgtgga | ccgctgagaa | acccaaccaa | 120 |
| actctatttt | ttgaatggtc | aaaatggcgt | tcttctccgt | tgcacactat | ctctacgggc | 180 |

```
aaccagacaa atcttcgggt ctcccatgtt atttaaggtc accataggcc ctgctgcgaa      240
accaggatag tttggctacc ctcgtcgtcg tctcactcac cccgccttca cgcctccctc      300
accaaataag gtcccgccct tttccgacat tcacagggg gacaggaaat cagcggccat       360
ggcctcgatt ccggcgacg accttcgccg tcatcttatc cgtcctcttc tgtgccgcgg      420
ctggcaccgc cgtcgacaac gacctccccg actacgtcat ccagggccgc gtctactgcg    480
acacctgccg cgccgggttc gtgaccaatg tcaccgagta catcgcgggc gccaaggtga    540
ggctggagtg caagcacttc ggcatcggca agctcgaccg ctccaa                     586
```

<210> SEQ ID NO 88
<211> LENGTH: 679
<212> TYPE: DNA
<213> ORGANISM: Zea mays

<400> SEQUENCE: 88

```
atctctatac atgagaaatt atttaggcct tgttcgatta ttcctattcc acgtggatta      60
gatgagattt agacaaaatt agaataatt ttgacttgct agggatttaa accaactcaa      120
tcccgttcaa ttcatataga ttgagattaa acaaatatt gccctagtg agattttatt        180 gcatcaacgc tcaacaccca tgtgttttta taacacatct tgcgtgacat ttgtccaact    240
actacgctaa atatgagaag ctgtcattta gtgattctat atatactatt cacttatgga    300
tacatttaac tgatggcgtt ttgttgagcg cgtcttattt atttttacat ggcagcatag    360
aagattagaa gtcgcacgtc caagttttgt ggaccgctga gaaactcaac caaattcgac    420 atattttca cctccccatg ccacaaaacc aggtcaaaac ggctttctgg ccgtcgccca    480
ctatttgtac gggcagccag acaaatattc gggtctcgca gattatttaa ggacaccaca    540
ggctgcgtta cgaaaccagg ccagatttgc caccctcgtc tcaccctccc tccctcacac    600
aaataataag gaaaggtccc gccctttcc tccgacatcc acaggggga ggggaaaaca      660 cgtgcattca cccggcggc                                                              679
```

<210> SEQ ID NO 89
<211> LENGTH: 483
<212> TYPE: DNA
<213> ORGANISM: Zea mays

<400> SEQUENCE: 89

```
cagcggcgtc gacgtcaaca gcatcaacct cgacggccgc accgcgctgc acatcgccgc    60
gtgcgagggc caccgcgacg tcgtcagggt gttgatcagc tggaaggcca acatcgacgc    120
gcgcgaccgc tggggaagca cggtgagcct gagccggccg cgcgccattg ccatttctct    180
cagctcatgc ccccatcaga tcgactttcc ttcctatcga tccatcctgc gtcgtcagac    240
cattcgcttc gcttctctga tcgtaggcag tagctgatgc caagttctac ggccactcca    300
gggtctacga tctcttgaaa ttccatggcg caaaggttcc ggtatgctta atctctgggc    360
actgaaactg aaacttctat cttgtctgtt atcgctactt gccaacgtgt gtggtggtgc    420
ccgcgaattc tccatccatc cgctgctgac ggatctatct gcggtcgttt ctgcagagaa    480
cca                                                                                    483
```

<210> SEQ ID NO 90
<211> LENGTH: 1477
<212> TYPE: DNA
<213> ORGANISM: Zea mays

```
<400> SEQUENCE: 90
aaaaagcggt cgaactgata aactactgca gaagcttctc gtttgatata acttctgatt      60
agatctataa ataagttgtg agataagttg tgccaaatag ggccatgata tatgatgact     120
atcactatgt gcaaagttat agcactataa gtgtcacgac tttattgtga cattcatttt     180
tatactcatc atgagcatca tatgcatctc aattttgatc caaaaaacta actgtacatg     240
aaaccacatt ttgttgggtt ctgcttattc ccacggactg tcaaccacat catcgtacca     300
tctacgagaa caataacata gatttagagt ttttaaccaa ttcgtgcttc cacgcactat     360
ccgatgatca ctcgaaccgt ccgctaaaat acttaatgca catagttgat ttgtcacttt     420
atggttgatt tggtgataag gggatcacga gaggattcaa gagaattgag gtccctccaa     480
ccctcataat tcctggtcac caaatcagcc ctcaggagtc tgcctagccc cattagtcag     540
gccaactgcc tccatctcgt ggggagctaa agcagtaaca cattttcact cactctctca     600
ctccactcac ttgctctctc tagttctttc tcacactttc tctaagcaca agagaaagga     660
gaagccaggg tagggtaagg taaggagaag gagagaatag tgagcaccac tagcaagaag     720
gccacagaga tcaagtaaag gtgatgacca taagaagttg gggattgaag aggaaggagg     780
cctctcttcc caacggtttg gagttaggaa gctgtcatta tagaagccat tattacggtt     840
ggtacatcta cgagatagca tacagtacaa attaatatct taataaaatg gaactcaaaa     900
tactatagct cattaaagtc gtccatgaca ttggggtcac tattggtctc ctctttctcc     960
cgctcatctt gttgctgtta cttctccttc ctcagttcct ctccacatca tatccttgtc    1020
atcctacaat tttgcataaa ggagcacacg aaaagaagag cacgaacacg aaaagaaaga    1080
gcgaaagacc agtacatgca cactataatt gctctaacaa caataacaaa acaacaatac    1140
taagtttcaa aaacacataa ttgaaccaaa catcttagaa catgaagaaa aaaaaacatg    1200
ttgaaggtat ttatagggt ggagtacatc ctcgactaca caacatggac cgttgtttcc    1260
ttttcttacc cctttacgct caatacatat atttaatttt ttctcgaggg cgattctgcc    1320
atcacgcggc ctttattttg ggtatagcta gctgtttgaa ttccaccgga ttctagaaga    1380
gacagacgct ggactggatg gtagccagag aatggatcaa ctggtctcac gtctcaaaac    1440
tcgaacaatt cacgtgcggc tataggattg gtagccg                              1477
```

<210> SEQ ID NO 91
<211> LENGTH: 796
<212> TYPE: DNA
<213> ORGANISM: Zea mays

```
<400> SEQUENCE: 91 aaagggcat gtgattggtg atccaatttc cctattatat cacgttacaa ttaaatctac       60
aaacaagacc aaaattgacc atgtttaga gtaaaaaact taatagcata tggtgggtct      120
ccagttgttt tatattacta catgtcccgt gcatcgcgac atcacataaa tatattttg      180
taaaaaaaaa gcagagaata attttggcat gtcttgtaga tagggtggt aatggatcat      240
gaccttaatt cttgcttcac aaaccaacaa ggcccttaat tttgttagtt caaaattata     300
ttgttttatg atctaaccct aacttgattc gatccttaaa tttgctagac taaattaaat     360
ggcccgttac caccctact tgtagacctc attggtccga atttagctta ggccaaatac     420
ttcgctaagc cttttttgttc tacaagacta caaccaaaga tgcccaaaat agttttgaat     480
tacgcgatgg actgcaagcc ctcagccctc acgtcccgt cctcgcttcc accttattct      540
ctatggccat cctccttcct ccaccgccaa tcccgtggcg atctctttcg gccatccacc     600
```

```
gcacccgatc cttccacctc ctttcccgag aggctcttcc cccgcgagat ttgcactacc    660
gcgtcggtgc caccgccgcc acagcacccg tggcagcagc ttgccatggc gctgccggcc    720
ccctccgccc cgccgcaggt caccgcaaga cggcgctgcg gagtgcctgg ggtgcgcacg    780
ggttgtttgg cgaccc                                                    796

<210> SEQ ID NO 92
<211> LENGTH: 381
<212> TYPE: DNA
<213> ORGANISM: Zea mays

<400> SEQUENCE: 92
ctcatgatcc atattgttat ggattttttt gagatcacgt tttctatgtt tgattatcta    60
ttatatgtca tcatcataat gttaatttat ggaattaaaa tgatacagaa aatgcctata    120
attctaacat aatctaacaa tgtttattcg ttatagtaag tgatatgtta aaattaatac    180
aaatatttat attagcattt ttagcgaata cgaatacaaa caattcaaat tttcaagaca    240
tgtacgcaac cctacgataa gacctagact ttcggtctcg gcccgttgcc tgtcttggtg    300
agacaatcaa tggccatgct tctagattgg gctcaatgga tctaatgact gggccgagca    360
gcgagatgca aatgcaatgc a                                              381

<210> SEQ ID NO 93
<211> LENGTH: 2257
<212> TYPE: DNA
<213> ORGANISM: Zea mays

<400> SEQUENCE: 93
cctcgtagtg ctaccctgcc tcgcctcctt cgtagaggtg tatggggtcc gtacaacccc    60
atggcagatg ggtaacatga cttatgggta agatgtgcca acctctacag agtataaaac    120
tggtatatcg gtcgtgctca cggtcatgag cggctcggac cctcacatga gtaacttatg    180
gaattaaact taattggtca tttgcatcgc attgtggttt atttattaat tttgatctct    240
cattatttag gttggtattt acttatactt agtaactgct aataaaactt gaccaactta    300
ttaaaagcaa tgctttgcct taaccattat ttattgatca gcctaatacc atacatgagc    360
ccccgctttt tggtgagctt atacacatta ttccccacac ttgctgagcg atgaactttt    420
gtgagctcac tcctgcgata aaactctccc ccccacaggt gaagagcagg tagcccagga    480
ggacgactgc tacgaggagt ttgacgaggt ctaggagtcg tctcccagtt gacttaatgg    540
cgccaaggaa ataatattag ttcggtttat tgttatgatt tatctttata agacacttcc    600
actttgtaaa aatgtttgcg atatttatct ctatacactt ggtcattata tggggttgttc    660 ttctttagcg cacatataag atgtacccgc gtttacccct taaattcggg tgtgacaagt    720
ttccttcctt ttcatccttc gtacagttat ctcactattt ttaatgggaa cactattcag    780
aacatgacat gttgtcaaaa catcctcccc cacatgcctt tgccatatta tatgtttcta    840
tcatggtatt cacctagtcg attaacgtcg gattctttct ttcgacaacc ctattagatt    900
gaggcgagta tggaggtgtt cgttcatgaa ttattccatt ctctgaatag aaagatcaa     960 actcattgga aaaatactcc ccaccacgat gaaacctaac atgttttatt ttctttttcc   1020
aattgattgt ccaccttagt tttataagtc ttaaaacatc ctagcgttcc atatttagtt   1080
tttagtagaa acacataaca ataccttagt tgtagcatta attaaagtca taagtatat   1140 tttacctcct tttgtcaaca caccattcat gtcacaaata ttagagtgta tgagctctaa   1200
```

```
taatgtcatg tgcctctcgt ctacagcctt gtgtggctta tgcagttgct ttgcttgcac    1260
acacgcttgg catttataac cttttgacaat attgaaattc gaaatgaagc gcatgttgtg   1320
catgtcgtgc gcccatgtcc ccgtctcgtc ccaacaagga gagcgagcgt gcgagttttc    1380
ccattttctt ttcttaatag ctttaatcag gtagagacaa ctcgactatt taagttaacc   1440
ttactcctcc taaagtaaca agatggttcc gaagttacca ccatattata catgtgtgag    1500
tgagtctttg gaatttatag aaattattat ttgtgccaag cccaaattat ttgtgttatg    1560
gaaattccca agttatttaa ttgtgctctg cagtagaccc aaattaaata gcttctaata   1620
tgtaaattaa tattaatgga aatgaactga acttatatcc cggtatcata atcattttga    1680
tggtagcata tagaacaaaa tatatttact cattctcaag tgtaactgct atttgcaact    1740
actagagcat gcaatatttc tttcgaagag attaacgtga gaggaaacat gcgtgttttg    1800
ccaatacaat aaaatatttc tcagtagcaa cttctaagta acaatattta tccatctatt    1860
tttattcttt tccgattgat tttttttgtca gaaaaatcaa agaacgggaa ttgaatttgt    1920
ctcagccaca aatgacatag aaaatattaa tccaactcca acacttgcaa aaaaaaattg    1980
caaaccaacc agctaaccca accctatttc ggtcactcac gcacggccag cccgccaatt    2040
gaatgagccg ccgtccttgc ttcgctcgcg accgctcgcg ctgccgcacc agagccccta    2100
taaaacggcg ccccgtccag aggcaggaga agcaattgag agatcaccgg ccgtcgagcg    2160
agcagtctcc caattccacc caataactaa taacatctcc tcgaacgcca ggttccttgg    2220
accactatat ccaggagcga cgaagtgatc cacccgc                              2257

<210> SEQ ID NO 94
<211> LENGTH: 721
<212> TYPE: DNA
<213> ORGANISM: Zea mays

<400> SEQUENCE: 94
acagtatcat atgtaattaa aatcaactga cgccccgttt ggatcattgg aattgaattc      60
cattctaata atagtaattt agatttatat caattaagct aattcagttt tttgcaaaat    120
atatttgtat attattatta gcaagatgtt agagatattt atgtgctata tttttactat    180
agaggagtga gacgaagagt gttatgtaag ttacagagta gaaaaaaatt atactaatgc    240
ataaaatcat ttctcatcct gcaccccatg aatttgagat agacttatat ctgaactttg    300
ggaaatggtg gaatgtcaaa tttcaaatta aataagttaa tttattaggt gaattccaat    360
tcctttgaaa caagggatc taaacgtccc gtgagaaaat ttgcatgtgc acaaagttc     420 acaatttgca tgctgacaca cgcatctctg ggtccgtacg attggtaaaa cttgatgagg    480
ttgcctttgt ctagcatccg catcaatagg acctttgaaa cggtaagagt tggtcatcga   540
gaacctgaaa aaaaactaga ggacaggagt tctttattca agcatggcct caaaatagca    600
aagtccagac ggtcatttcg tgtaaatagc agacggtgct cctctgtctc ttgcaatctt    660
ccggaacatc catcgatctc cccccagcgg cgaggagagc cggcggccac aggaaggaga    720
a                                                                     721

<210> SEQ ID NO 95
<211> LENGTH: 893
<212> TYPE: DNA
<213> ORGANISM: Zea mays
```

```
<400> SEQUENCE: 95
attcgtgcta gattgtacaa aaaaaaatgg tagcctgata ggctataatt tagagatacg      60
ataaacaaaa acatactact acagaattgg cacagctatg aatattatta tactaactag     120
gtaagcatgc caaaccaaca tccgaatcct atttgttaaa tacccagcct ttcaaagctt     180
acaaaattta acggaaaatg tgtccaagta taaaaatata gtgatcaaat gcgtgtaagc     240
agtaataacg catagaaaag gtcaagagta ctgcagttgt gttctcaatg gtgcgtaggt     300
tgtatggacc gggctgcgta gttgtgttct caatgctgga gtggaggcaa ccgagcaggc     360
cgagctgcgc cggcccatga acgtttcgtt tcactccacg gctagagcca gacggacaga     420
cgcgctccca aacacaaaca catgtacaac ttaaaaaaaa acatgagtag cttgaacgag     480
tacatacata catggcgttg ggattgacgt ccatttccaa tccaacgcgg ccgcaccgca     540
tagacgcatg ttgcatgtca tgcacgaacg ggtctagaat agacagaaga gggggggtgga    600 ggcagcagcc agatcggcgg tggctgggcg aacggacgcg cgggcaagac ggccagacgg     660
gtgttgcatt tgccgttgtg ggcaaaccac cgcgccacgg acagcgcgcg caccgctcct     720
tccaatgggc gacggaccca tataagccgc ggcgtcccgg ctccctgtcc ccactcgatc     780
gtcgtgcacg cccccgccac cggccggatc gacagcaccg atcaccctga ccgtctgcgc     840
gcggcggctc tcacacaccg gcgacacgca gggcgcgcat aggcgagggc ctc            893

<210> SEQ ID NO 96
<211> LENGTH: 2660
<212> TYPE: DNA
<213> ORGANISM: Zea mays

<400> SEQUENCE: 96
ctgcttctaa cataccttca gaatgggata tccgaacagt ggcagttgct gttttttgctg     60 cagaagcatc tttgacgcta ctggatggct cacatgctca atttactgtc atgagaaatt    120
ttttaatgca ttccactcct gtcagcctgc aggtaacgat tctttccttc ttatttgcat    180
atatgtagca ttccatagtg tgtattcaca ggtattgaat tgtggtaata ttattgttat    240
ccttctcatt gcagagcatt ccattatttc aaccttatt gcagagcagt tttgtgcatt     300
ttaaagccga acgtttgtgg atgcttcgat tattatctgc tggatcaaat ctagctgatg    360
atgctaaaat atacaagaga ggaagagtat tagaacttgc tcttgccttc tgttcttcac    420
ctatttcaga ttttgaatcg aaggttttag tccttaaggt aaattctata cttatcttat    480
ttagtccagt tgacttcctg gatctgatag ctgcttggag atttgaatat ttgtttatgt    540
ttgatatgct tgctttgcat tgtaggtgtt gaagaagtgt gttaaaata acttgcaaga     600 atttagaat aactaaaact atggtttgtg atactcccctt tgagtgtcct tacctctttg     660
atatatgata tactgtcact acataagcac acatatttct tgtttttaa tccatggcaa      720 acacttttat ccggatcgta tttattatac aagtataata tccatttgaa ggagaatagg     780
atcatgtatc ttctcttaac aatatatctt gccaattcat gcttgtaata tgcacttcag     840
taggtaactt ctgtcaatac cactttctaa gaattagaga ttgatctact tataacacat     900
ttccccctta ttcatcatcg tcccttttct atttcaatga ttacctataa tccttttcta     960
tctctactct ttattatcct ttcttatcta ttgatattat gaatactcag ttactgtata   1020
acatcttctt tgttgataaa acatatgtgc agtcagttct ttatgtagaa catgtcttaa    1080
ctaattgctt tcctgcagat ttttcatcac cagctcaata ggatgaggaa catttttgctt   1140 taattggttt gatctgtcgt ggttgcttgt aatttgatat gagcaggagg caactaatca    1200
```

-continued

```
acaatgttca gtgtgcaggg ccacaccaca catatggact gcttcagttt gtatgtcaaa    1260 tctgtttttcc acaaagaaat tgtttaaaca aaatgatcgc atcacaaaga ggatgggaca   1320
gtgatgaggc tttcaggtgg tgggcatagc tgctttcggg atagtgatga ggcaagataa    1380
agattcaaac agaagttcta ggagaaggct gtggagatag atgatctatg ttgaaaggat    1440
ggtgcatggt ggggtattaa aggctgcatg caagacaatt tcaaccatag caataaggtc    1500
acctcgcaca aagagcattt tcagaacagt aggctcgtga atatttgtt ggatatgtat     1560 tgggagcttc gtcctgttac cagttcatcc ttaacacacc taacaaggta tgacccagca    1620
cgtgcagttg acccaatcat tgaagatggt cactacacct tgtttcgaag cctagcgaga    1680
tttgacgcct cagtgttcaa ttgttacacg cagatggtat ttgtgcagat accaggttta    1740
atgttgagca cagacaatgt ttaaagattt tacgtgttga ggttgtttta cttttggcca    1800
actgttgata gtcttttttg tacaaagtg atgcattgta ctatcatata tagaagtttg     1860
catggtattg atggttccaa tatagtgatg aaataggtag attaaaatat aaaaaattat    1920
gtatggctag gatcacaaat gaattacgaa actttttctt ataacagtat aatacacatt    1980
tgtatataga gtattgttgt attacatatt cccgttgcaa cgcacgggca ctcacctagt    2040
ttagtacata taaaggtaat atatagcctt atcaacctgt ttcccatttt caaacgcaga    2100
tcacgcattg gtcttggcac ggagccactg aagttcagac aatacgagtt cgaatagtat    2160
aaaaccccaa gcatgcaatt caaagactag atctgaatgt gaggtcctcc aaaccattcg    2220
cttcagagca acaagaccct tcaaagctca accaaattt agcagacacg gcaacacaca     2280
acattggcct gctcttgaac aacaccgctg cagaatggac gttgctcctg aaacctctcc    2340
cctccaccgc tctgcccata gcccacccca ctccctcgct ataaaagcgt ccaagaacac    2400
ccaccataac aaagccgtga tccatccgaa taaacggcag actgtcatcc ctgccaaaat    2460
ctgagctcgc gtccgcagag gtccatggcg tccaagtccg tcgagctgcg catgacgctg    2520
ctgggcgtgg ccctgctagg gctgctgctg agccagcacg cggcacccgt cgatgctgcc    2580
gagagcgacg gccccagaaa ggaaaagact agcttcagca tgaacgtcgt cggcggccgc    2640
actctcagca gcttcagcat                                                2660
```

<210> SEQ ID NO 97
<211> LENGTH: 1921
<212> TYPE: DNA
<213> ORGANISM: Zea mays

<400> SEQUENCE: 97

```
gtgcatattt tctctttttt ctgttttctt ttctctttag agtttcatat ttcaaatttt      60
gaattcaaat tagagtttca aattctggtc taaatgcagc aaccaaaatc tcggcgtgcg     120
tgcaatatat acttcttgtt attatatttc atattaacta ttgtatttca aatgatacaa    180
atgtgttgca cacatacaaa gaactttaaa ttttctagaa ttatattgtt tgtccaatta    240
aaatatattt caaaactgaa tgttttatga ttatttgttt tgtatgatct ttatggagag    300
ataattcaat ttagtctta tgaagaatac ttctgaacct gtacttcaat gaaactatta     360
atttatatga ggatccttca tttaaatctc ttgttttaaa ccataattat ttaaacctta    420
ggataaagtt ttcaaaatta tccaaatat gattcaaggt gttacaaatt ctacccccctt    480 aaaaataatc tcgtcctcga gatttgtaag aaaagggatg caaaaggttt tgtttgcagt    540
ttggctttta gtttctattt ggtttcaaaa tcaaagtttt tttcaatact aattaccagg    600
tgattaggga cacatgagca tcatttatgc ctagccgact aattggcagg gtgagagatg    660
```

-continued

```
tttagtacaa ggataggttg gggtaagaaa gatttaggca aagtaagacg ccatcccaga    720
tggtggattt tgacttatct ggagatttgg cttaactcct atctttcctt gatgaggttg    780
atctatccct tctttggtct gggagcttcc attcgaacta tggacatata gttaagatag    840
atgtgggtag gatggattat atggtgtagg taggtcagaa tctctattag gttaaaacag    900
agggttatg caactatcta atgggtaagg tagttggggg acagatatcc cccaggtcca     960
ctagaaggta agaaggcctc gcgagaggct ttaggcctgt tatctcgcta gaccatccct   1020
tcgtgggcca ggagaaaact gctagtggaa tgagccggag cgagaaagaa gcagactcag   1080
gcccaagcga ctcgtgggac ttaagcgctc gtgagataat gtcgagttct aactacactt   1140
atttaccaag tgccttgctt tactgagtgt ccaacagtag ataaaagaag tgtcttcgta   1200
gagtgtcaca cactcaacaa accacctctt gccaagtgt tgtatttac cgaatacggc     1260
actcatcaaa cgctatcttt gtcgagtgtc tgacattttg ctctcgccaa atgttttagc   1320
acttgaccag aatacgtctc tggtagtgtg atatggccaa agtttatgaa atctacaac    1380
tattatgttt atcatatgat aaaactccgt gaaaacaccg ctatattttc cattggccaa   1440
tacaatacac agtggtgcgg ttggatccag ggtcttctaa tttgaaattt gtttcttaaa   1500
aaatatatat ttaaaaaaaa tgaggctgac gggcaagcca taaacagtgc attgcacggc   1560
aaggagtctc aacgaactca ttagttgcaa agcacacat ttagcgctac aaacgctgcc    1620
gccagagaaa atacagctcg tcgccattcc catactccgt gcaaggataa tcagggcgc    1680
gttgtgcgcg cacggcgcac gcatagcccg atggccgaca ccacgagagg tgtccacttg   1740
agccgacagg agctaaagac cagccgtttc gctccatgaa taatcgtcgc tcagatgata   1800
gatcacacaa ctcgcaagca atacggcagc agcgctatta tatatatggg tacaagcaag   1860
cacaagaagc atccatgctt aaggtgaagc aagcagcaca cgagacgata tagagggagg   1920
g                                                                   1921
```

<210> SEQ ID NO 98
<211> LENGTH: 1109
<212> TYPE: DNA
<213> ORGANISM: Zea mays

<400> SEQUENCE: 98

```
tgatagcttc gatgacagca aaggagcttc agatacaagc caaaggaaaa ggcgacgaag     60
acctaaatcc gagcagccga agatggggaa aatacgctac tgccctaaca acatttgtaa    120
acagtgaggg gtacaattgt aattatgtac taagtcggtt cgtctcccct ataaatagat    180
gaacagtaac ccgcataaat tacattttgc caggtgctac agctttgtat agctcaggct    240
ccaaaacaca ttcgtgctat cttgcactaa gaagtcaatg gtatgattgt aaacttgttt    300
tctataagag aaatgaaatt ctaaggcaca tgagatgagt tctcatatct tcgtcatgtt    360
tttatgtatt ctagtcgatt acatccaacc ttcgtccttg agtagttatc ccaaagactt    420
aacacttcaa ggatgaaggc ttctactttt taacattgtg ttgtcttgtt ttttatttca    480
tttagcaatt aaaagcaagt gactaacaca tggttaaacc caagatccga aaagaggcta    540
aaattgagca agaatgaaca aaagttggta agaggaacat aaaccaacct ttcttagcaa    600
cattcttcca aaaaagaag atcaaaacat gtacccttgt attttgtgaa aactggatct     660
ccaaaattgc ctacaatgga aggtggctac gagaaacggt tataatcgag gaggtagaga    720
gaattttatg ctacaacctt cacaggcggt ttccctaaga aacatccact ctaaatgtct    780
ttgcacatac ggttcactta aaaaaccgca aatgcaaatt gttcattttc actggaggtt    840
```

| ttttaagcga accgctagag gaaatctcat ttgcaccggc gatccttaag acatatcatg | 900 |
| agcgaggttg ccttggaagc cggaagagtt ggtcaatgac ctataaaaag cagaggacac | 960 |
| aggagtgccc tattcaagca ttgcctaaaa atagcaaagg ccaaacgatc atttcgtgta | 1020 |
| catagcaaac ggtgctcctc tctctcaaga aaggatatct tcgggaacat ccatccatcc | 1080 |
| ccaatcccca aaggcgagga gagactagc | 1109 |

<210> SEQ ID NO 99
<211> LENGTH: 1559
<212> TYPE: DNA
<213> ORGANISM: Zea mays

<400> SEQUENCE: 99

| cctcaggcgt ctttctggaa ctgattcgtt ttcgctgctg ctctctgctg gttgctgcag | 60 |
| gataaagttc ttctcaactg ctcaggggc ggtgtgtgcg ggacctgcgt cgtcgaggtg | 120 |
| aacccaatgc agccagtcac aactcattct tctgaagcct gatgcagtga catttttctgt | 180 |
| cgaagatagg gcacaaggaa ctctgcagga taggtttcct gaagcctgcc tgatagtaca | 240 |
| gttcattttg acactttgcc gcttcgctaa atttacaggt ggtcgaaggc aaggaaatgc | 300 |
| tatccccaaa aaccgaagtg gagaaggagt tgctcaaaag ggtttgtagt ttgcacacac | 360 |
| gactccatct gttcatcatc agaaccgttt tctttatcag aagaataagc ttgcaaactt | 420 |
| cctagttttt aagtaaaagt gctaacctct tcgcgccaat tttcagaaac ccaagacgtg | 480 |
| gagattggcg tgtcaggcaa cggtgggcaa tgcagattca accggacagg tatgcacgaa | 540 |
| tgctttccag tgtttgcttt cacgtactgt attcccaaac gaaaaggaa atttgaactg | 600 |
| tccgttctga attttccgtc gaaagttgct ctgaattttt ttacaccatt attctcgaat | 660 |
| atatatgctg ccactggata acgttttagc cgtgctgctt catgtttctt ttcacaaggg | 720 |
| cataacgttg atagcatgcc tatgggattt gttgttttgc gcagatgatc attcaacagt | 780 |
| tgccggagtg aagatacat gagtgggaca agtagaaggg cagatgccat ggaaaatggg | 840 |
| gaaaatgaga agcagttgat cagtagaata gctggtgcag attgatgaag cttttcatac | 900 |
| tcaagcaaaa tcttgggcat gttttttcacc atttgtagca caactgaagg agcatggatg | 960 |
| aattagcatc gtcctgtaaa ctgttctctt ataatcagat cttgtttgga agcaactcag | 1020 |
| ttttaagaa actgactttt attttttag ctaggagtga ccggtttcat tgttttaaaa | 1080 |
| aactgaaat ccaattcta caaactgatt tataaatcga tatgtttgga accaccttaa | 1140 |
| ttttaagatt agatgttttc aaacagaccc tacaaaaca ggcgacttgt gtgcgcgcgt | 1200 |
| ctcgccggat cagatgtagc attgtcttat tggtggagcc caacatcatc taatggcatc | 1260 |
| aaattaatta acaacattc tacatataag agagttatat attttaggtt tttattggta | 1320 |
| ttcttgtata atgcgatgct tttttagga gtgcgttggc aacgtcctcc tgttgctcca | 1380 |
| agccgtccat agtttcattt tcattgcacc ggacatgcat ccacagcaaa gcacgcatgc | 1440 |
| atctaaaaat ggcaggtgca tgcctgcgcc cctacgtata tattactatc acgtagcttg | 1500 |
| ctataccaag gacaaatcaa accatagcat caatcatgtc tggtcgttcg tggacaata | 1559 |

<210> SEQ ID NO 100
<211> LENGTH: 1821
<212> TYPE: DNA
<213> ORGANISM: Zea mays

```
<400> SEQUENCE: 100
aaactttgca aaacccaccc aacaaaatca cccccacatc cataacctct actaaatcca      60
ccaaacaaat tgcatccaaa cttaacacac cattaaaata aacggttcag atcgctagat     120
aaccccctta cccttacttc actcaaatct aatagacaat attattaaga tcatccctta     180
tccctcattt ctctccatcc cctcccctgc gaccacaccg ccctagcct cccccacagt      240 attcccgctg ctgctgctgc tgccataaaa cctcccctcg caccactacc gccattgcca     300
tcgaccccac cgctctacgg gattgtagct ttagcacgag ctatatacta gtatgaataa     360
agaatctttt agccataaat tttgtggggg ttaaaactct agcaacgagc tacatttccg     420
gtcttatttt gtgctagtat ttgcacttct aagcccagat agtccatatt tcagtgttca     480
atttaatttt gtcatatgtg tgaactagtt cattaggact tgcgtagtaa gtttgggata     540
atcacaagga aaatgactcg acaagaggtt aacggttcta gtttgtggtt actaaattct     600
caataatttt cttgtagatg gtttgtcgta gatttaagga caaatccaga tgcatctcaa     660
atgtgtgcta ggatcaagta tcatacatat gatgactcat ggtacagaaa tcaatgtcac     720
ctctttatta tataatagaa gttctataca aataactat ataaatacgt cataaaacga     780
ctacgatcct ccacaaccac agctgactag gagacgacga cctaaacccc tccgaactca     840
tcgtagcatc cttcatactc atcatcttgt ggtacctgtt cttgacatgg tgtgattata     900
gcaagggtga gctctcatat ggtcatcact cagcaagtgt ggggaaaagt acactgtaag     960
gcttaccaag gaaatgatt aaggctgagc attgctttta attttgttgg tcaaaatttt     1020
attagcaaat actaagtata agtgaatacc aacccaatta ataattgat cagaaataaa     1080 tacccaaagt acatggagtt gtattttgag aaaatcatgg agatatgatt accttcttgc     1140
actattagta tatcacattg cagatgtatg tattttattt ttttatctag atctttccat     1200
gtgaagggca agcctggtgc gttggtgaca gctgtcccac ttagtcgcca agttgtaagt     1260
tattgaccat ttccttatt attattaggg tctcagattt atttgttctt aaaccgtaaa     1320
ccggtaatcg ctgtctattt tagttgtccc acttcatttt tatttttatc caagtgaggg     1380
gcggcacatg tcagcgtcaa ccagtaattg ctgtctattt caaggtggct cgatggtagg     1440
tcatccacca atgaataatg ttagctagcg acaacactag gagagtggag gtaaccaatt     1500
ttgggttgcc cggtgactct gctacctcgg gcaggtactg actgatctca ttactcgcat     1560
gtctggacga tatccgatga ctctagctaa aaatatacaa acgtttgcat gtctgccaca     1620
ctacacttaa atctctggtc tcccggcaaa aacgaagatc aaactagcaa ttagaaattg     1680
tgcgttcaca accattaaaa tcacccgtag cccgtgaagt tctcttctcc ccatagttta     1740
tttacttgtc ttctatatat aaagggctaa tgaaaagttg agcaaagtca tctcgtgcca     1800
ttctaaatag aagcactact g                                              1821

<210> SEQ ID NO 101
<211> LENGTH: 593
<212> TYPE: DNA
<213> ORGANISM: Zea mays

<400> SEQUENCE: 101
aaattgtttt ttatgagtaa tggaattttt gtttgcttaa ttatatgttc attttaataa      60
aacaacatat tttgttataa ctaaaagtct ataaaaaatg atgtaacatc gtatgtttag     120
tttgatgtca aaataggatg agccgagcgt gacaccatcc tcttgatttt ttgggactcc     180
gtcgtcacca aaaattgctc cggtgttcat ctcgtccgcg cgtaactttt atccaaaaac     240
```

| | |
|---|---|
| aatagaaaat gtgaccgtcc cttctatcct cgttatacat ccaaccaaac gcattctaaa | 300 |
| gttgagatgg ataaaaaaac gatgatcaat aacaacattg ataataaaaa acaagagttc | 360 |
| aaatgacatg gtgtgatggt gaatatatag acggcataat gaatagctgc cacctgctat | 420 |
| acagtccggg tccaaagtgt ccaactcgat agacgaccca ccagcgtcct agcttgccta | 480 |
| tatatgccac ctcttctcct ttcttgcatc actgctcgag gcttctagta gagagcacag | 540 |
| ctagcaaaac agagctccag aaactgaccg attggtttca caccagagtt agc | 593 |

<210> SEQ ID NO 102
<211> LENGTH: 391
<212> TYPE: DNA
<213> ORGANISM: Zea mays

<400> SEQUENCE: 102

| | |
|---|---|
| attcgtgtca caaagcctta acaataatcc acctgcatga tatgttttga ttgtgcgatg | 60 |
| ttaagaaaag attgttggat aggtgagcga tgccaatggc cgggacctgc tgcaccaaac | 120 |
| agagccagcg gcccgccttc ctcctcgcgc ctccgaaaca aacagcaac gacgtccagc | 180 |
| caggggaggg gccatggggc cgcagtatat atacctgcgc cttgtaccac cgcccaccgt | 240 |
| cgcaccgtgc gcgcgtccct cgctcctgcg ccgcccgtcc gatccggtca ctggccgggg | 300 |
| agggctcaga aacctttcat ccaatacata catctatctg agcccttttcc cgcggtgagg | 360 |
| cccgaccgga gtccacacac acacggtgtc g | 391 |

<210> SEQ ID NO 103
<211> LENGTH: 1223
<212> TYPE: DNA
<213> ORGANISM: Zea mays

<400> SEQUENCE: 103

| | |
|---|---|
| ctctcagcaa aggacggttc gaccatggag cgcagctcag cccaggggat ctccaggtag | 60 |
| tctttcctgt catcatcaga agagaatata tagcacgtat gaagggactt tcctattatg | 120 |
| atttagtgtg aaccaggtga tgcattcaac atcaggctat taagctaagc tgtcataagc | 180 |
| acagaaatgg atcaggcaat tagattcaga gcttgaagta cgtctgtaga aagaaaactc | 240 |
| aaggtcatcc cccatttcta ccccccctccc cgatgcaata ctagatccgg tcatatctct | 300 |
| agggccgcaa tgattcgggg ccgccatacc ggtggagagc ctaggcgacc gaatcacaca | 360 |
| catgggccgt ggaagcacgc acagccactc aatgacacac gcacccggca cccagtcaga | 420 |
| gaaagcaagc agccggtcgg ctcgggattt ccgcaaacgg gtagcaggcg cagggaggga | 480 |
| gcgggcgaag aagccttacg ggtcgaggag gacgacgtcg gcgtggccct gcatagtctt | 540 |
| ggcgaggagg gagccggcga cgccgccgcc aaccaccacg accctcgcct tctcctccgc | 600 |
| ctccgccatc gcctgacgct cgcgccaccc agctgacaaa ctccccaccc acacccagct | 660 |
| cacgcggcgt tattaaccaa gctcgcgagg acataagtgg cggctttgga agaatcgggt | 720 |
| gccgagtgct gaccgaccgc tgacgactcg agtactcgac cgacgcgtcg ggacggacgg | 780 |
| tgaagcgcgc gccatggtgc tgccacccc tctcaggctc tcaccatccg accgcatgtg | 840 |
| acctaccgac atgtgaatgc agttcttaac aattcttcta ctctactgga ctactactac | 900 |
| acgactacta ttattataat tacatgaata ataagctgt caatgaatct atttaaacaa | 960 |
| aaaaaaagtt gtctttgcca tgacagggca tggtcgctgt cgcgtggtcg aaagtagcct | 1020 |
| ttgccagcag cgggtaaccg aaataaccgt cgcgaactac cctccgagcc gtaggtgtac | 1080 |
| aagagcggct ggggatgctg ccacgtgggc cacccgggcg tctttaaacc ggcccgctgg | 1140 |

```
gagttccatg cttcctcgtc cctccctgca cgcctggcct gggctggccg cctccgacca     1200
ccgtacgttc tccaccacgt cgc                                             1223

<210> SEQ ID NO 104
<211> LENGTH: 1799
<212> TYPE: DNA
<213> ORGANISM: Zea mays

<400> SEQUENCE: 104
ccttttgggc caatcacgat gggccttagg acactttcta aggcaagaac atgaaccttt       60 ttcttttttct catattgtca tctgcgtatt gtttcatgaa gttgctatgc aacgtcacct     120
gaagttgtaa ccaactccac gtcacctgaa gttgtaacca actccacgca tataatattg     180
gtcctatttt gcagagcgta ggttctgttg gatctacctg atcaatagtt agcggctagt     240
gtaaataaaa tagatcctat gatccatcta agtttgaatt tcatgtttta ataatcagta     300
tgtgactatt taaactaatc ttatttgcta atgttttttc gatatagttt aaaggctgta     360
gaatatactt gaacttaggc aaagtggtga ccgagatgat caacacatca atcaagacgt     420
tagaagcctt gatgaaacat tcacgagaga cgagcaagga gtctaagacg ctaagataaa     480
taaaacctag accaaggcat gtggagaaat aaagtcaaac aaatgctact cgacaacatc     540
cagcttgtcc agtactgcac cagaccagcc cagagacaaa aagttcaaaa gcatgtaaaa     600
agaacacaac ggtaacacac cagatgtgtc cggtgctatg ccctatgaca taaccaacgc     660
cacaatgtgc acgatgtgct ctagaatgtg aggccagacg catccggtgg cacaacgaac     720
actttactca tctagggtta tagagtggat tgcaacatga cttggagatg acgacaactt     780
accgaacgtc acatttgacg acagatctcc aatggccaat aactgctgga aagccaatag     840
atacgtcaca tggacgcacc aaacgtgttt ggtgtctatg taaaatttgt tgtgtatccc     900
cacgaccaca tttacattgg gggctatata tacccccttg ctagccaaat agagggtggt     960
agagtatgtt gaaattgtag gagagtgtca agacacttca tcaagtgctc taaccacaca    1020
aaaaacactt aacaaaagat tagatgagca gcatagtgat ttttgtgaat tgcttatgct    1080 agttaaaacac atttatttac ccttgttgta ggttagggcc tagtgtttag tgttgtttgc    1140
atagcgctct taccactcat acactatttt tgtacaccag gggcctgaag tcttacacca    1200
atcgtgttta tggtgtgttc gtcaccgtgt gctaaaggaa acgaagccca caaggaccga    1260
ttcaggagaa gccattttag agacacactt atgtgtagtc aagtcacatg atctattcat    1320
agagttattc gacctagagc ttgacccttg tacgggaatt tatgcgatga gctttaatga    1380
ggactaagaa agctaagata caattaaact tattccgaaa ccgacaatta aagacacttc    1440
ttgggacgga gggagtagct gacgttccgt aatgcatgca agagaagtga ggagggccac    1500
gctagagaag agaagtacag aacggaatga gggacggtgg cgcatgtccc cgcaagatcc    1560
tgagctgatt ctaaatcaag catttgcttg accaagtcta tgcggcgcag agcccgcccg    1620
cgccctatgc ttgctccgga gctctcgttc gttccctgcc gcggcagcca tcgatcaccg    1680
gccccaacgc tagctttagc ttcgcctatt tacatacccg agcggagaag agaagagaag    1740
agaagcgatc gggattgtgg gcgagtgcgt gcgttcgtgc agccacagac aggcgtcgg    1799

<210> SEQ ID NO 105
<211> LENGTH: 1745
<212> TYPE: DNA
<213> ORGANISM: Zea mays
```

<400> SEQUENCE: 105

```
atctagtttt acagatctgg ctttggatag ttttcatggg ctgacaaaat tcgaggactt      60
gtttgcttgg ttttctaagt ccggggtaga tgacacaaca tgacaaattt gtgaaccact     120
agtgtacttt actctttgtt aatatattga gacgaatcga gttgagttgg ctcattatca     180
atcaaccttg gttgactgta acctttttgac accggcacca ttttctaca gcactatata     240
tgccagtttt ctgtcgttgg ttattgtgga agagggtcga caatggtaa atttgtatgt     300
tgcaagaatt tgaaatacag tagaagtaat aatataattg atccccaacg aaataaatca     360
ggaggaagac ctcttctcgt ccattactag cagtaccata aaaagagaac agtggcaacg     420
gccacgatgc agagagagta ctgccatgca aaccattgga agccggtagc ctaaaacagt     480
cgggacccaa cccaaagcag ggaggtcgc tccaggcaag aactgctcgt gtccacacgc      540
tacgccgggg atgccggcct ttgtaacata tataagcgtc gccgcgaggc ctcgtcctcc     600
cagtcccaga taaccccaca tcgtcagcca tggccaacag ggtcaccgtc gcaagcgtca     660
tcgccgcggt ggacatcgtc gccgcgatcg gcaccatggc cgcggtgacc agcgccgacg     720
acaacgatgg caatatgctc tccagcgtgg aggtctccac ggtgtgcgcc ttcacgcggt     780
acccggagaa gtgcgagcag agcctcaagc atgtcgtgag cgacacctcc agcccggagg     840
acgtcttccg ggacgcgctc aacgtggcgc tggacgaggt ctccaccgcc ttccagcggt     900
ccgcgcacat tggcaaggac gcccaggaca aactcagcag gaacgccatg gacgtgtgca     960
agaagctcct ggacgacgcc accgaggacc tcagggccct ggcacgggtc aagcccgcgg    1020
acgtggtgcg ccacgtcaag gacctccggg tccgggtctc cggtatcatg acctacgtct    1080
acacctgtgc cgacgggttc gagaagcccg agctcaagga ggccatgggc aaggtgctgc    1140
agaactccac cgagctcagc agcaacgcgc tcgctatcct caccgcctc ggcgatctca     1200
tgccggggaa agccaaagat ctgcaggcca ccctggcggg tgctgtgggg cacgaccgcc    1260
ggcttcttgg cgggcagata ggcgatgccg aggaggtgac cagcggcggc cgcgggcttc    1320
tggacgagat cgtgggcgtg gcaaacgcaa accggaagct cctgtcggat acgctggacg    1380
agatcaccgg catgtcccac ggcgcaaacg gccggcgctt gcttagctcc ttgggtctc     1440
ggatttccag cgcccaggga gacgacgtcc ccgcccgcca ccagctgctg ggcgtgtcgc    1500
ccgacgacga gaccgataac gctgcccggc gcaacctttt gtccaccgag ctcgagagca    1560
tcgccagcac gtccgccgtg gcaaaccgcc agcttctcgc ggcggaggag ctccccgacg    1620
agctcgccgg taagcgagag ctgctgtccc ggacgctcat ggggatcgac gaggcggcca    1680
ccgaggccaa gcgccagctt gatgaggcga cggcggagaa caccatgtcc ggcgaccaca    1740
gggta                                                                1745
```

<210> SEQ ID NO 106
<211> LENGTH: 1151
<212> TYPE: DNA
<213> ORGANISM: Zea mays

<400> SEQUENCE: 106

```
aagctttctt tgccgagtgc cactaagcga ggaactcgga cactcagcaa cagctctgtc      60
atcgtcacga tgtcttttct ttgtcgtgta ccagttggca ctcggttaag actttactga     120
gtgcccgata gaaagtactc ggcaaagaga ccgttgccga cgtttggttc actgagggct     180
ctttgctgcc ttttggactt gacaaagaag tcatctccag tactgtctcc taggacgcag     240
gatttatgtt ttttcccgga gctcgatctg tgggacatca cagatggtcc agtctggtga     300
```

| | |
|---|---|
| tctaaaatgg acggtttgcc aagcccacag agaagtctttt aagatcttcc acgacgcacg | 360 |
| catgctttaa ggttagttag tgtttggtct gaaaaagcat caacaattag gaaactagaa | 420 |
| ctaaaattat taaaggacaa ctcgggaggc atgcatgttc ttcttctata gtgcgtgttg | 480 |
| agcctgagtt tggccttttta ggcttttatta gggggctcgc agtctagcta aggagttgta | 540 |
| ttgatgtgct gataaatatt atgttcgatc gtcaaagtgg tcttgtgcgg atcaattagg | 600 |
| ctcgatcatg gtgaaataaa ctaaccatcg gtaagcccgg gcagcccag agcatgcagc | 660 |
| ggcctacgtg aagcctgcgc atcgcatcgt cgtccatcgg acgctaacgg ccggccgctg | 720 |
| catgcgccgc cggcgaactc tctgctgagc cgcccgtcct ccctataagt agccatccca | 780 |
| gcaccgtcgt ctatcaacca cagacagagc gacatttcga ataacacagt tcagcgcgac | 840 |
| gatgggatcc ctcactaata acatcgtggc cgtgggcgtc gtccttgcgg cgctcgtcgc | 900 |
| cggcgggtcg tgcgggcccc cgaaggtgcc acccggcccc aacatcacca ccaactacaa | 960 |
| cggcaagtgg ctcaccgcta gggccaccctg gtacggtcag cccaacggtg ccggcgctcc | 1020 |
| tgacaacggt acgagcggga tacatgtttta tactcctcct gtaggtcgct ccttcatgta | 1080 |
| atgtgatgcg attaaaacgg tgcgcaggcg gtgcgtgcgg gatcaagaac gtgaacctgc | 1140 |
| caccctacca g | 1151 |

```
<210> SEQ ID NO 107
<211> LENGTH: 2654
<212> TYPE: DNA
<213> ORGANISM: Zea mays

<400> SEQUENCE: 107
```

| | |
|---|---|
| ctggtctgat tttgatgtct ttttaaatcg gctttcacag gctaaagccc gctgatgtag | 60 |
| ctgagctatt gaaaagaact gggtcccatc taatttgtct cttaagcagg atagcaaccc | 120 |
| atcaaaagcc atccctgcta gctctttgtc tgcgacatgg atccgaaagc atcgatttct | 180 |
| agtgtctcgg aacctccaga tataatagtt aaccgattct tcacgtccct atcaagctaa | 240 |
| agctaaatca gctagaccta attcatttc cccggaaaag aaatgtccat gaaatttact | 300 |
| ctctaaatca ttccaagaat taatggaatt aggaggcagg gcggcgtacc aagcaaaagc | 360 |
| ggtaccagta agggataaag aaaataaaca aacacgaaat gcttccccat cggccaattc | 420 |
| gcctaggtgt gctaggaact ggcctatatg ttcgtgtgtg cttctcctat tttcaccaga | 480 |
| aaacttagaa aactctggta tcattgcccc ttgtggatat gggacaatgt caaaccggtg | 540 |
| atcatatggc ttctgatatg attgccccac tctatccaca ccaactccga gtctatctca | 600 |
| aaatagttta gccatctctc ccctaatttt ctacattgca ctcggtggca gaccaccgga | 660 |
| ccctaggctg tggggttcat tcggtcgggc attgttatgc cgaccttctt gccatgaccg | 720 |
| attgataatg ttgatcggcc tgtgatcata tggcgtgttg tgggttaaat atgtaggggg | 780 |
| cagaacatac tgccgttgtg gtatgtaata atttggtgca tagtgtgcga cagtaggttc | 840 |
| tgtgtatgtg tatccgatat gtccggtggt acacctgaac tggccggttg tgttagctat | 900 |
| tattggggcg ccacgcggta gccctggtgc ggtcccggac tatccggcag agaaggccgg | 960 |
| acggtctgtg taagggccga actatccaga caaaagcttg gacggtccga ccgtgtagag | 1020 |
| ggccgccgat ctgccaagca aggacgatgg tgatggtatt tgccctggat atgagttcat | 1080 |
| caacatacca tataatggat ggggctgcaa atccccattt gtcgccgatg tattagacat | 1140 |
| aaatatcatg ttactagttt catatgatgg aaaactagga gcaacagact tctccaacat | 1200 |
| acacgttaat tttctaattg gttcttctaa ccctctaatc taatgcttca cttgattatg | 1260 |

```
caaatggtct acatactgtt aatagattg gatgtcgtcg ggtttactta cgttagggac    1320
ttgaagcgaa gatagaagag atgtgacgtc gatatcgcat gtttgacaac tttctggtga    1380
cgatccacca tgtattgtga caagaatttc tccttcgttt gacacatgta gtcctcgtat    1440
tgttgttgct catcggtcgt cggactcttg atagccggct ttaggatatt gtccggggag    1500
atatcggtgt gatctttaga accggccatt tgatggcctg agttttagta gatctagacg    1560
catttcccca acggagtcgc caaaaagtgt gttggcgccg atccaggcgc gaaacactgg    1620
agatggaccg tttggcggtg ttctctgcgg aggtgaggac ggtccgcgac ctggcgcagc    1680
agcgactctc ctctacgtgt gtccggacgg tccgcgtctg gggctcggac ggtccgcgat    1740
ggcgcagagg gtcttcttct tcgcagccga cctagatctc gcctcccggg aggggcccccg   1800
tcggggagga gagattgtag ggtgtgtctt ggcgtcgaca ggccacacaa tacgcctcta    1860
gtcgacgtag agccgaagag aggtgaagga ttgaggtgga aggaggctaa acttgggcta    1920
aactagaact actgctaatg cataaggtaa aaacgagaag tggacttcat ttgatcgatt    1980
gtggaaggtt taatcgactg tagcccttta tctatataaa ggggaggtat ggacccgtta    2040
caagctgttt cccgagctaa tctcacggtt ttagttaata atcctgcga gaaactcgga    2100
actctaactt gattctactc atgcgcgaac cattcgtgcc tgccaccgct gcccgtccgg    2160
ctacgctcag ttaaccctgt gttgtgcgct gtgatttggt ggcatataag accacatttg    2220
caataaaaat ttgtagggat ttaacatacc aagtgctgcg gaaaggaatc gttttcggag    2280
gacccaaaat taaagaggca gatgctagag ctcgtccagc tcagcgctga gcacctgtgt    2340
tgtcctcctc gtccacgccg gcggagatga acggcaacaa aggcggaaag gccgagacgc    2400
tgagctcaag gacgtgacac cgcgcgtacc tcgcgttcag ttggctcaca caacagcagc    2460
tcgctcgccc caagctcccg cgtcctgatc cgtaggtgag ccatgcaaag gtcgccgcgc    2520
gccctgatcc attgcaccct tcaaagctcg aacctacaaa tagcgtgcac caggcatcct    2580
ggccacaccc acacagcaag ccagcagagc agaaagcagc cgcagcccca gccccacaa    2640
agacgaaggc aaca                                                    2654
```

<210> SEQ ID NO 108
<211> LENGTH: 537
<212> TYPE: DNA
<213> ORGANISM: Zea mays

<400> SEQUENCE: 108

```
tattggtctc ctctttctcc cgctcatctt gttgctgtta cttctccttc ctcagttcct     60
ctccacatca tatccttgtc atcctacaat tttgcataaa ggagcacacg aaaagaagag    120
cacgaacacg aaaagaaaga gcgaaagacc agtacatgca cactataatt gctctaacaa    180
caataacaaa acaacaatac taagtttcaa aaacacataa ttgaaccaaa catcttagaa    240
catgaagaaa aaaaacatg ttgaaggtat ttatagggt ggagtacatc ctcgactaca     300
caacatggac cgttgtttcc ttttcttacc cctttacgct caatacatat atttaatttt    360
ttctcgaggg cgattctgcc atcacgcggc ctttatttg ggtatagcta gctgtttgaa    420
ttccaccgga ttctagaaga gacagacgct ggactggatg gtagccagag aatggatcaa    480
ctggtctcac gtctcaaaac tcgaacaatt cacgtgcggc tataggattg gtagccg        537
```

<210> SEQ ID NO 109
<211> LENGTH: 577
<212> TYPE: DNA
<213> ORGANISM: Zea mays

```
<400> SEQUENCE: 109
tggtagcata tagaacaaaa tatatttact cattctcaag tgtaactgct atttgcaact      60
actagagcat gcaatatttc tttcgaagag attaacgtga gaggaaacat gcgtgttttg     120
ccaatacaat aaaatatttc tcagtagcaa cttctaagta acaatattta tccatctatt     180
tttattcttt tccgattgat tttttgtca gaaaaatcaa agaacgggaa ttgaatttgt      240
ctcagccaca aatgacatag aaaatattaa tccaactcca acacttgcaa aaaaaaattg     300
caaaccaacc agctaaccca accctatttc ggtcactcac gcacggccag cccgccaatt     360
gaatgagccg ccgtccttgc ttcgctcgcg accgctcgcg ctgccgcacc agagccccta     420
taaaacggcg ccccgtccag aggcaggaga agcaattgag agatcaccgg ccgtcgagcg     480
agcagtctcc caattccacc caataactaa taacatctcc tcgaacgcca ggttccttgg     540
accactatat ccaggagcga cgaagtgatc cacccgc                              577

<210> SEQ ID NO 110
<211> LENGTH: 623
<212> TYPE: DNA
<213> ORGANISM: Zea mays

<400> SEQUENCE: 110
ctgcagttgt gttctcaatg gtgcgtaggt tgtatggacc gggctgcgta gttgtgttct      60
caatgctgga gtggaggcaa ccgagcaggc cgagctgcgc cggcccatga acgtttcgtt     120
tcactccacg gctagagcca gacgacagag cgcgctccca aacacaaaca catgtacaac     180
ttaaaaaaaa acatgagtag cttgaacgag tacatacata catggcgttg ggattgacgt     240
ccatttccaa tccaacgcgg ccgcaccgca tagacgcatg ttgcatgtca tgcacgaacg     300
ggtctagaat agacagaaga gggggtgga ggcagcagcc agatcggcgg tggctgggcg      360
aacggacgcg cgggcaagac ggccagacgg gtgttgcatt tgccgttgtg ggcaaaccac     420
cgcgccacgg acagcgcgcg caccgctcct tccaatgggc gacggaccca tataagccgc     480
ggcgtcccgg ctccctgtcc ccactcgatc gtcgtgcacg ccccgccac cggccggatc      540 gacagcaccg atcaccctga ccgtctgcgc gcggcggctc tcacacaccg gcgacacgca     600
gggcgcgcat aggcgagggc ctc                                             623

<210> SEQ ID NO 111
<211> LENGTH: 1040
<212> TYPE: DNA
<213> ORGANISM: Zea mays

<400> SEQUENCE: 111
cgtgcagttg acccaatcat tgaagatggt cactacacct tgtttcgaag cctagcgaga      60
tttgacgcct cagtgttcaa ttgttacacg cagatggtat ttgtgcagat accaggttta     120
atgttgagca cagacaatgt ttaaagattt tacgtgttga ggttgtttta cttttggcca     180
actgttgata gtcttttttg tacaaaagtg atgcattgta ctatcatata tagaagtttg     240
catggtattg atggttccaa tatagtgatg aaataggtag attaaaatat aaaaaattat     300
gtatggctag gatcacaaat gaattacgaa acttttttctt ataacagtat aatacacatt     360
tgtatataga gtattgttgt attacatatt cccgttgcaa cgcacgggca ctcacctagt     420
ttagtacata taaggtaat atatagcctt atcaacctgt ttcccatttt caaacgcaga      480
tcacgcattg gtcttggcac ggagccactg aagttcagac aatacgagtt cgaatagtat     540 aaaacccccaa gcatgcaatt caaagactag atctgaatgt gaggtcctcc aaaccattcg    600
```

```
cttcagagca acaagaccct tcaaagctca aaccaaattt agcagacacg gcaacacaca      660
acattggcct gctcttgaac aacaccgctg cagaatggac gttgctcctg aaacctctcc      720
cctccaccgc tctgcccata gcccacccca ctccctcgct ataaaagcgt ccaagaacac      780
ccaccataac aaagccgtga tccatccgaa taaacggcag actgtcatcc ctgccaaaat      840
ctgagctcgc gtccgcagag gtccatggcg tccaagtccg tcgagctgcg catgacgctg      900
ctgggcgtgg ccctgctagg gctgctgctg agccagcacg cggcacccgt cgatgctgcc      960
gagagcgacg gccccagaaa ggaaaagact agcttcagca tgaacgtcgt cggcggccgc     1020
actctcagca gcttcagcat                                                 1040
```